United States Patent
Gebrian et al.

(10) Patent No.: US 6,632,654 B1
(45) Date of Patent: Oct. 14, 2003

(54) CANISTER FOR INVENTORYING SUSCEPTABILITY TEST DEVICES IN AN AUTOMATED MICROBIOLOGICAL ANALYZER

(75) Inventors: Peter Louis Gebrian, Wilmington, DE (US); Allan Lee Cameron, South Natick, MA (US); Alan Christopher Mudd, Beverly, MA (US); Patrick Francis McDermott, Oxford, MA (US); Adrian Mark Thomas West, West Newton, MA (US)

(73) Assignee: Dade Microscan Inc., West Sacramento, CA (US)

( * ) Notice: Subject to any disclaimer, the term of this patent is extended or adjusted under 35 U.S.C. 154(b) by 147 days.

(21) Appl. No.: 09/924,384

(22) Filed: Aug. 8, 2001

(51) Int. Cl.[7] .................................................. C12M 1/34
(52) U.S. Cl. ............................... 435/287.3; 435/287.4; 435/809; 422/104
(58) Field of Search ................................. 422/102, 104; 435/287.3, 287.4, 809

(56) References Cited

U.S. PATENT DOCUMENTS

| | | | |
|---|---|---|---|
| 4,448,534 A | 5/1984 | Wertz et al. | 356/435 |
| 4,643,879 A | 2/1987 | Hanaway | 422/104 |
| 4,676,951 A | 6/1987 | Armes et al. | 422/65 |
| 4,681,741 A | 7/1987 | Hanaway | 422/100 |
| 5,266,268 A | 11/1993 | Antocci et al. | 422/72 |
| 5,292,484 A * | 3/1994 | Kelln et al. | 422/102 |
| 5,538,688 A | 7/1996 | Teznka et al. | 422/64 |
| 5,627,041 A | 5/1997 | Shartle | 435/7.24 |
| 5,670,375 A | 9/1997 | Seaton et al. | 436/48 |
| 5,762,873 A | 6/1998 | Fanning et al. | 422/65 |
| 5,807,523 A | 9/1998 | Watts et al. | 422/64 |
| 5,863,754 A | 1/1999 | Bajard | 435/39 |
| 5,863,800 A * | 1/1999 | Eikmeier et al. | 436/48 |
| 5,888,455 A | 3/1999 | Seaton et al. | 422/65 |
| 5,922,593 A | 7/1999 | Livingston | 435/288.5 |
| 5,965,090 A | 10/1999 | Fanning et al. | 422/65 |
| 6,086,824 A | 7/2000 | Fanning et al. | 422/65 |
| 6,096,272 A | 8/2000 | Clark et al. | 422/64 |

* cited by examiner

*Primary Examiner*—David A. Redding
(74) *Attorney, Agent, or Firm*—Leland K. Jordan

(57) ABSTRACT

An elongate canister having a generally rectangular cross-section sized to house a plurality of antibiotic susceptibility test arrays stacked one atop another and maintained secure within an environmentally controlled inventory chamber in a random access microbiological analyzer.

9 Claims, 44 Drawing Sheets

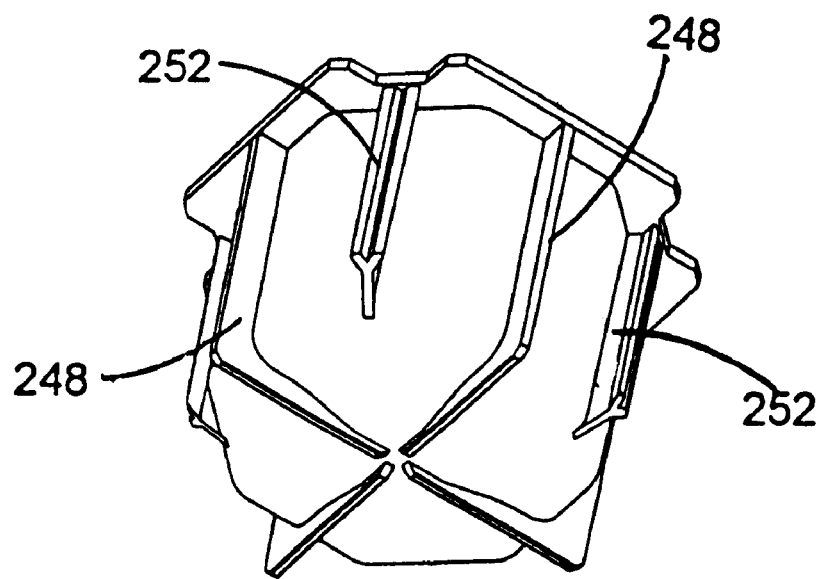
FIG. 12A
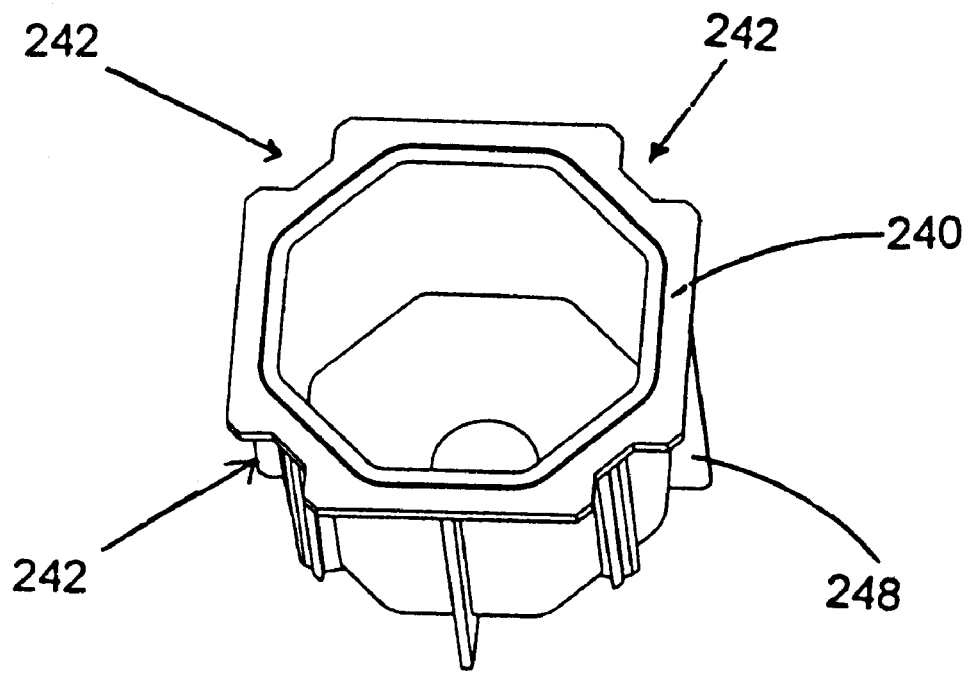
12B

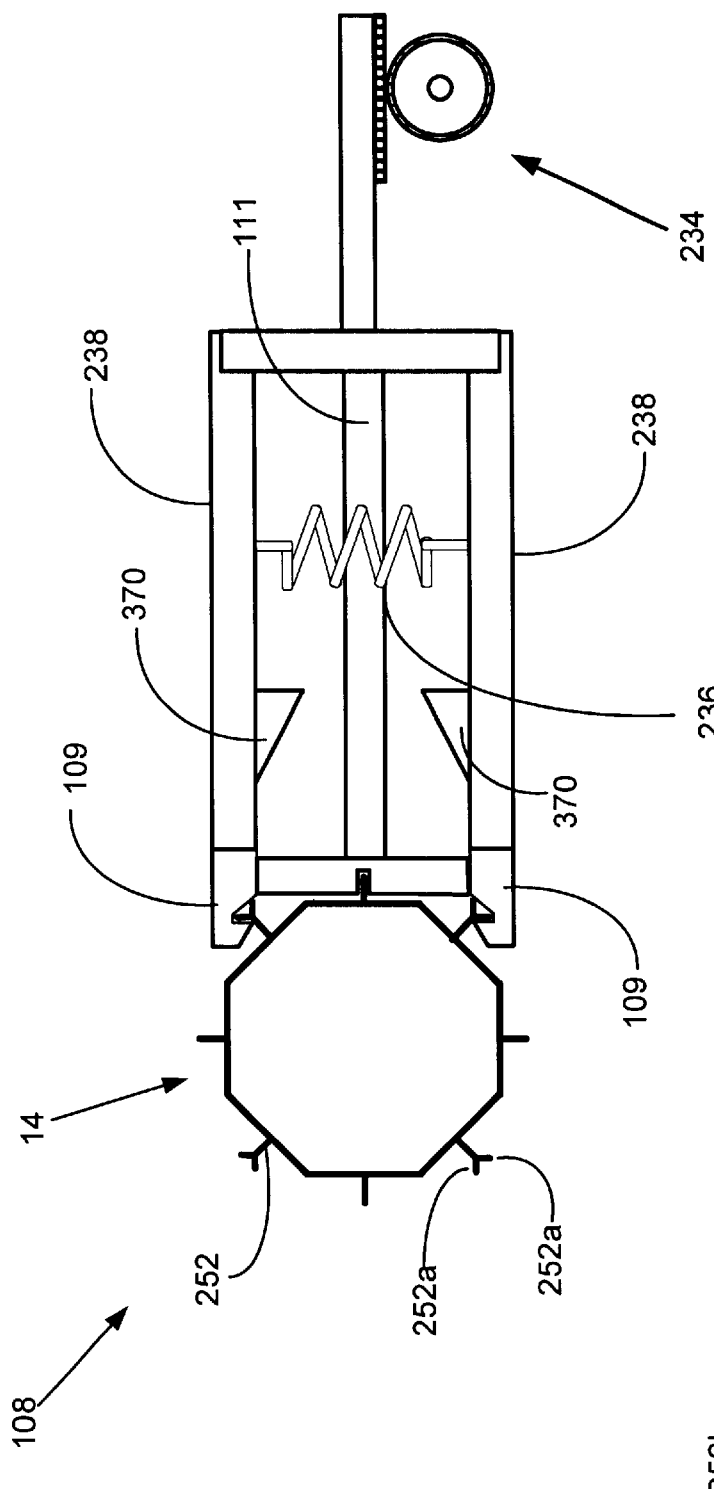
FIG. 21
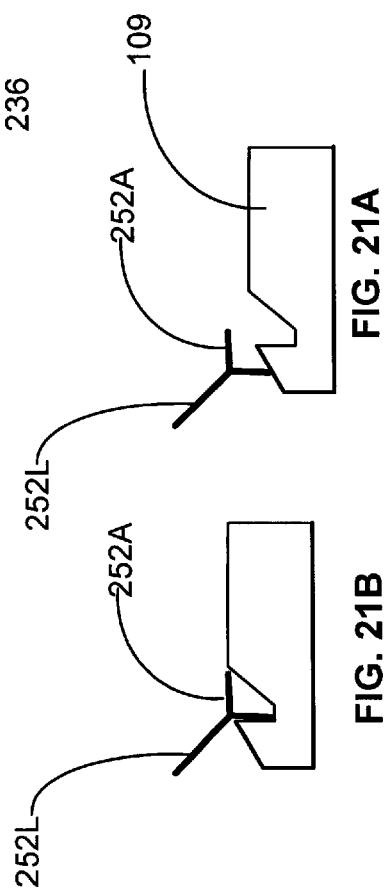
FIG. 21A
FIG. 21B

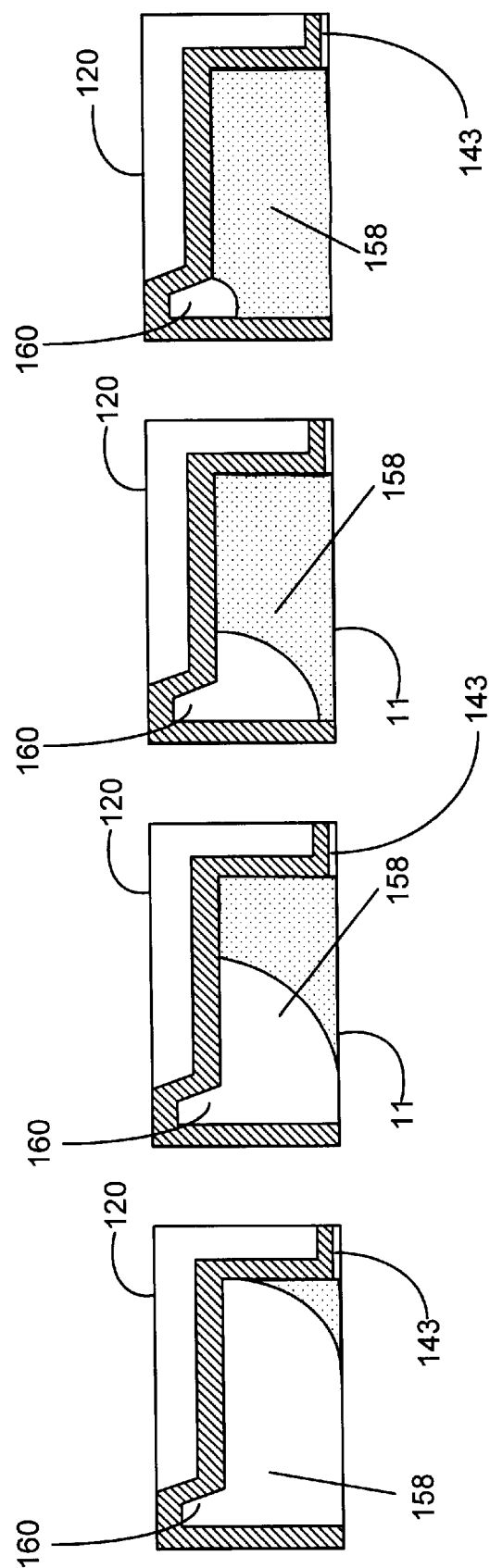

CANISTER FOR INVENTORYING SUSCEPTABILITY TEST DEVICES IN AN AUTOMATED MICROBIOLOGICAL ANALYZER

FIELD OF THE INVENTION

The present invention relates to a reagent container for use in an automated microbiological analyzer for determining an antibiotic effective in controlling growth of the microorganism. More particularly, the present invention provides an antibiotic reagent canister with features than enable automated handling of the reagent container as well as features than facilitate storage and secure dispensing of a reagent container from within a reagent canister maintained in an environmentally secure chamber on the analyzer.

BACKGROUND OF THE INVENTION

Various types of tests related to patient diagnosis and therapy can be performed by analysis of a biological sample. Biological samples containing the patient's microorganisms are taken from a patient's infections, bodily fluids or abscesses and are typically placed in test panels or arrays, combined with various reagents, incubated, and analyzed to aid in treatment of the patient. Automated biochemical analyzers have been developed to meet the needs of health care facilities and other institutions to facilitate analysis of patient samples and to improve the accuracy and reliability of assay results when compared to analysis using manual operations. However, with ever changing bacterial genera and newly discovered antibiotics, the demand for biochemical testing has increased in both complexity and in volume. Additionally, commercial analyzers typically require a user to employ a test panel having predetermined assay types thereon regardless of whether or not all of the predetermined assay types have been requested by a physician. Because of these greater demands in conjunction with the expense and scarcity of floor space within health care institutions and the pressure to provide clinical results at lower costs, it has become important to randomly perform different types of biochemical tests within a highly automated and compact analyzer that operates at high through-put with minimal clinician attention.

An important family of automated microbiological analyzers function as a diagnostic tool for determining both the identity of an infecting microorganism and of an antibiotic effective in controlling growth of the microorganism. In performing these tests, identification and in vitro antimicrobic susceptibility patterns of microorganisms isolated from biological samples are ascertained. Such analyzers have historically placed a small sample to be tested into a plurality of small sample test wells in panels or arrays that typically contain different enzyme substrates or antimicrobics in serial dilutions. Identification (ID) of microorganisms and of Minimum Inhibitory Concentrations (MIC) of an antibiotic effective against the microorganism are determined by color changes, fluorescence changes, or the degree of cloudiness (turbidity) in the sample test wells created in the arrays. By examining the signal patterns generated, both AST and ID measurements and subsequent analysis are performed by computer controlled microbiological analyzers to provide advantages in reproducibility, reduction in processing time, avoidance of transcription errors and standardization for all tests run in the laboratory.

In ID testing of a microorganism, a standardized dilution of the patient's microorganism sample, known as an inoculum, is first prepared in order to provide a bacterial or cellular suspension having a predetermined known concentration. This inoculum is placed in an analytical test array or panel having a number of microwells or alternately into a cuvette rotor assembly having an inoculum receiving well from where sample is distributed by centrifugal force to a number of test wells or chambers at the periphery of the rotor. The test. wells contain predetermined identification media consisting of enzyme substrates and/or growth inhibitors, which, depending on the species of microorganism present, will exhibit color changes, increases in turbidity or changes in fluorescence after incubation. For instance, a bacterial genera may be identified on the basis of pH changes, its ability to utilize different carbon compounds, or growth in the presence of antimicrobial agents in a test well. Some tests require addition of reagents to detect products of bacterial metabolism while others are self-indicating. In conventional chromogenic panels, the inoculum is incubated some 18–24 hours before analysis is completed. Alternately, microorganism ID may be accomplished using rapid fluorogenic test arrays employing growth-independent means in which preformed enzyme substrates are placed in the test wells and fluorogenic tests based on the detection of hydrolysis of fluorogenic substrates, pH changes following substrate utilization, production of specific metabolic substrates and the rate of production of specific metabolic byproducts are made after about 2 hours of incubation. In both cases, by examining the reaction of the inoculum and reagents after incubation and over a period of time, or lack thereof, and comparing that reaction with that of known species, the types of microorganisms can be identified. Importantly, a large number of different substrates or other reagents must be available in ID testing of an unknown microorganism because the microorganism will be more or less different sensitive to different substrates and reagents. In an automated analyzer, this is achieved by providing a variety of ID test panels, each pre-loaded with substrates and reagents that are selected to produce a known pattern of measurable reaction signals for various microorganisms.

The use of microbiological test trays and the techniques employed in MIC tests, also known as antibiotic susceptibility testing, AST, of microorganisms are also well known. AST tests are essentially broth dilution susceptibility tests using wells filled with inoculum and a growth broth, called herein a inoculum-broth solution, and increasing concentrations of a number of different antibiotics, or antimicrobial agents as used in different AST tests to determine which antimicrobial agents are most effective against a particular microorganism. The different antimicrobial agents are typically diluted in Mueller-Hinton broth with calcium and magnesium in chromogenic panels or diluted in autoclaved water with a fluorogenic compound in fluorogenic panels. The antimicrobials are diluted to concentrations that include those of clinical interest. After incubation, the turbidity or fluorescence will be less or non-existent in wells where growth has been inhibited by the antimicrobics in those wells. The analyzer compares each test well reading with a threshold value. The threshold value is a fixed number corresponding to a certain percentage of relative absorbency or fluorescence which corresponds to clinically significant growth. The MIC of each antimicrobial agent is measured either directly as visible growth, or indirectly as an increase in fluorescence.

Important challenges that must be taken into consideration when designing cost-effective, automated biochemical analyzers include the volume of reagents required per test and the cost of the disposable test panel, array or, in certain designs, a centrifugal test rotor. Because they are small and may be produced using mass-production, plastic injection molding techniques, it is advantageous to use very small sized, test arrays having a number of microwells for performing AST tests in order to facilitate automatic handling and minimize the expense of a disposable test array. AST test arrays typically consist of a plurality of adjacent microwells aligned in some sort of an array that function as reaction vessels for the above mentioned biochemical reactions involving a solid phase media and a liquid phase containing a sample to be tested. An aliquot of the sample is placed in each microwell along with appropriate antibiotic reagents. AST testing usually requires that the test trays be incubated at a controlled temperature for a period of time so that an observable reaction between the sample and reagent occurs; at predetermined time intervals, each microwell of the test tray is examined for an indication of changes in color change, turbidity, or size.

Filling a number of AST microwells with the required inoculum and/or reagents to perform AST tests with a wide variety of antibiotics presents several technical challenges that are made increasingly difficult as the number of the available antibiotics is increased. Efforts have been made to address these challenges along with other problems and these generally employ a vacuum technique in filling microwells within a test array via an interconnected number of micro-sized channels connected between the microwells and an inoculum reservoir.

Similarly, providing a number of ID test devices with the required substrates and/or reagents to perform ID tests to identify a wide variety of microorganisms presents technical challenges that are made increasingly difficult as the number of the available ID substrates and/or reagents is increased. Centrifugal ID test rotors like those used in the present invention typically consist of a plurality of test microwells that function as reaction vessels or microwells arrayed near the periphery of a generally flat disk. A centrifugally activated microwell filling process is employed as the ID test rotor has a large number of micro-sized channels radially connecting the test microwells to a supply reservoir near the center of the rotor. Test samples are placed within the supply reservoir and moved by centrifugal force through the microchannels to the test microwells which have been pre-loaded with appropriate biochemical reagents. The ID test rotor is generally incubated at a controlled temperature for a period of time to cause an observable reaction between the sample and reagents. At predetermined time intervals, each microwell of the ID rotor is examined for an indication of changes in color change, turbidity, or other observable reaction result. The pattern of changes may then be compared with reaction signal patterns of known microorganisms enabling the identification of the any microorganism within the sample, as discussed above.

There are conventional devices that carry out multi-step analytical procedures in an automated or semi-automated fashion. For example, microbiological analytical systems currently carry out automated antimicrobic susceptibility testing procedures using both photometric and fluorometric detection methods. The MicroScan Division of Dade Behring Inc. sells a device of this type under the trade designation WalkAway® analyzer. Armes et al. U.S. Pat. No. 4,676,951 and Hanaway U.S. Pat. Nos. 4,643,879 and 4,681,741 describe certain features the WalkAway® analyzer. Prior commercial embodiments of the WalkAway system analyze trays carrying microbiologic specimens. The system includes an enclosed incubation chamber for the specimens. The system adds reagents to the specimens and analyzes them. All these activities take place within the incubation chamber. Automated features of more recent microbiological testing machines are well known in the art, having been described in the following patents from which it may be seen that functions such as automated handling and transport of test devices like panels and rotors throughout an analyzer are well known. Those skilled in the art have a variety of well-known techniques and choices for the routine tasks of reagent and sample handling, test device transport, vacuum loading, incubation, optical testing, computer control, etc., as described in the patent below.

U.S. Pat. No. 6,096,272 discloses a diagnostic microbiological testing system and method for microorganism identification (ID) and antimicrobial susceptibility determinations (AST). The system includes multiple-well test panels capable of performing ID and AST testing on the same test panel. Each test panel is inoculated with reagents, broth-suspended organisms, and placed into the instrument system. The instrument system includes a rotating carousel for incubation and indexing, multiple light sources each emitting different wavelength light, colorimetric and fluorometric detection, barcode test panel tracking and a control processor for making determinations based on measured test data.

U.S. Pat. No. 6,086,824 discloses an automatic sample testing machine for testing samples stored in test cards. The test sample cards are placed in a tray and a transport station transports the tray from the incubation station to an optical reading station, where the cards are removed from the tray and optical measurements (e.g., transmittance and/or fluorescence optical testing) are conducted on test wells within the card. The machine has a sample loading station where test samples are placed in fluid communication with test cards in the trays.

U.S. Pat. No. 5,965,090 provides an automatic sample testing machine for testing samples stored in test cards. The machine has a test sample positioning system for moving a tray containing a plurality of test sample cards and fluid receptacles among various stations in the machine. The machine has a diluting station for adding a predetermined quantity of diluent to the receptacles. A pipetting station transfers fluid from one receptacle to another. A vacuum filling station has a vacuum chamber which cooperates with the tray to make a seal with the top surface of the tray. When vacuum is released from the chamber, the fluid samples are loaded into the cards from the receptacles. A test card transport station transports the test cards from an incubation station to an optical reading station, where transmittance and fluorescence optical testing is conducted.

U.S. Pat. No. 5,922,593 discloses a microbiological test panel assembly used in microorganism identification (ID) and antimicrobial susceptibility determinations (AST) testing is provided. The microbiological test panel assembly includes a plurality of test wells segregated into two sections. The test wells of each section are adapted to receive reagents capable of causing reactions used in performing ID and AST testing. The reagents enter the respective sections through fill ports and flow down a passageway of the test panel assembly in a serpentine manner filling all the test wells.

U.S. Pat. No. 5,888,455 discloses an analyzer having a sample card transport station that moves a test sample card from an incubation station to a transmittance and fluorescence optical station. The transport station has a drive belt and an associated stepper motor to move the card to the optical stations. The fluorescence station has a linear flash lamp that illuminates a column of the wells of the cards simultaneously. A reference detector and dichromatic beam splitter are used to ensure that the fluorescence measurements are independent of lamp output changes over time.

U.S. Pat. No. 5,863,754 discloses a process for bacteria identification and for determining the sensitivity of bacteria to antibiotics, and an apparatus and measuring supports for carrying out this process. A given volume of bacterial colony is introduced into a primary receiver and is dispersed within a liquid to form a precalibrated inoculum. This inoculum is moved between the primary receiver and one or more measuring supports so that the transferred quantities of bacteria correspond to the quantities required for the analyses to be carried out. Measurements are taken on the content of the compartments during or at the end of one or more incubations and are processed in order to characterize the growth of the bacteria present in the inoculum, to identify them and/or to determine their sensitivity to various antibiotics.

U.S. Pat. No. 5,807,523 discloses an automatic chemistry analyzer using nephelometric and turbimetric analyzers to analyze parameters within liquid samples in a medical testing laboratory. The analysis machine also includes an onboard control sample so that the machine can be programmed to periodically calibrate its analyzing equipment during the course of normal operation. The machine also includes a sample station carousel having retainer clips for retaining a sample container rack which is constructed to retain a bar-coded card containing information regarding reagents used in the machine. A bar code reader located proximate to the sample carousel reads the bar-coded reagent information into the controller.

U.S. Pat. No. 5,762,873 discloses an automatic sample testing machine for testing samples stored in test cards. The machine has a test sample positioning system for moving a tray containing a plurality of test sample cards and fluid receptacles among various stations in the machine. The machine has a diluting station for adding a predetermined quantity of diluent to the receptacles as needed. A pipetting station transfers fluid from one receptacle to another. A vacuum station is provided having a vacuum chamber moveable relative to the tray between upper and lower positions. The chamber cooperates with the tray to make a sealing engagement with the top surface of the tray when it is lowered to the lower position. A vacuum generator supplies vacuum to the chamber. When the vacuum is released from the chamber, the fluid samples are loaded into the cards from the receptacles. The test sample positioning system moves the tray to a cutting and sealing station and then to an incubation station and loads the cards one at a time into a carousel within the incubation station. A test card transport station transports the test cards from the incubation station to an optical reading station, where optical measurements are conducted on the wells of the card. When the card has been read, it is either moved back to the incubation station for additional incubation and reading or transferred to a card disposal system.

U.S. Pat. No. 5,670,375 discloses a sample card transport station which moves a test sample card from an incubation station to a transmittance and fluorescence optical station in a sample testing machine. The sample card transport station has a drive belt and an associated stepper motor. The belt supports the card from one side of the card. A ledge having a card slot is disposed above the belt. The card is snugly received within the card slot, and supported from below by the drive belt and rollers for the belt. When the motor turns the belt, the belt grips the card and slides the card along the slot to the optical stations, without slippage between the belt and the card.

U.S. Pat. No. 5,627,041 discloses a rotary cartridge adapted to present a biological sample to an imaging instrument for analysis by. The cartridge utilizes a series of channels, capillaries, reservoirs and stop junctions to move a sample, reagent and diluent through the cartridge as a function of the sum of capillary, gravitational and low centrifugal forces acting thereon.

U.S. Pat. No. 5,266,268 discloses a multi-well rotor which reduces tendencies of reagent or sample materials to spontaneously move or "wick" from one chamber compartment to another, resulting in premature co-mingling of reactants, and of sample or reagent material to flow out of one or more of the outer loading ports during acceleration of the rotor for transfer of the sample or reagent material from inner chambers to corresponding outer chambers.

U.S. Pat. No. 4,676,951 discloses an automatic system for analyzing microbiological specimens which have been treated and arranged in a plurality of specimen trays with each tray containing a plurality of specimens. Tray towers support a plurality of specimen trays. A work station selectively moves the trays one at a time from the tower to selectively deliver reagent or analyze the specimen in the tray. A control system is adapted to sequentially actuate the work station to properly sequence the system so that the reagents are administered to the respective specimen and the specimen is analyzed after a desired incubating period.

U.S. Pat. No. 4,448,534 discloses an apparatus for automatically scanning electronically each well of a multi-well tray containing liquid samples. A light beam is passed through the wells to an array of photosensitive cells, one for each well. There is also a calibrating or comparison cell for receiving the light beam. An electronic apparatus reads each cell in sequence, completing the scan without physical movement of any parts. The resultant signals are compared with the signal from the comparison cell and with other signals or stored data and determinations are made and displayed or printed out.

From this discussion of the art state in automated microbiological analyzers, it may be seen that current microbiological analyzers frequently employ multiple-well test panels capable of performing ID and AST testing on the same or separate different test panels. In particular, in the analyzer described in the family of patents related to U.S. Pat. No. 5,762,873 discussed above, prior to the start of a testing procedure, a technician loads a cassette with a plurality of test cards wherein the test cards come in two varieties: (1) identification cards, in which particular different growth media are placed in each of the wells of the card when the cards are manufactured, and (2) susceptibility cards, in which different concentrations of different antibiotics are placed in each of the wells of the card. In the analyzer described in U.S. Pat. No. 6,096,272, discussed above, a technician must inoculate a combination ID/AST test panel with an unknown microorganism and then place that panel into the analyzer where it is then incubated and analyzed periodically. From this it may be seen that prior to the use of the automated features of such state-of-the art microbiological analyzers, an operator is required to select the particular ID and/or AST test cards or devices that are required to perform the analyses called for by a physician and then either: (1) to inoculate and load the selected ID and/or AST test cards onto the analyzer, or (2) to load the selected ID and/or AST test cards onto the analyzer where the cards are automatically inoculated with test sample.

Hence, state-of-art analyzers require an operator to manually select test panels or rotors already preloaded with the particular substrates, growth media, reagents, etc., required to perform the ID and/or AST determinations that have been ordered by a physician from a hospital's supply resources and load them by hand onto an analyzer. Preloaded panels and rotors typically also include test wells with substrates, growth media, reagents for ID and/or AST determinations that have not been ordered by a physician, thereby introducing unnecessary waste. Thus, known analyzers do not provide the flexibility needed to provide a microbiological analyzer that is adapted to automatically select from an on-board inventory of test devices pre-loaded only with the substrates, growth media and/or reagents as required to perform only those specific ID and AST determinations ordered by a physician. There is thus an unmet need for a fully automated, high throughput microbiological analyzer having such capabilities flexibility built into the analyzer in order to minimize waste and operator involvement.

SUMMARY OF THE INVENTION

The present invention meets the foregoing needs by providing a fully automated random access microbiological test analyzer having the capability to select from among an inventory of different AST test arrays adapted for performing different AST tests, from among an inventory of broth containers adapted to provide different growth media as required for performing the different AST tests, and from among an inventory of different ID test rotors adapted for performing different ID tests and having the capability to also perform the desired ID and AST testing. Incoming patient samples to be tested are barcoded with identifying indicia from which the ID and AST tests that are desired to be performed by the analyzer may be determined by a computer programmed to appropriately operate the analyzer. An exemplary embodiment of the present invention is directed at a microbiological analyzer having a plurality of different AST test arrays housed in different rectangular AST canisters and the AST canisters are maintained on a first rotatable carousel. The different AST test arrays are pre-loaded with increasing concentrations of a number of different antibiotics, or antimicrobial agents. The analyzer is programmed to automatically select the numbers of different AST test arrays required to complete the requested AST protocols and load the AST test arrays onto an appropriate carrier for transportation to various incubation and testing stations. A plurality of different broth containers are housed in different tube-like broth canisters and the broth canisters are also maintained on the second rotatable carousel. The different broth containers are preloaded with a number of different broth solutions. Depending on the details of a particular AST testing protocol, the requisite broth containers are selected automatically by the analyzer, diluted with sample inoculum and mixed. An appropriate amount of inoculum-broth solution is then placed into each AST test device after the AST test devices have been loaded onto the AST carrier for transportation throughout the analyzer. The analyzer similarly has a plurality of different ID test rotors housed in different tube-like ID canister and the ID canisters are maintained on a second rotatable carousel. The different ID test rotors are preloaded with substrates and reagents that are selected to produce a known pattern of measurable reaction signals that correspond to various known microorganisms. The analyzer is programmed to automatically select the numbers of different ID test rotors required to complete the requested ID protocols and to load the ID test rotors onto an appropriate carrier for transportation to requisite sample loading, incubation and analysis stations with minimal clinician attention. In addition, the analyzer employs a high-speed, compact, in-line sample pipetting and delivery system that aspirates sample from open sample tubes and deposits sample aliquots as required into ID test rotors and broth containers and that also aspirates sample-broth mixtures from broth containers and places such mixtures into AST test arrays.

The present invention provides a inventory canister with features than enable automated handling of the AST test arrays as well as features than facilitate storage and dispensing from within a canister maintained in an environmentally secure chamber on the just described automated, random access microbiological test analyzer. The present invention specifically provides an elongate AST canister having a generally rectangular cross-section with two AST canister flat sides and two AST canister narrow sides, the flat side being about 10 times greater in dimension than the narrow side. AST canister is sized to house a plurality of AST test arrays stacked one atop another and maintained secure by pairs of AST canister internal ribs extending along the elongate height of AST canister flat sides as the test arrays are within the environmentally controlled AST inventory chamber. Key features of the AST canister include an AST canister cylindrical pivot shaped to seat into a mating dock within inventory chamber to allow the AST canister to be rotated using an AST canister handle to a vertical position where an AST canister seating flange fits into a vertical groove in AST canister post. AST canister seating flange extends the full length of AST canister narrow side except for a small AST canister alignment key and alignment notch provided to confirm proper orientation of AST canister with a corresponding slot for key and stop for notch within the vertical groove in AST canister post. AST canister also comprises an AST canister eject port formed in the AST canister narrow side proximate AST canister cylindrical pivot and sized to allow the lowermost AST test array within the plurality of AST test arrays stacked one atop another to be pushed out of AST canister. AST test arrays may be pushed out of AST canister using a plunger entering canister through an AST canister plunger port that is aligned with AST canister eject port and is formed in the AST canister narrow side opposing AST canister eject port. A pair of inwardly projecting dimples are formed in AST canister flat sides and extend into AST canister eject port to retain AST test arrays within AST canister, preventing accidental dislodging of a AST test array from canister and also to prevent AST test arrays from being improperly inserted back into canister.

BRIEF DESCRIPTION OF THE DRAWINGS

These and other features and advantages of the present invention can best be understood by reference to the detailed description of the preferred embodiments set forth below taken with the drawings in which:

FIGS. 12A and 12B are perspective views of the broth container of FIG. 11;

FIG. 21 is a view of an broth container handling apparatus useful within the present invention;

FIGS. 21A and 21B are enlarged views of a portion of the broth container handling apparatus of FIG. 21;

DETAILED DESCRIPTION OF THE PREFERRED EMBODIMENTS

Figure 1:
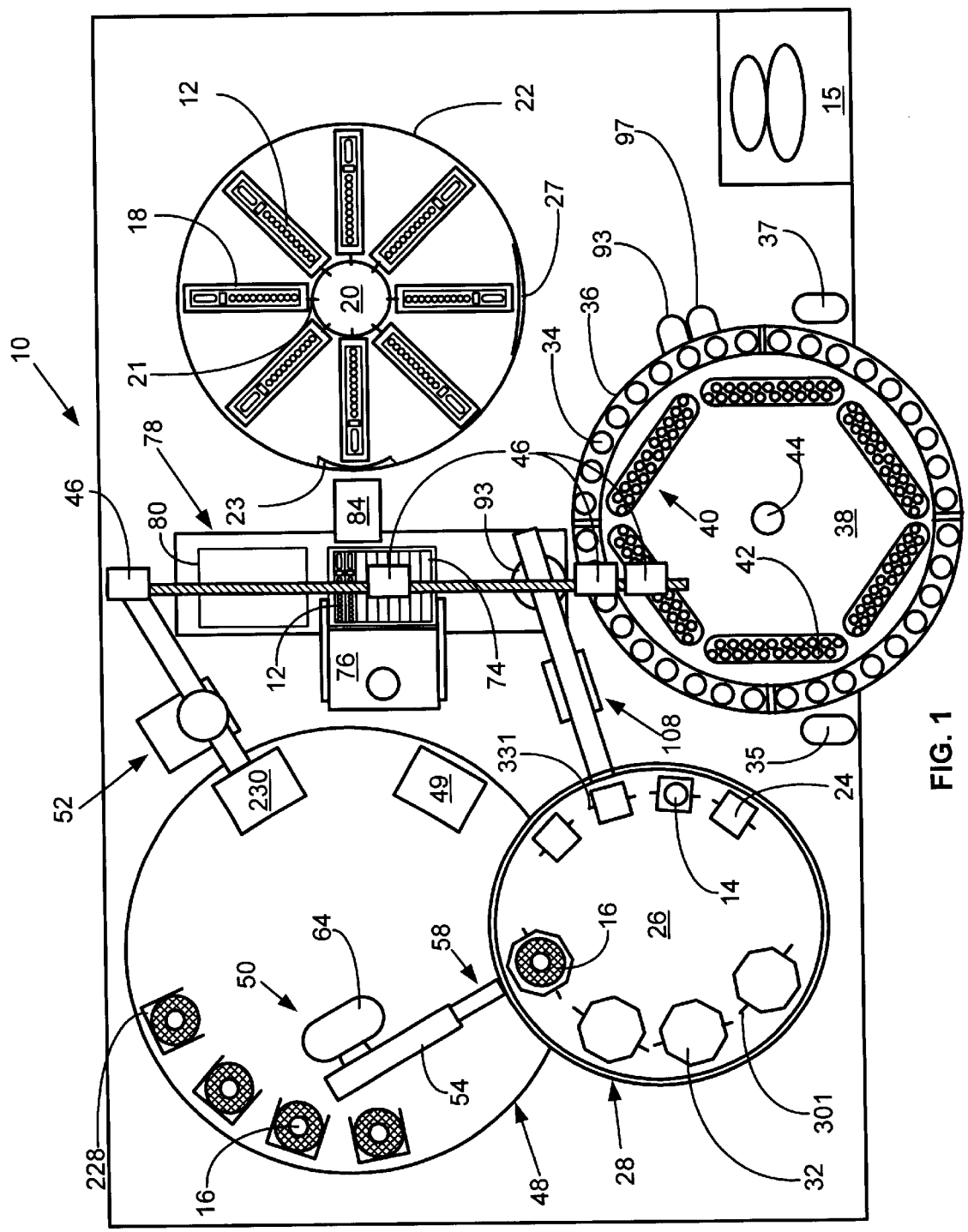
FIG. 1 is a simplified schematic plan view of an automated microbiological analyzer illustrative of the present invention.
Figure 2:
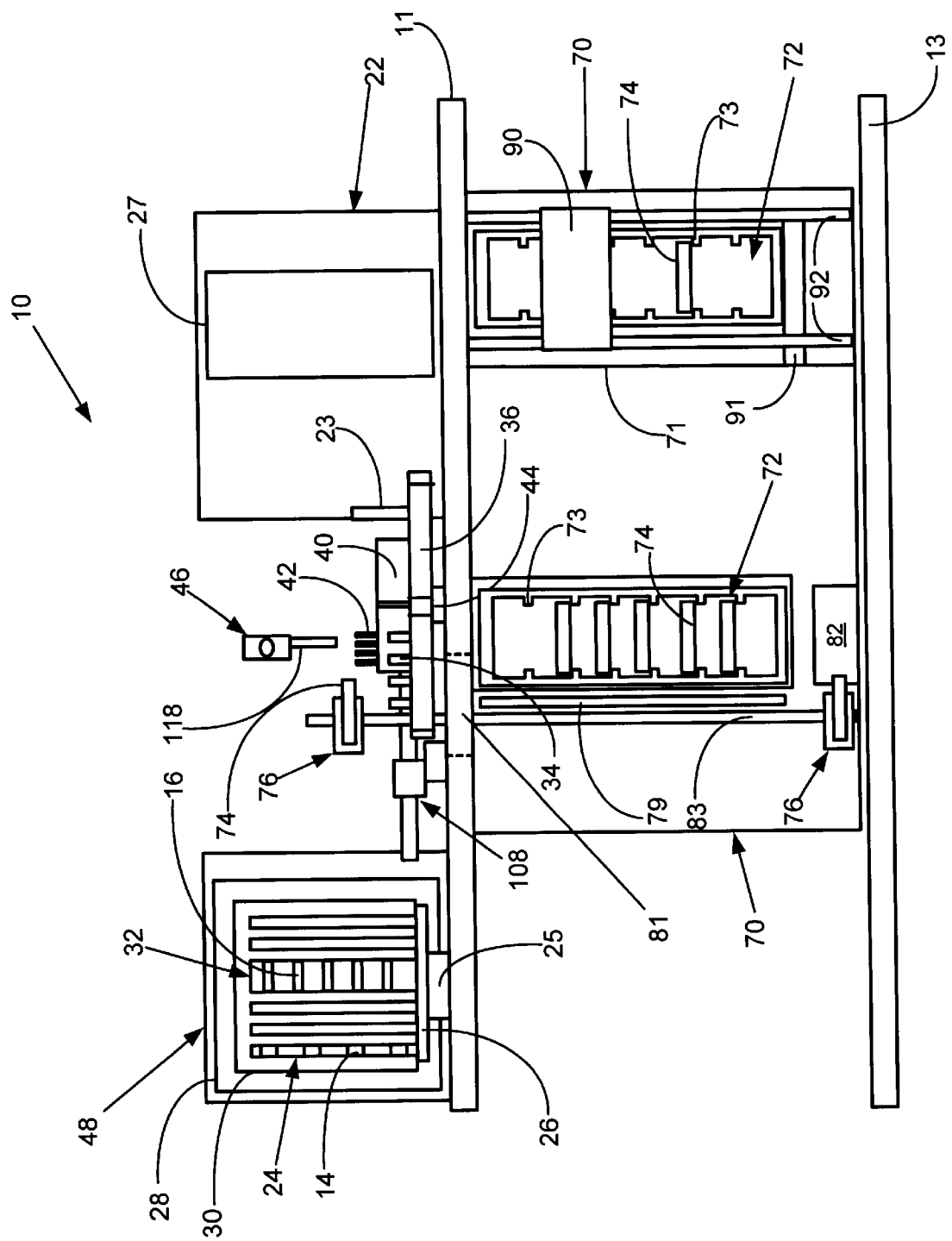
FIG. 2 is a simplified schematic elevation view of the automated microbiological analyzer of FIG. 1.

FIG. 1 schematically illustrates an embodiment of the automated random access microbiological analyzer 10 of the present invention, the analyzer 10 having an on-board inventory of AST test arrays 12 adapted for performing different AST tests, a plurality of broth containers 14 (also seen in FIG. 2) adapted to provide different growth media as may be required for AST testing, and a plurality of ID test rotors 16 adapted for performing different ID tests. The term "random access" indicates the ability to randomly select any number of different AST test arrays 12, different broth containers 14, and different ID test rotors 16 as required for microbiological testing. The inventory of different AST test arrays 12 are maintained within analyzer 10 in different rectangularity elongate AST test array canisters 18. The AST canisters 18 are attached to a rotatable post 20, hereinafter called the AST canister post 20; the AST canister post 20, AST canisters 18 and AST test arrays 12 are housed within an environmentally controlled AST inventory chamber 22 (top portion is removed for purposes of illustration in FIG. 1). The different AST test arrays 12 are preloaded with increasing concentrations of a number of different antibiotics, or antimicrobial agents as required, to perform AST testing on a patient sample, also called inoculum herein, as requested by a physician. In FIG. 2, the AST inventory chamber 22 is shown with a first door 23 or seal 23 provided to allow operating access to any one of the AST canisters 18 when AST canisters 18 are rotated by AST canister post 20 into alignment with an AST array dispenser 84 described later. The AST inventory chamber 22 also has a second door 27 to allow the AST canisters 18 to be mounted onto AST canister post 20 by an operator. In a exemplary embodiment, as many as seventy-five AST test arrays 12 would be contained within each AST canister 18, described later in FIG. 7, and as many as seventy-five AST canisters 18 would be housed within the AST inventory chamber 22.

The plurality of different broth cups or containers 14 (FIG. 2, left side) are maintained in an on-board inventory within analyzer 10 in different tube-like broth canisters 24, FIG. 14, and the broth canisters 24 are maintained on a rotatable carousel 26, hereinafter called the B/ID carousel 26, the B/ID carousel 26 being housed within an environmentally controlled B/ID chamber 28 (shown with its top portion removed for purposes of illustration). A rotating motor 25 is operated as required to rotate the B/ID carousel 26 so as to present a required broth canister 24 and broth container 14 to a broth container handling device described later. The different broth containers 14 are preloaded with a number of different standard broth solutions that act as a growth media during AST testing. In FIG. 2, the B/ID chamber 28 is shown with a door 30 in an opened position to allow operating access to the inside of the B/ID chamber 28. The broth canisters 24 are shown as being made of a transparent material or as cut-away in order to shown four broth containers 14 contained within the broth canisters 24. In a exemplary embodiment, as many as twenty broth containers 14 would be contained within each broth canister 24 and as many as fourteen broth canisters 24 would be housed within the B/ID chamber 28. An important feature of analyzer 10 is a magnetic mixing member within each broth container 14 and an associated vortex mixer 93, both described later, provided so as to properly mix patient sample disposed into broth containers 14 with broth solution contained within broth containers 14.

In a similar manner, the analyzer 10 has an on-board inventory of different ID test rotors 16 described hereinafter, FIG. 8, that are maintained in an inventory within analyzer 10 in different tube-like ID canisters 32, FIG. 10, and the ID canisters 32 are maintained along with broth canisters 24 on the B/ID carousel 26 within B/ID chamber 28. The different ID test rotors 16 are preloaded with substrates and reagents that are selected to produce a known pattern of measurable reaction signals which correspond to various known microorganisms. Motor 25 is also operated as required to rotate the B/ID carousel 26 so as to present a required ID canister 32 and ID test rotor 16 to a rotor handling device described later. In an exemplary embodiment, as many as eighty ID test rotors 16 would be contained within each ID canister 32 and as many as four ID canisters 32 would be housed upon the B/ID carousel 26.

Patient samples are presented to the analyzer 10 in open sample tubes 34 placed in openings in a number of sample tube holders 36 located near the periphery of a rotatable circular tray, known hereinafter as S/PT tray 38, rotatable by a S/PT tray motor 44. Sample tube holders 36 are generally curved, each forming a sector of the circumference of a circle. Four of such sample tube holders 36 are seen in FIG. 1 supported on rotatable tray 38, however any number of sample tube holders 36 may be sized and adapted to fit onto the circular tray 38. Conventional bar-code readers 35 are placed proximate sample tube holders 36 so as to determine the identity of sample tubes 34 and a turbidity reader 37 is similarly placed so as to confirm that the concentration of microbiological organisms within sample tubes 34 is within a predetermined range of acceptable values. An important feature of analyzer 10 is a magnetic mixing member within each sample tube 34 and an associated vortex mixer 93, both described later, provided so as to properly mix patient sample contained in sample tubes 34 before turbidity reader 37 is employed. A sensor (not shown) to detect the presence of magnetic mixing member within each sample tube 34 is optionally provided proximate S/PT tray 38 to ensure the presence of such a magnetic mixing member. A sample dilution station 97 is also located proximate S/PT tray 38 and is adapted to dilute sample contained in sample tubes 34 if the concentration of microorganisms in sample liquid carried within tubes 34 is determined by turbidity reader 37 to be higher than an allowable range.

The S/PT tray 38 also supports a number of pipette tip holders 40 located in the innermost portion of S/PT tray 38. Pipette tip holders 40 are generally elongate and may have a curved shape and each pipette tip holder 40 is adapted to hold a plurality of disposable pipette tips 42. Six of such pipette tip holders 40 are seen in FIG. 1, however any number of pipette tip holders 40 may be sized and adapted to fit onto the S/PT tray 38. The S/PT tray 38 may be rotated by motor 44 so as to present any of the pipette tips 42 and any of the open sample tubes 34 to a pipetting apparatus 46. The pipetting apparatus 46 is adapted to remove one of the pipette tips 42 from pipette tip holder 40, to insert the pipette tip 42 into an open sample tube 34, and to aspirate a known amount of patient sample from the sample tube 34 into the pipette tip 42. The pipetting apparatus 46 is further adapted to dispense a known amount of patient sample from pipette tip 42 into a broth container 14 or ID test rotor 16, as described hereinafter.

S/PT tray 38, pipetting apparatus 46, B/ID chamber 28, AST inventory chamber 22, and ID incubation and testing chamber 48 are supported above an upper operating plate 11 that provides a first operating plane for analyzer 10. A lower base plate 13, typically mounted on rollers, provides a second operating plane for additional structure for analyzer 10.

Figure 16:
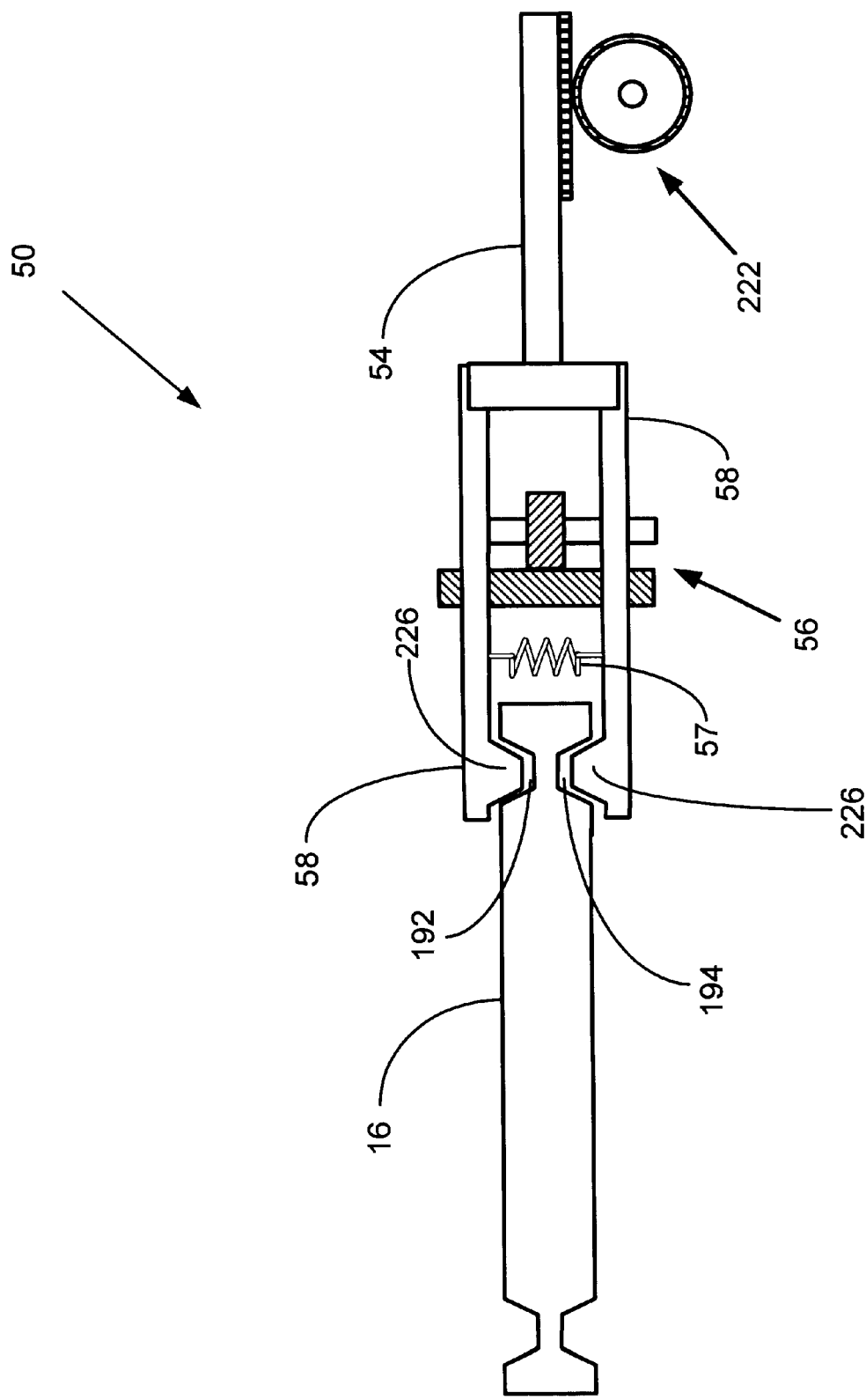
FIG. 16 is a side elevation view of an ID rotor robotic device useful within the present invention.

Analyzer 10 comprises two separate incubation and analysis chambers as required for ID and AST testing. An ID incubation and analysis chamber 48 is seen in the top plan schematic view of FIG. 1 with its uppermost surface removed to expose an interior portion in which an ID robotic device 50, also seen in FIG. 16, is adapted to remove different ID test rotors 16 from ID canisters 32 and to then move the ID test rotors 16 to and from an ID rotor filling and centrifuging apparatus 52, described later, moveable between the ID incubation chamber 48 and a sample pipetting and delivery system 60 described hereinafter and illustrated in FIG. 3. ID robotic device 50 comprises a robotic arm 54 that carries a gear-driven mechanism 56 that activates a pair of claw-like gripping pincer-teeth 58 at an end of arm 54. Pincer-teeth 58 are sized and spaced to grip gripping troughs 192 and 194 in rotor 16, described hereinafter, thereby to move a lowermost ID rotor 16 from ID canister 32 to centrifuging apparatus 52 when centrifuging apparatus 52 is positioned within the ID incubation and analysis chamber 48. A vertically translatable rotation motor system 64 provides vertical and rotational motion to robotic arm 54 so that ID rotors 16 may positioned throughout all of the interior of incubation and analysis chamber 48. Devices that perform the functions of robotic device 50 are well known in the art as computer-controlled pick-and-place robotic devices.

In FIG. 2, an AST incubation and analysis chamber 70 is seen located below the operating plate 11 with a first side surface portion 71 opened to reveal. an interior section in which a number of rotatable AST incubation racks 72 support a number of AST carriers 74, FIG. 17, the AST carriers 74 being adapted as described hereinafter to hold a number of AST test arrays 12 as they are transported throughout analyzer 10. An AST carrier transporter 76, FIG. 18, is mounted on a vertically oriented AST transport rod 83 and is adapted to be moveable from above the upper operating plate 11 to above the lower base plate 13. The AST carrier transporter 76 is shown in uppermost and lowermost positions in FIG. 2 for purposes of explanation even though there is only one such AST carrier transporter 76. In the uppermost position above the operating plate 11, as best seen in FIG. 1, the AST carrier transporter 76 can access an AST array carrier 74 transported on an AST carrier transport 78 described hereinafter and lower the AST array carrier 74 through an AST transport opening 81 in the operating plate 11. In the lowermost position, AST carrier transporter 76 is adapted to deposit an AST array carrier 74 into an AST vacuum filling station 82 positioned on the lower base plate 13 and described hereinafter. For purposes of simplicity in illustration, chambers 48 and 70 are shown as being separate; however in an exemplary embodiment of the present invention, AST incubation and analysis chamber 70 and ID incubation and analysis chamber 48 share a common environmentally controlled space with the only opening to the external environment being between AST carrier transporter 76 and an AST array dispenser 84 described later.

The AST carrier transporter 76 is further adapted to be vertically moveable from between the vacuum filling station 82 on the lower base plate 13 and the uppermost AST incubation ledge 73 within AST incubation and analysis chamber 70. The AST carrier transporter 76 is further adapted to remove an AST array carrier 74 from the vacuum filling station 82 and to deposit the AST array carrier 74 on any one of the pairs of AST incubation ledges 73 within any of the AST incubation racks 72 inside AST incubation and analysis chamber 70. A opened second side portion 79 is formed in the exterior wall of the AST incubation and analysis chamber 70 to facilitate transfer from the AST carrier transporter 76 to the AST incubation racks 72.

An AST array dispenser 84 is seen in FIG. 1 as being disposed between the AST chamber 22 and AST array carrier 74. The AST array dispenser 84 is adapted to remove a AST test arrays 12 from AST canisters 18 in the form of a singulated stream and to successively place the AST array 12 within empty AST array slots 86 formed within an AST array carrier 74 (FIG. 17). AST array dispenser 84, FIG. 19, comprises an ejection means 368 operable with an alignment means 360 and a biasing means 362 to precisely align and eject the lowermost AST test array 12 from any one of the vertically oriented AST canisters 18 into an empty parallel slot 86 when slot 86 is aligned by AST carrier transport 78 with the elongate dimension of a first AST test array 12 having therein the antibiotics as required to perform a first AST test ordered by a physician. Subsequent to loading of the first AST test array 12 into the first parallel slot 86, AST carrier transport 78 indexes the AST array carrier 74 stepwise relative to the AST array dispenser 84 so as to align a second empty parallel slot 86 in AST array carrier 74 with a second AST canister 18 containing the AST test arrays 12 having therein the antibiotics as required to perform a second AST test ordered by a physician. As described previously, a plurality of different AST test arrays 12 are maintained within analyzer 10 in different AST canisters 18 attached to a rotatable AST canister post 20. Simultaneously with the AST array carrier 74 being moved relative to the AST array dispenser 84, the AST canister post 20 is rotated to present to AST array dispenser 84 another of the AST canisters 18 housing the particular AST test arrays 12 preloaded with the appropriate antibiotics required to perform another AST test ordered by a physician.

Figure 20:
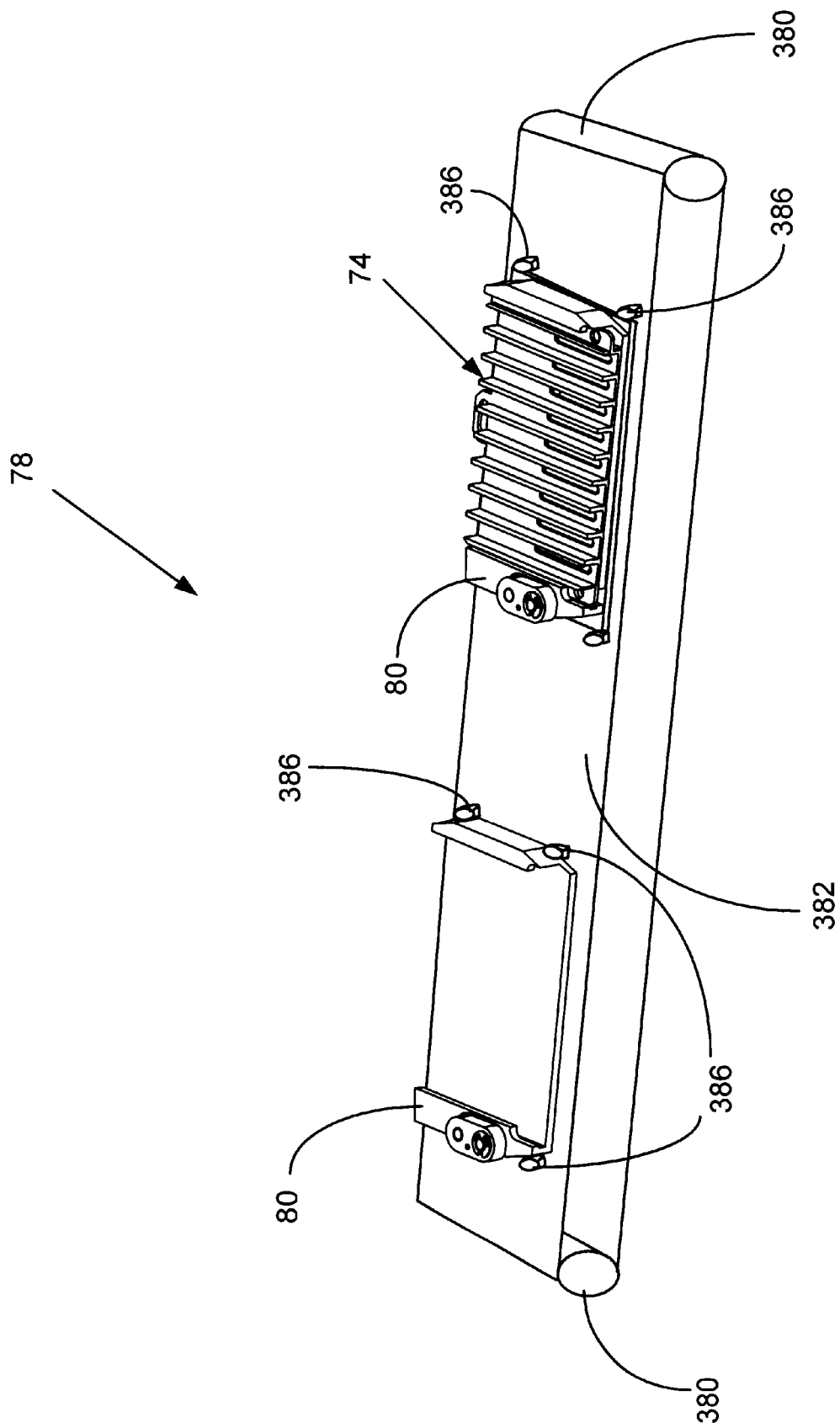
FIG. 20 is a view of an AST carrier transport useful within the present invention.

AST array dispenser 84 is then operated to push the lowermost AST test array 12 within second canister 18 into the second empty parallel slot 86 in AST array carrier 74. AST array dispenser 84 continues this operation in conjunction with rotation of AST canister post 20 until the number of different AST test arrays 12 as are required to perform all of the different AST tests ordered by a physician have been loaded onto AST carriers 74. AST carrier transport 78 comprises a translatable belt, lead-screw or similar mechanism as illustrated in FIG. 20 adapted to securely support and move AST carrier beds 80 supporting AST carriers 74 as described later over the operating plate 11 in a linear path below pipetting apparatus 46. Incoming patient samples are bar-coded with identifying indicia from which the AST tests that are desired to be accomplished may be established by CPU 15. Analyzer 10 of the present invention thus provides random access to any one of a number of different AST tests because of the inventory of different AST test arrays 12 contained within different AST canisters 18 housed within the AST chamber 22.

In an exemplary embodiment, as many as ten AST incubation racks 72 may be contained within the AST incubation and analysis chamber 70 and as many as twenty AST carriers 74 may be supported on pairs of ledges 73 in each AST incubation rack 72. The uppermost pair of ledges is reserved for used AST carriers 74 to be transferred to a disposal (not shown). An AST array reader 90 is positioned within AST incubation chamber 70 proximate the periphery of the AST incubation racks 72 and is adapted to remove a single AST array carrier 74 from an AST incubation rack 72 and to perform AST optical analysis on samples contained within the AST test arrays 12 carried by AST array carrier 74. After AST optical analysis is completed, AST array reader 90 is similarly adapted to return the AST array carrier 74 to its original position within the AST incubation rack 72. The AST reader 90 is mounted on a pair of vertically oriented shafts 92 and is moveable between the next-uppermost and lowermost AST array carrier 74 within AST incubation chamber 70 so that all AST carriers 74 within AST incubation and analysis chamber 70 may be removed from all AST incubation racks 72 for testing. Each AST incubation rack 72 is attached to a rotatable platen 91 so that all AST carriers 74 may be presented as required for optical analysis to the AST reader 90.

U.S. Pat. No. 4,448,534, assigned to the assignee of the present invention, describes a scanning apparatus for performing optical density tests on liquid samples that is typical of the AST reader 90 used in analyzer 10. The apparatus of the prior patent includes an optical testing system for automatically electronically scanning each well of a multi-well test device containing several different liquid samples. Two beams of interrogating radiation from are passed through a plurality of AST test wells arrayed in two concentric circles as described later to an opposing array of photosensitive cells, one photosensitive cell for each test well. The intensity of the beam of interrogating radiation may be monitored and the associated power source adjusted using feed-back mechanisms so as to maintain a stable intensity level. There is optionally also provided a calibrating or comparison test well for receiving the radiation. Electronic apparatus read the optical signals emanating from each test well in sequence completing a scan of all test wells in the array as the test array is passed between the radiation source and the array of photosensitive cells. The resultant signals are compared with the signals from a comparison cell and with other signals or stored data, and AST determinations are made and then recorded within CPU 15 and displayed or printed out. A system of the type described above is similar to that sold under the trademarks Walk-Away® analyzer by Dade Behring Inc., Deerfield, Ill.

Figure 17:
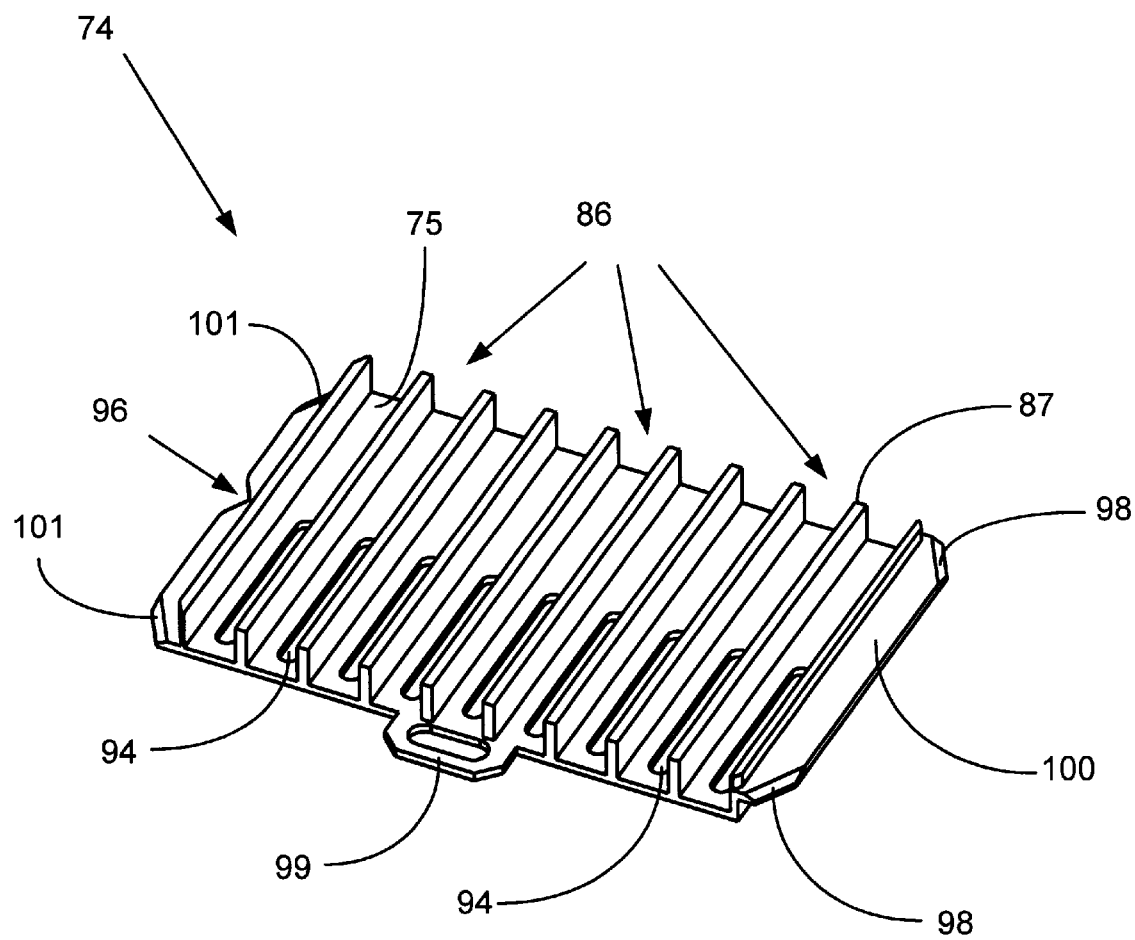
FIG. 17 is a perspective view of an AST array carrier useful within the present invention.
Figure 18:
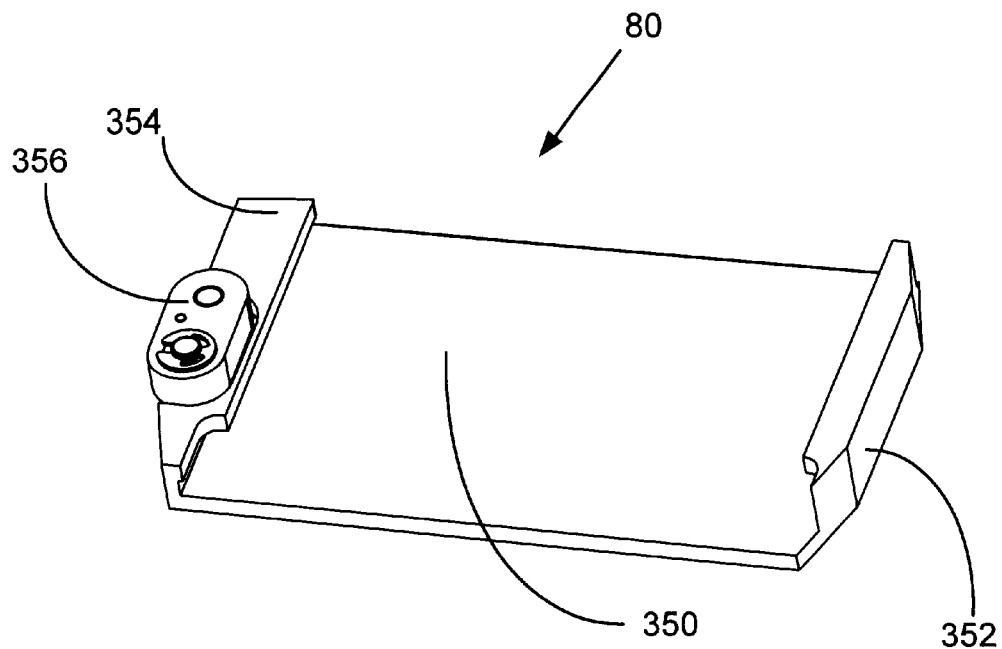
FIG. 18 is a perspective view of an AST carrier transport useful within the present invention.

As seen in FIG. 17, AST array carrier 74 is formed with a number of individual parallel open slots 86, each slot 86 having an elongate optical reader opening 94 formed in the carrier base 75 of the carrier 74 to facilitate optical measurements as described above. Reader openings 94 are sized and shaped so as to allow the interrogating beam of radiation to be passed through the plurality of microwells in a AST test array 12 described hereinafter. AST array carrier 74 further includes a notch 96 and chamfered edges 101 formed in the base 75 of carrier 74 and a pair of chamfered edges 98 formed in a raised flange 100 to facilitate secure transportation of the AST array carrier 74 throughout analyzer 10. Additionally, these features, notch 96 and chamfered edges 98 and 101, are used in precisely transferring and locating a carrier 74 for optical analysis by a biasing means at notch 96 adapted to urge the carrier 74 against a stop mated with the raised flange 100. Slots 86 are defined by a number of rails 87 extending upwardly from carrier base 75 and such rails 87 serve to maintain AST test arrays 12 in a stable and secure position within AST array carrier 74. An important feature of AST array carrier 74 is a handle 99 formed in base 75 to facilitate movement of AST array carrier 74 to and from AST carrier bed 80, to and from AST carrier transporter 76, to and from AST incubation rack 72, to and from optical reader 90, to and from an AST vacuum filling station 82, and to and from an AST disposal station (not shown). FIG. 17 shows a typical arrangement of the various features on AST array carrier 74 that cooperate with AST carrier transport system 78 and AST carrier transporter 76 as the carriers 74 are securely and automatically moved within analyzer 10 in response to commands from CPU 15. AST carrier transporter 76 comprises a claw-like arm operated by CPU 15 so as to grasp an AST array carrier 74 using handle 99 and move the AST array carrier 74 within analyzer 10 as described above.

Figure 18A:
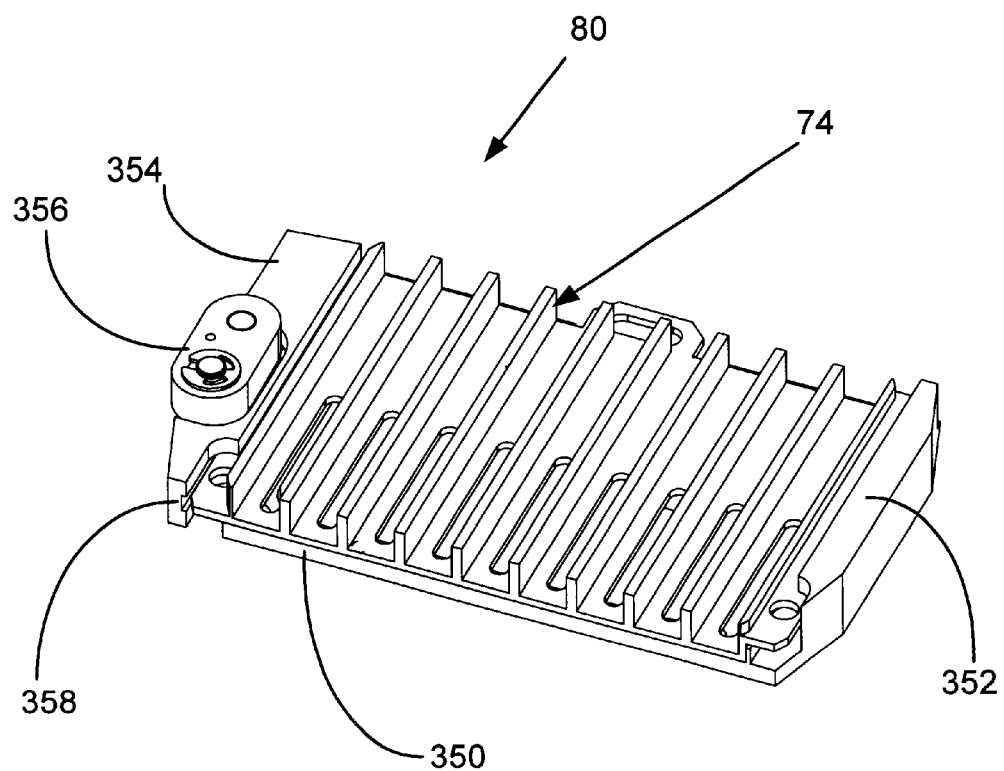
FIG. 18A is a perspective view of the AST array carrier of FIG. 17 nested within a AST carrier transport of FIG. 18 useful within the present invention.

FIG. 18 shows AST carrier bed 80 comprising a generally flat AST carrier transport base 350 sized to accept an AST array carrier 74 between a fixed AST carrier registration wall 352 and an AST carrier transport bias wall 354. AST carrier transport bias wall 354 supports a spring-loaded AST carrier detent 356 positioned to mate against notch 96 formed in the base 75 of AST array carrier 74 thereby to urge AST array carrier 74 securely against AST carrier registration wall 352. An AST carrier transport side wall groove 358 is formed in AST carrier transport bias wall 354 to enhance the security of AST array carrier 74 within AST carrier bed 80. FIG. 18A shows such an AST array carrier 74 nested within AST carrier bed 80 and retained therein by AST carrier detent 356.

Figure 3:
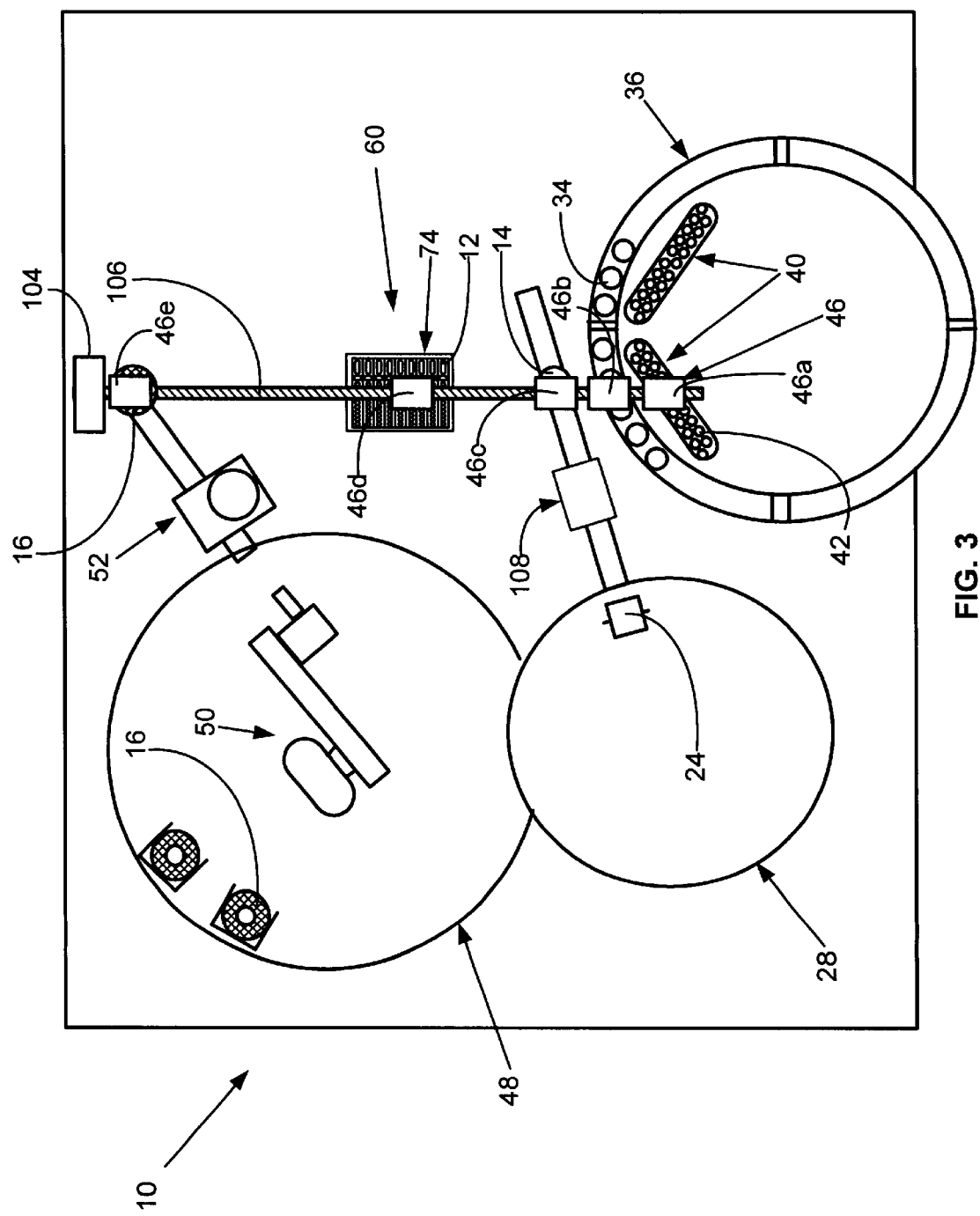
FIG. 3 is an simplified schematic plan view of a sample pipetting and delivery system useful within the analyzer of FIG. 1.

An important feature of the analyzer 10 is a multi-functional sample pipetting and delivery system 60 illustrated schematically in FIG. 3 in which only some of the features and elements of analyzer 10 are depicted for the sake of simplicity. Sample pipetting and delivery system 60 is adapted to remove a pipette tip 42 from a pipette tip holder 40 using a pipetting apparatus 46, aspirate a known quantity of liquid sample from an open sample tube 34 held in a sample tube holder 36 and to deposit a portion of or all of the aspirated sample into either of, or both of, a broth container 14 or an ID test rotor 16. Pipetting apparatus 46 is supported on a raised frame 102 (FIG. 4) and is adapted to be moved typically by a stepper motor 104 and lead screw 106 (FIG. 3) as controlled by CPU 15 between:

1. a first position, identified as 46a, for accessing pipette tips 42;
2. a second position, identified as 46b, for aspirating sample from sample tube 34;
3. a third position, identified as 46c, for depositing a known amount of sample into a broth container 14 and subsequently aspirating a known amount of mixed sample-broth solution from broth container 14;
4. a fourth position, identified as 46d, for depositing a known amount of mixed sample and broth into an AST test array 12;
5. and a fifth position, identified as 46e, for depositing a known amount of sample into an ID test rotor 16.

Sample pipetting and delivery system 60 is adapted to be moved in two opposed directions along a linear path defined by the loci L of positions 46a, 46b, 46c, 46d, and 46e. This feature of analyzer 10 simplifies movement of pipetting apparatus 46 between pipette tips 42 in pipette tip holder 40, sample tubes 34 in sample tube holder 36, broth containers 14, AST test arrays 12 within AST array carrier 74, and ID rotors 16 within filling and centrifuging apparatus 52. Positions 46a, 46b, 46c, and 46e are fixed position along loci L; however, as described in conjunction with FIG. 15, position 46d is a multiple number of locations whereat sample-broth solution is dispensed into a reservoir within AST arrays 12 to fill the arrays 12. The linear movement of pipetting apparatus 46 between operating position along loci L, the changing location of position 46d during AST array filling, taken in conjunction with an AST carrier 74 "build and fill" process described later advantageously reduces the amount of idle time needed for ID and AST testing by analyzer 10, thereby increasing throughput of analyzer 10.

Figure 4:
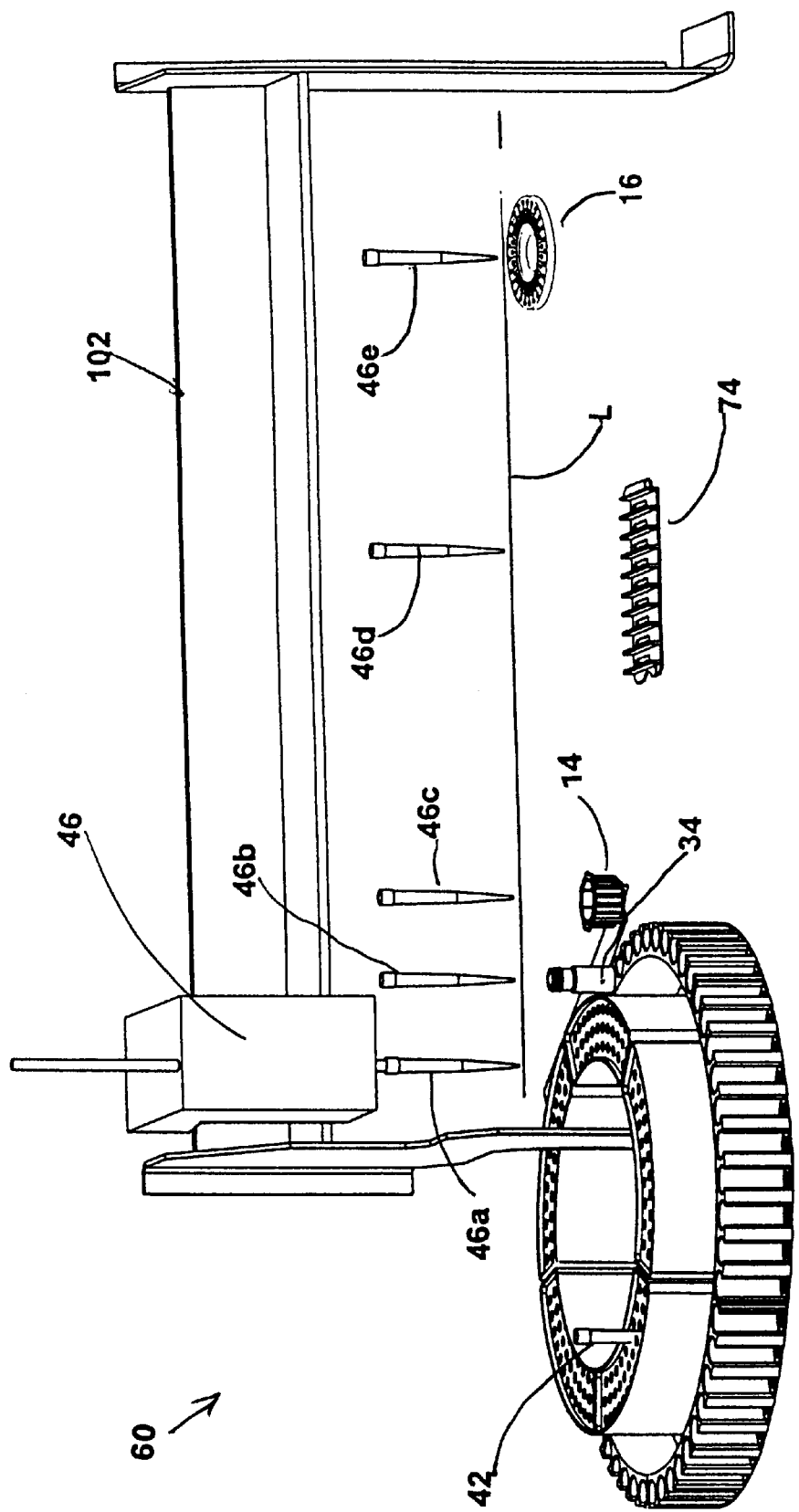
FIG. 4 is a perspective view of the pipetting and delivery system of FIG. 3.

FIG. 4 is a perspective view of the multi-functional liquid sample pipetting and delivery system 60 and shows the positional relationships between pipette tips 42 shown in position 46a, sample tubes 34 shown in position 46b, broth containers 14 shown in position 46c, AST array containers 74 shown in position 46d, an ID rotor 16 shown in position 46e.

Figure 22:
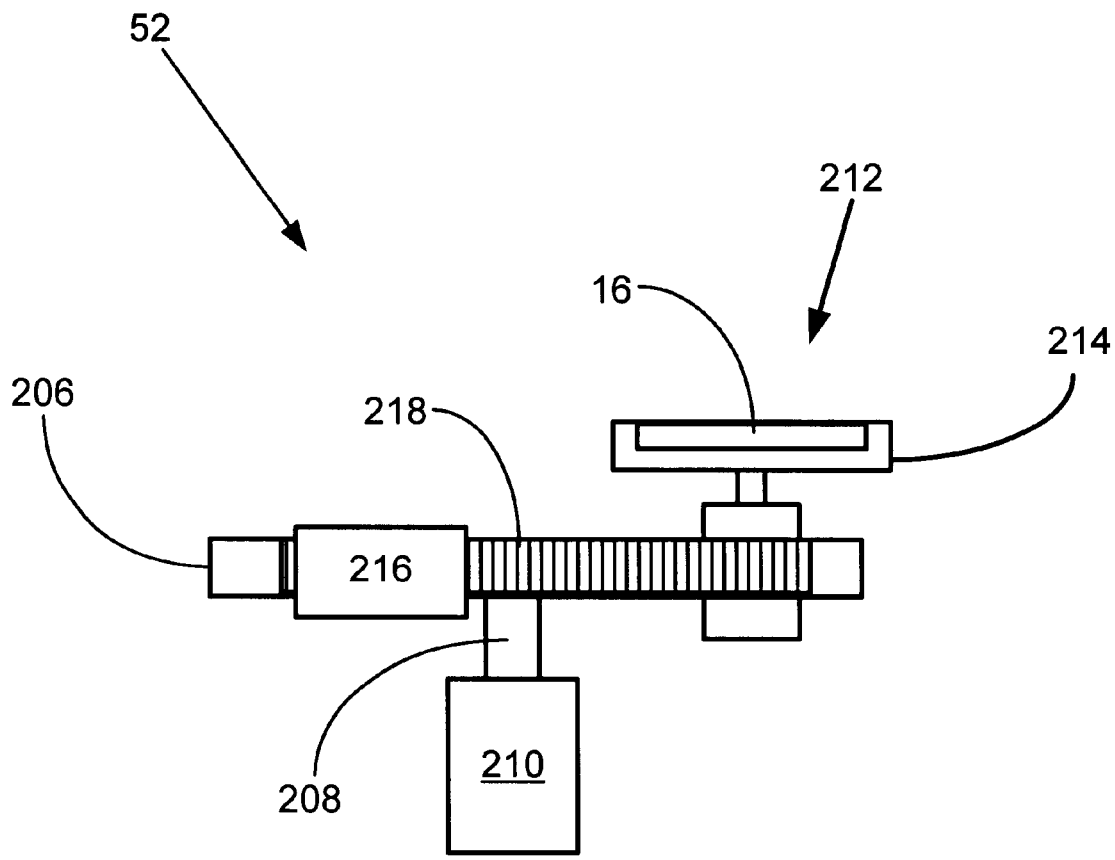
FIG. 22 is a view of an ID rotor filling and centrifuge device useful within the present invention.

The sample pipetting and delivery system 60 further comprises the previously mentioned pipetting apparatus 46, a broth container handling apparatus 108 seen in FIG. 21 and adapted to remove a broth container 14 from the B/ID carousel 28 and to present the broth container 14 to the pipetting apparatus 46, and an ID rotor filling and centrifuging apparatus 52 seen in FIG. 22 and adapted to remove an ID test rotor 16 from the ID incubation and analysis chamber 48 and present ID test rotor 16 to the pipetting apparatus 46. ID rotor filling and centrifuge device 52 is further adapted to replace an ID test rotor 16 back into the ID incubation chamber 48 after presentation to the pipetting apparatus 46. The ID rotor filling and centrifuge device 52 is even further adapted to centrifugally rotate an ID test rotor 16 so as to distribute sample deposited therein by the pipetting apparatus 46.

In conjunction with the ID rotor filling and centrifuge device 52, the broth container handling apparatus 108, rotatable S/PT tray 38, ID rotors 16 and AST arrays 12, sample pipetting and delivery system 60 is able to automatically provide rapid and random access within analyzer 10 to all patient samples to be tested for ID and AST characteristics, to all reagents necessary to perform such ID and AST tests, and to all sample handling or test devices necessary for such ID and AST tests, without requiring operator intervention.

Figure 23:
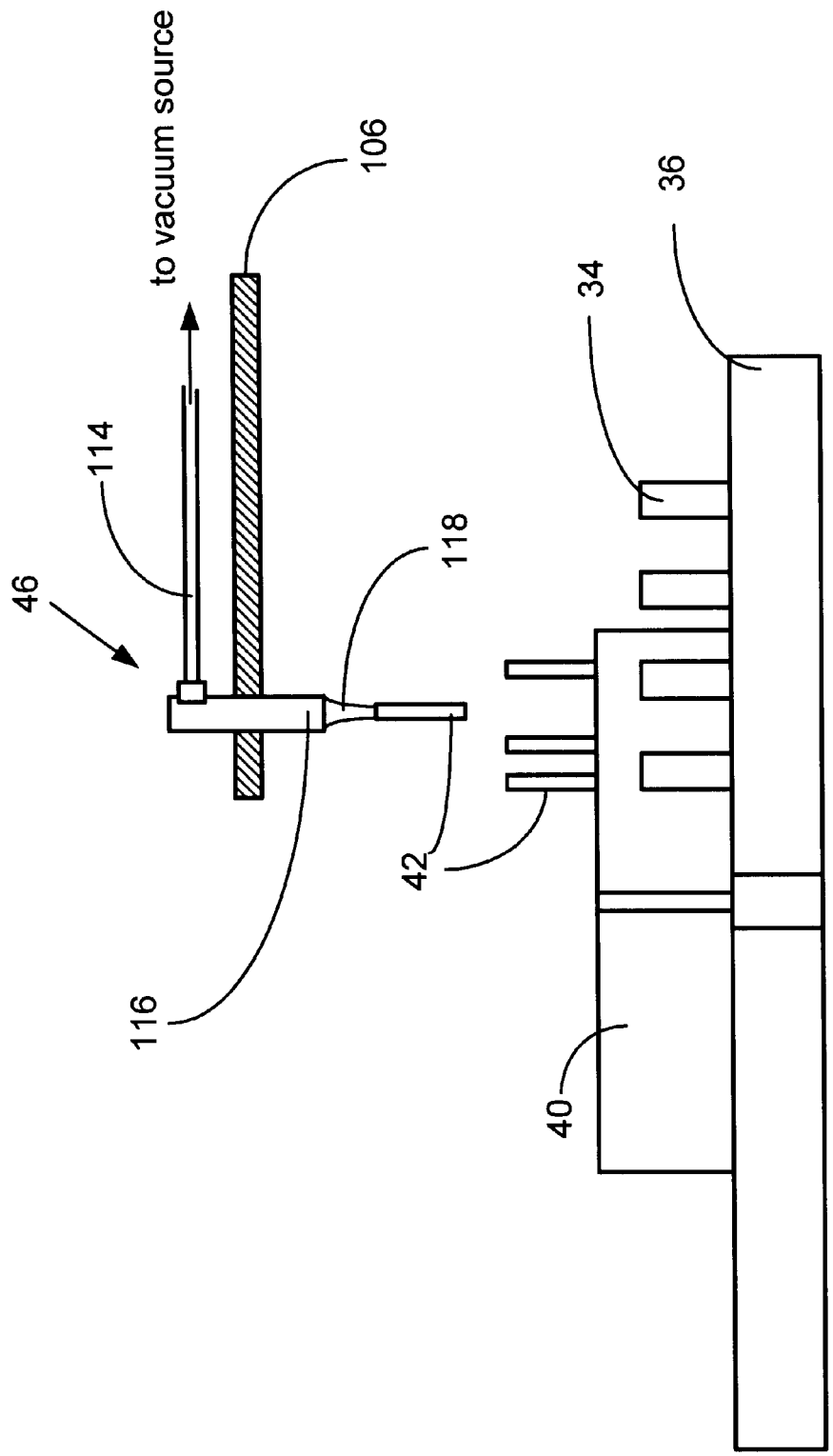
FIG. 23 is a side elevation view of a pipetting apparatus useful within the present invention; and, FIGS. 24A–P is illustrative of a liquid sample filling process using the AST test array of FIG. 5.

Devices adapted to perform the functions of pipetting apparatus 46, FIG. 23, are generally known and typically include stepper motor 104 (FIG. 3) and lead screw 106, a vacuum operated liquid sample aspiration/disposition system 114, and a vertical linear drive 116 having a tapered pipette tip mandrel 118 at its lower extremity, the mandrel 118 being sized for an interference fit into a pipette tip 42. Stepper motor 104 and lead screw 106 provide linear movement of the pipetting apparatus 46 along the path defined by positions 46a, 46b, 46c, 46d and 46e. Linear drive 116 provides vertical movement to a pipette tip 42 thereby to access the various liquid containers previously described. Pipetting apparatus 46 thereby provides means for aspiration of patient sample from a sample tube 34 and deposition of said sample into either of, or all of, a broth container 14, an ID rotor 16, and aspiration of mixed sample-broth solution from a broth container 14 and dispensing into an AST test array 12 carried by an AST carrier 74.

Figure 5:
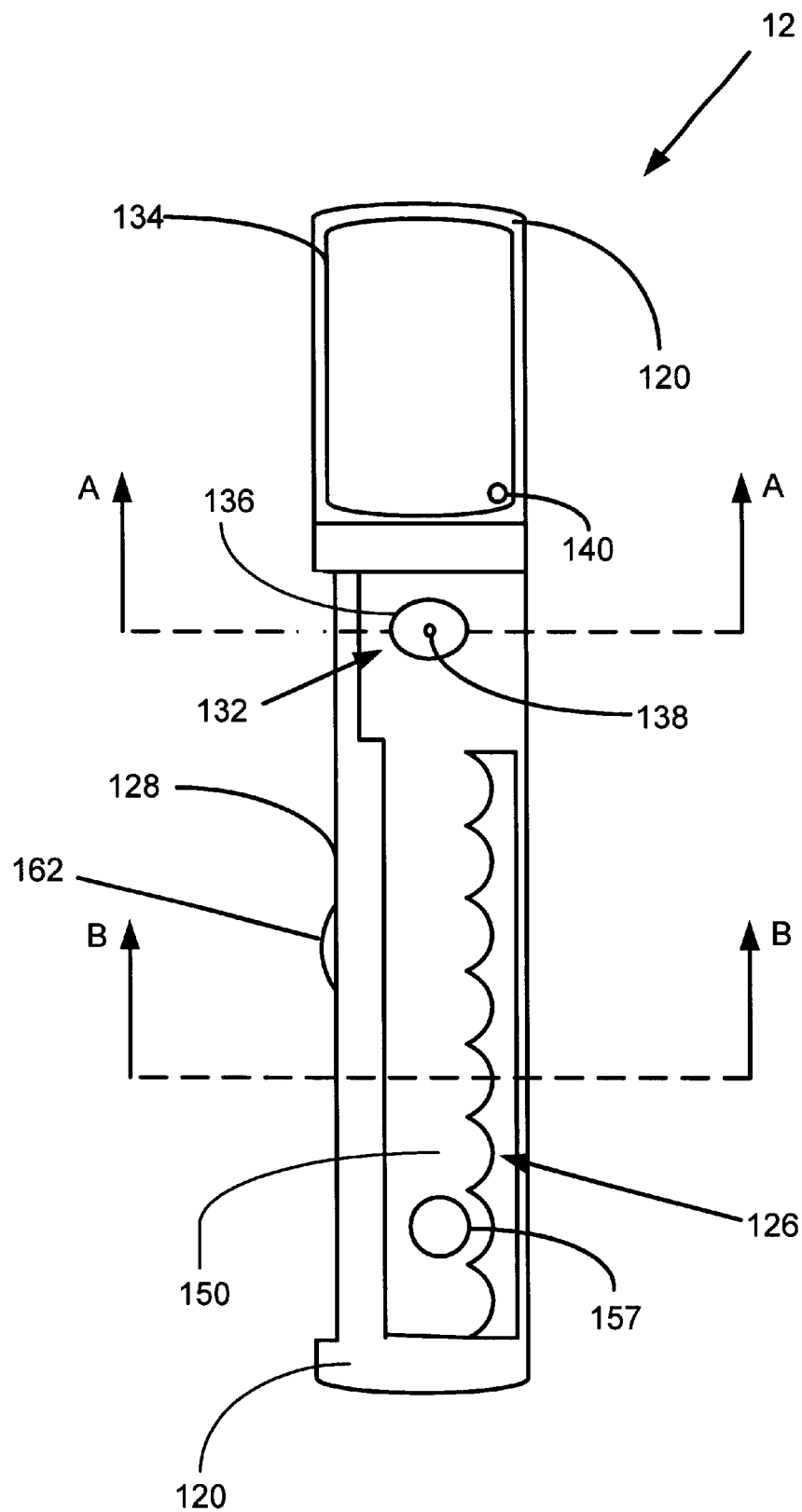
FIG. 5 is a top view of an AST test array useful within the present invention.
Figure 5A:
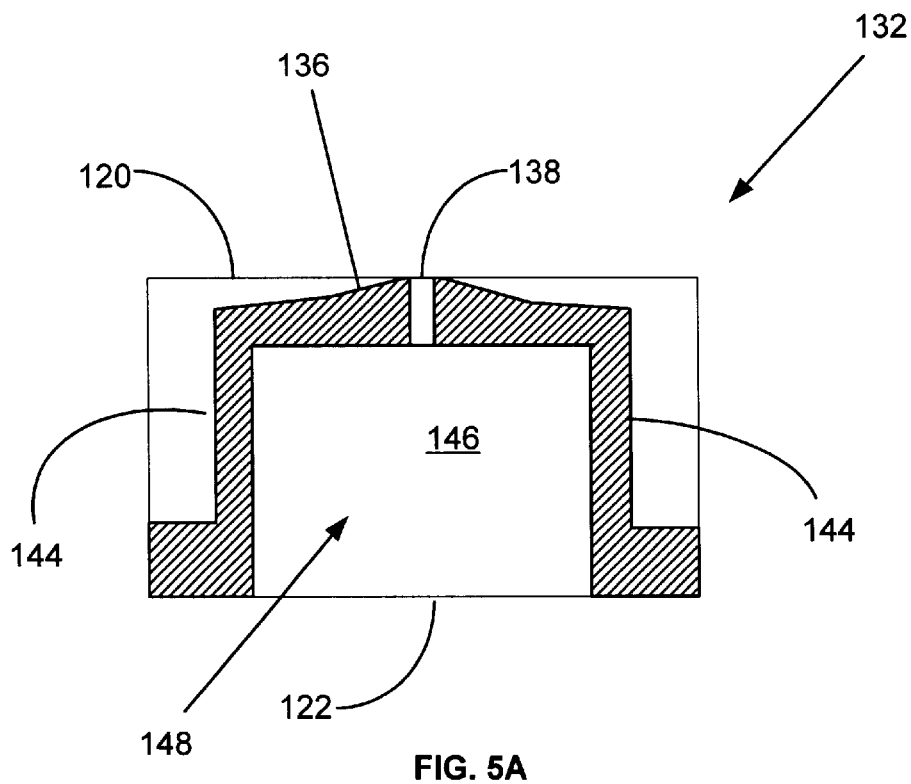
FIGS. 5A and 5B are cross-section views of the AST test array of FIG. 5.
Figure 5B:
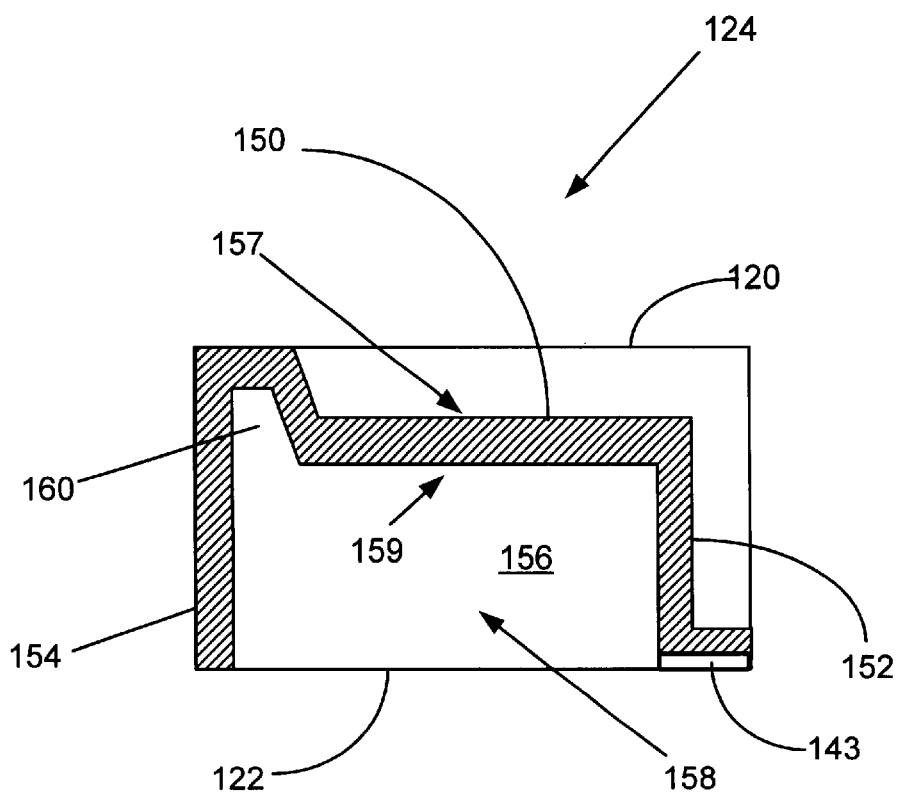
Figure 6:
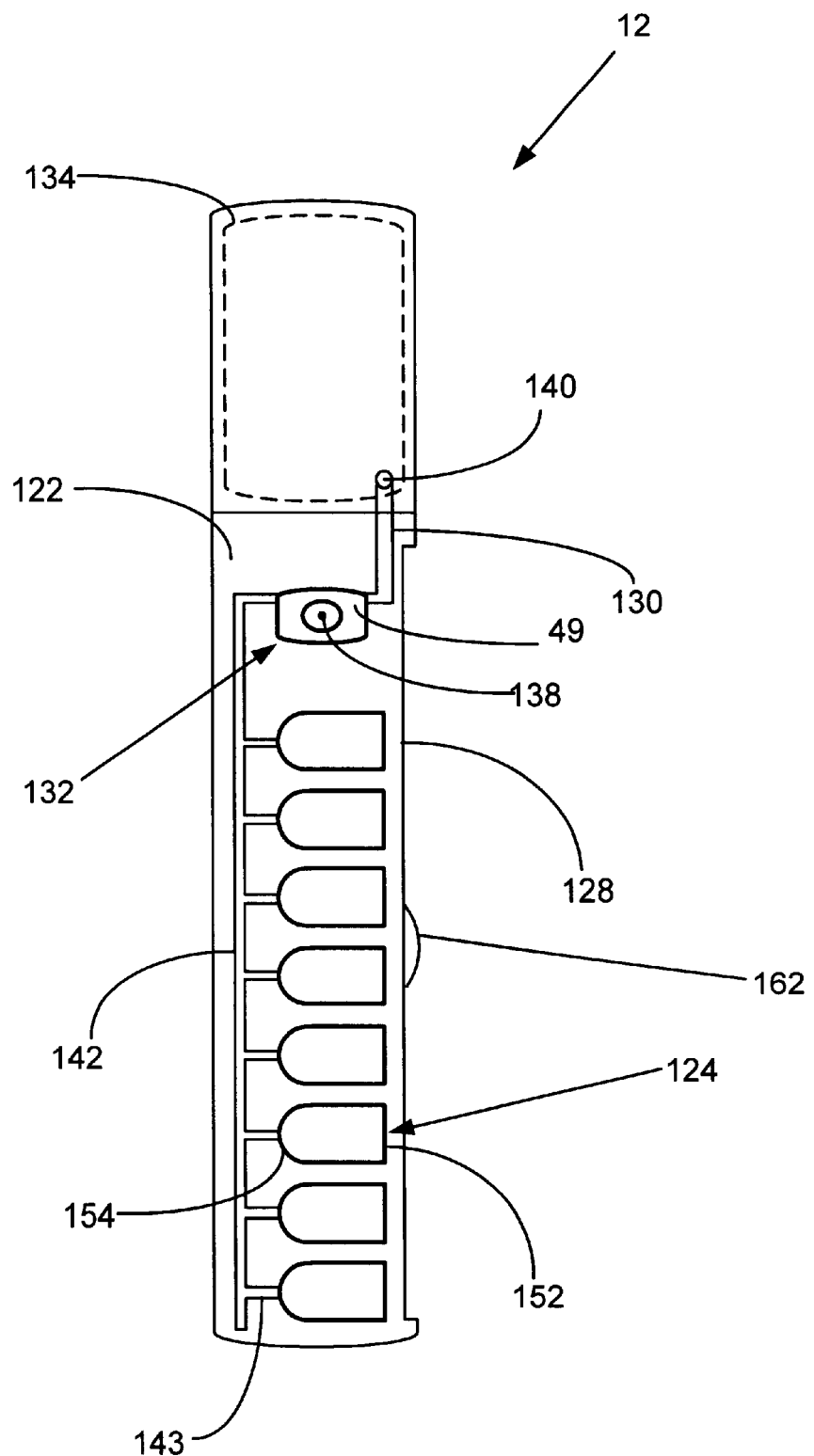
FIG. 6 is a bottom view of the AST test array of FIG. 5C.
Figure 6A:
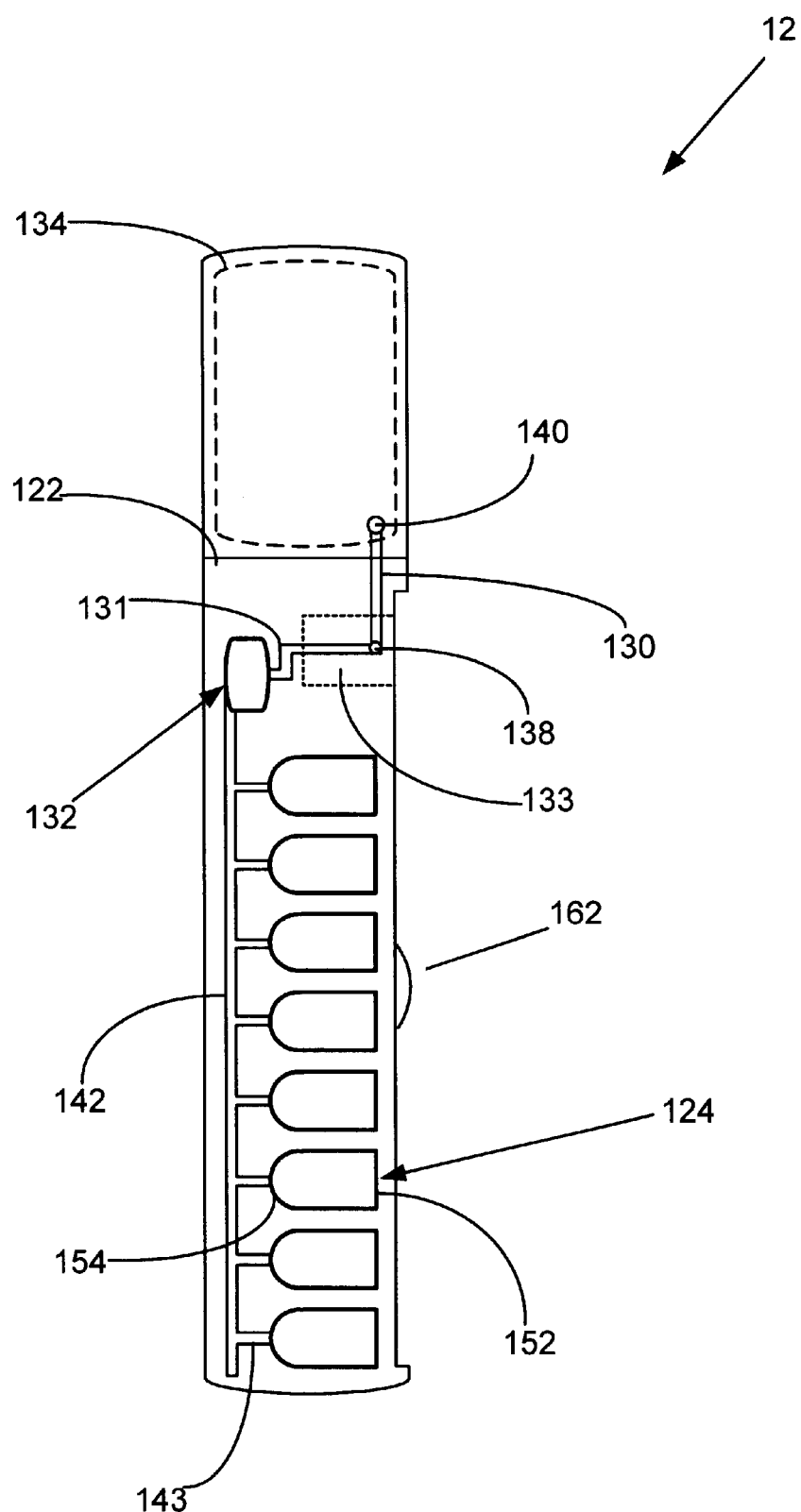
FIG. 6A is a bottom view of an AST test array useful within the present invention.

FIG. 5 shows the upper top surface 120 of an AST array 12 as containing relatively structured features described hereinafter and FIG. 6 shows the lower bottom surface 122 of an AST array 12 as being relatively flat. As described in a co-pending U.S. patent application Ser. No. 09/795,823, each AST array 12 has an elongate length and a plurality of upwardly projecting AST microwells 124 formed in the bottom surface 120 as a linear row of single microwells 124 parallel to the length of the array 12. Top surface 120 and bottom surface 122 are on opposing surfaces and are separated by an indented sidewall 126 and an opposed sidewall 128. A sacrificial evaporation well 132 is formed in the bottom surface 122 of the test array upwardly projecting from an open portion of the bottom surface 122 and disposed between the row of microwells 124 and a reservoir 134 and is connected by a first microchannel 130 to the reservoir 134. Evaporation well 132 has a closed dome-shaped upper well surface 136 proximate the top surface 120 of the test array with a sealable vacuum port 138 formed therein as an opening in the dome-shaped upper well surface 136 of the evaporation well 132, as seen in FIG. 5A depicting a cross-section view along lines A—A of FIG. 5. Microwells 124 have the general shape of a closed well projecting upwards from the bottom surface 122 of the array 12 with a depth of about three-fourths the thickness of array 12, as seen in FIG. 5B depicting a cross-section view along lines B—B of FIG. 5, and have their openings along the bottom surface 122 of array 12.

As seen in FIG. 6, first microchannel 130 is formed as a open groove in the bottom surface 122 of the array 12 and connects the evaporation well 132 to a open top rectangular shaped inoculum-broth solution receiving reservoir 134 best seen in FIG. 5, the reservoir 134 having a closed bottom illustrated by dashed lines in FIG. 6. One end of the bottom of the reservoir 134 has a flow opening 140 also illustrated in FIG. 6 to allow inoculum-broth solution dispensed into the open top of reservoir 134 to flow from reservoir 134 through first microchannel 130, firstly into the sacrificial evaporation well 132 and therefrom to a second microchannel 142 and therefrom sequentially through a number of connecting microchannels 143 to each of the series of microwells 124. The open surface portions of first and second microchannels 130 and 142, connecting microchannel 143, flow opening 140, sacrificial evaporation well 132, and microwells 124 along the bottom surface 120 of array 12 are closed by sealing over with a layer of adhesive film (not shown) during a manufacturing process in which antimicrobics of clinical interest are placed in the different microwells 124 but not in the sacrificial evaporation well 132. Optionally, one microwell 124 may be left empty of antimicrobics for use in generating a reference signal during optical analysis.

Sacrificial evaporation well 132 may be seen in cross-section in FIG. 5A as comprising a pair of mutually opposed parallel endwalls 144 connected by a pair of mutually opposed parallel sidewalls 146 (only one sidewall 146 is visible in this view). Endwalls 144 are shorter than sidewalls 146; endwalls 144 and sidewalls 146 are substantially perpendicular to the bottom surface 122 of test array 12. The upper surfaces of endwalls 144 and sidewalls 146 are connected by the cone-shaped upper well surface 136 to form a small generally rectangular evaporation chamber 148 enclosed by sacrificial well 132. An important feature of sacrificial well 132 is the sealable vacuum port 138 formed as an opening in the cone-shaped upper surface 136 so that air may be evacuated from sacrificial well 132, microchannels 130 and 142, connecting microchannel 143, and microwells 124 during an inoculum-broth filling operation described hereinafter. Evaporation chamber 148 is typically sized to accommodate an amount of inoculum-broth solution in the 0.02 to 0.04 mL range.

FIG. 5B illustrates the microwells 124 as having a top surface 150 portion of array 12, a rounded endwall portion 152 of the indented sidewall 126, a flat endwall 154 of the indented sidewall 126 and two parallel sidewalls 156. Both endwalls 152 and 154 are formed substantially perpendicular to the lower bottom surface 122 of array 12 and are separated by the two parallel sidewalls 156. The irregular top surface 150, the flat endwall portion 154, and the rounded endwall portion 152 cooperate to define a small AST reaction chamber 158. The top surface 150 is shaped to form a recessed top edge portion 160 of AST reaction chamber 158 that functions as a bubble trap 160 for bubbles that may be generated when inoculum-broth solution is dispensed from reservoir 134 to sacrificial well 132 and test microwells 132. It has been discovered that when the microwells 124 are shaped as described herein, and when connecting microchannel 143 is positioned on the opposite surface of microwell 124 across from the bubble trap 160, bubble trap 160 is effective in capturing bubbles when microwell 124 is comprised of a generally hydrophilic material, like styrene. It has been observed that with such an arrangement, as inoculum-broth solution flows into microwell 124, any air remaining within microwell 124 is urged by the expanding inoculum-broth solution without leaving any entrapped air pockets in the critical upper central area of the AST reaction chamber 158. Such a filling is pictorially illustrated in FIG. 24. Thus, air is removed away from the central area of the top surface 150 through which a beam of interrogating radiation may pass as described hereinafter without requiring bubble traps separate from the AST reaction chamber 158 or bubble traps with complex valve features.

In an exemplary embodiment, the upper top surface 120 and lower bottom surface 122 are about 0.3–0.4 inches wide, the indented sidewall 126 is about 0.2–0.25 inches in height and the elongate dimension of the test array 12 is about 2.5–3.0 inches in length. In such an embodiment, the microchannel 42 would be sized with a width and depth of about 0.010 to 0.020 inches. Preferably, the AST test array 12 is constructed of a moldable plastic material like styrene, but other types of material can be used. Most preferably, the material used in constructing array 12 is generally translucent, so as to allow uninterrupted transmission of light through microwells 124 during AST testing in the microbiological analyzer 10. AST testing may conveniently be accomplished by directing a beam of interrogating radiation from above or below each AST array 12 through a upper central arc portion 157 of the top surface 150 of each microwell 124 and measuring the degree of absorption or change in color or generation of a fluorescent signal using a calorimetric or fluorometric photodetector located below or above each microwell 124. For this reason, the upper center portion 157 of the top surface 150 of every microwell 124 and the lower center portion 159 of the top surface 150 of every microwell 124 are molded so as to have a surface finish smoothness equivalent to or more smooth than SPI #A-1 grade #3 diamond buff in order to minimize optical interference.

The sacrificial evaporation well 132 is designed to accomplish two important purposes: firstly, provision of a evaporation chamber 148 from which sacrificial evaporation of inoculum-broth solutions may take place, thereby inhibiting evaporation of solution from microwells 124. Evaporation from microwells 124 is inhibited because evaporation initially must occur from within short microchannel 130 and then from the sacrificial evaporation chamber 148 before evaporation might occur from long microchannel 142 and microwells 124. Evaporation chamber 148 further provides the sealable vacuum port 138 through which air contained within microwells 124 may be evacuated so that air within microwells 124 does not bubble through broth in the reservoir 134 during evacuation and generate air bubbles within inoculum-broth solutions. After evacuation, vacuum port 138 is subsequently sealed so as to generate a flow of inoculum-broth solution from reservoir 134 into the microwells 124.

Figure 5C:
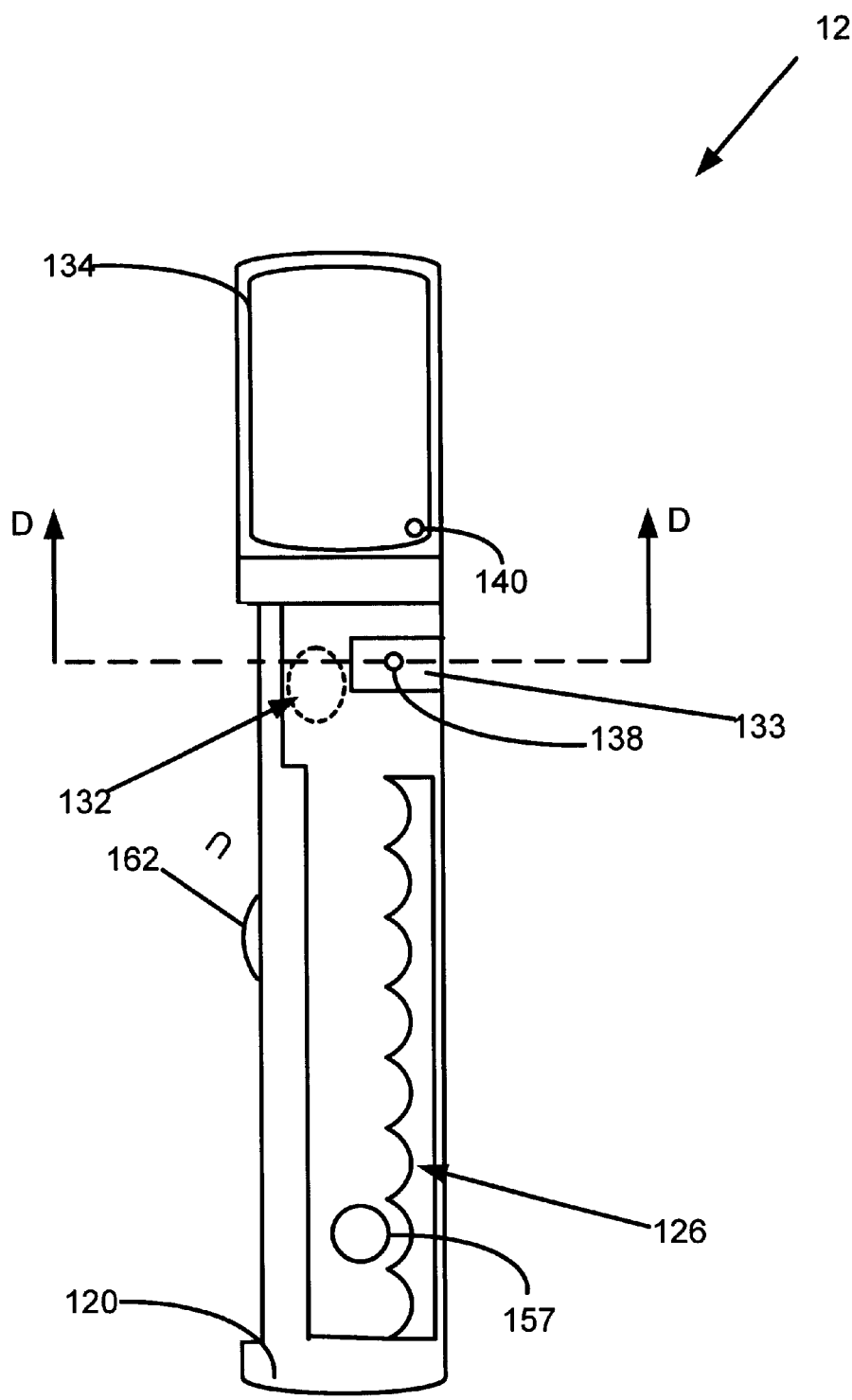
FIG. 5C is a top view of an alternate AST test array useful within the present invention.
Figure 5D:
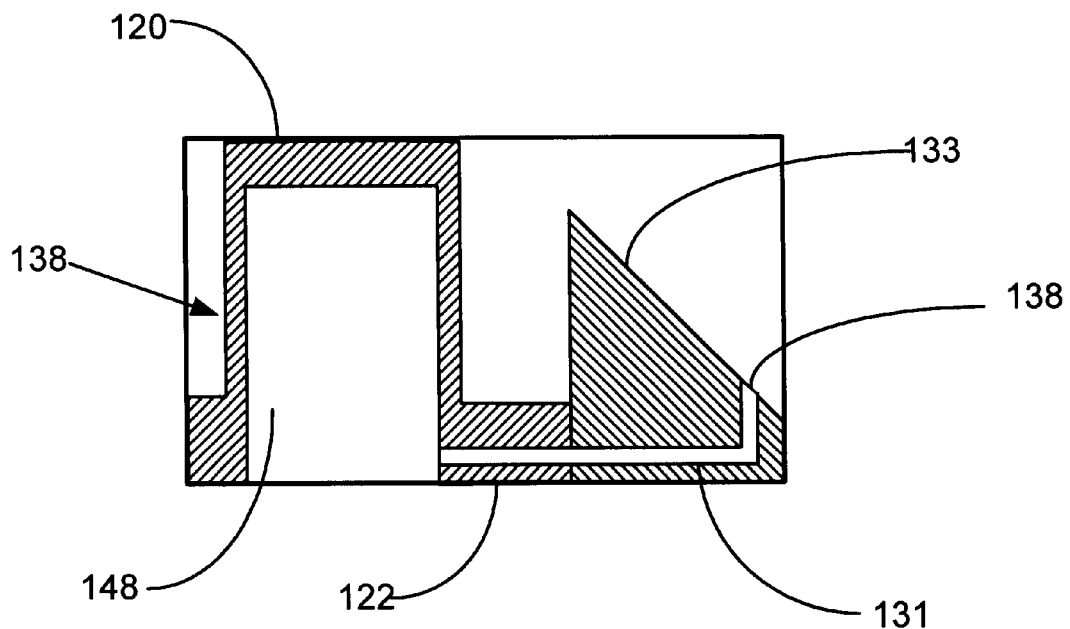
FIGS. 5D and 5E are cross-section views of the AST test array of FIG. 5C.
Figure 5E:
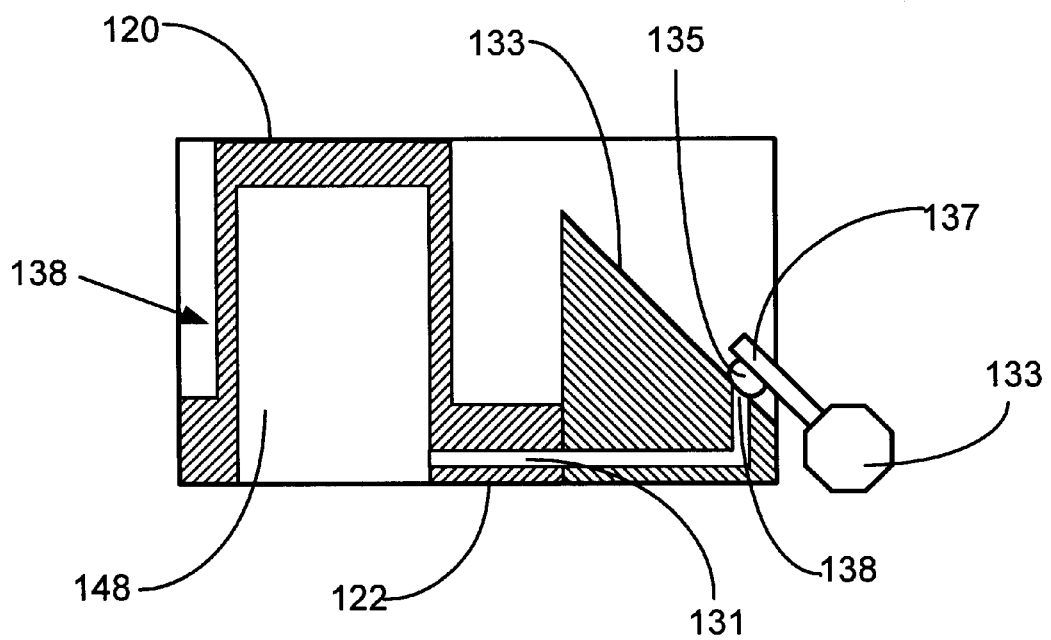

In an alternate embodiment of AST array 12 illustrated in FIG. 5C showing the top view of an AST array 12, taken in conjunction with FIG. 6B, showing the bottom view of an AST array 12, sacrificial evaporation well 132 may be separated from vacuum port 138 but connected thereto by a microchannel 131. FIG. 5D is a cross-section view along lines D—D of FIG. 5C and shows such a separated arrangement of sacrificial evaporation well 132 and vacuum port 138 in an embodiment in which vacuum port 138 is seen as disposed at the upper surface of an inclined portion 133 of the upper surface 122 of AST array 12. In this embodiment, vacuum port 138 is in fluid communication with sacrificial evaporation well 132 the reservoir 134 and is adapted to be temporarily sealed by a stopper pressed thereon. Thus, vacuum port 138 is not sealed by a heating action but is alternately sealed by temporarily forcing a resilient stopper 135 over the vacuum port 138 to effectively seal vacuum port 138 against air flow during the aforedescribed vacuum filling process. This temporary sealing step is illustrated in FIG. 5E where a moveable stopper support 137 is shown as positioned by an actuator 139 so that stopper 135 effectively seals vacuum port 138 thereby to fill microwells 124 with inoculum-broth solution when vacuum is released. In a preferred embodiment, vacuum port 138 is placed as illustrated between sacrificial evaporation well 132 and reservoir 134. Alternate locations of vacuum port 138, for example, between sacrificial evaporation well 132 and microwells 124, have not given satisfactory performance. Once the vacuum is released within the vacuum chamber and microwells 124 are filled with inoculum-broth solution, the resilient stopper 135 may be removed from port 48.

As seen in FIG. 5, array 12 further includes a protrusion 162 formed in the sidewall 128, the protrusion 162 being generally shaped as a bulge extending from the body of the array 12 and formed in the uppermost portion of the sidewall 128. The protrusion 162 is used to facilitate loading and retention of an AST array 12 within the AST carrier 74 and in an exemplary embodiment has dimensions of about 0.26–0.30 mm extension outward from the body of array 12, about 3–4 mm length along the edge of the array 12 and about 0.6–0.8 mm depth along the sidewall 17 of the array 12. Alternately, a high friction material such as silica or an inert powder may be coated onto the side of array 12 in place of protrusion 162 to accomplish a similar function.

Figure 7:
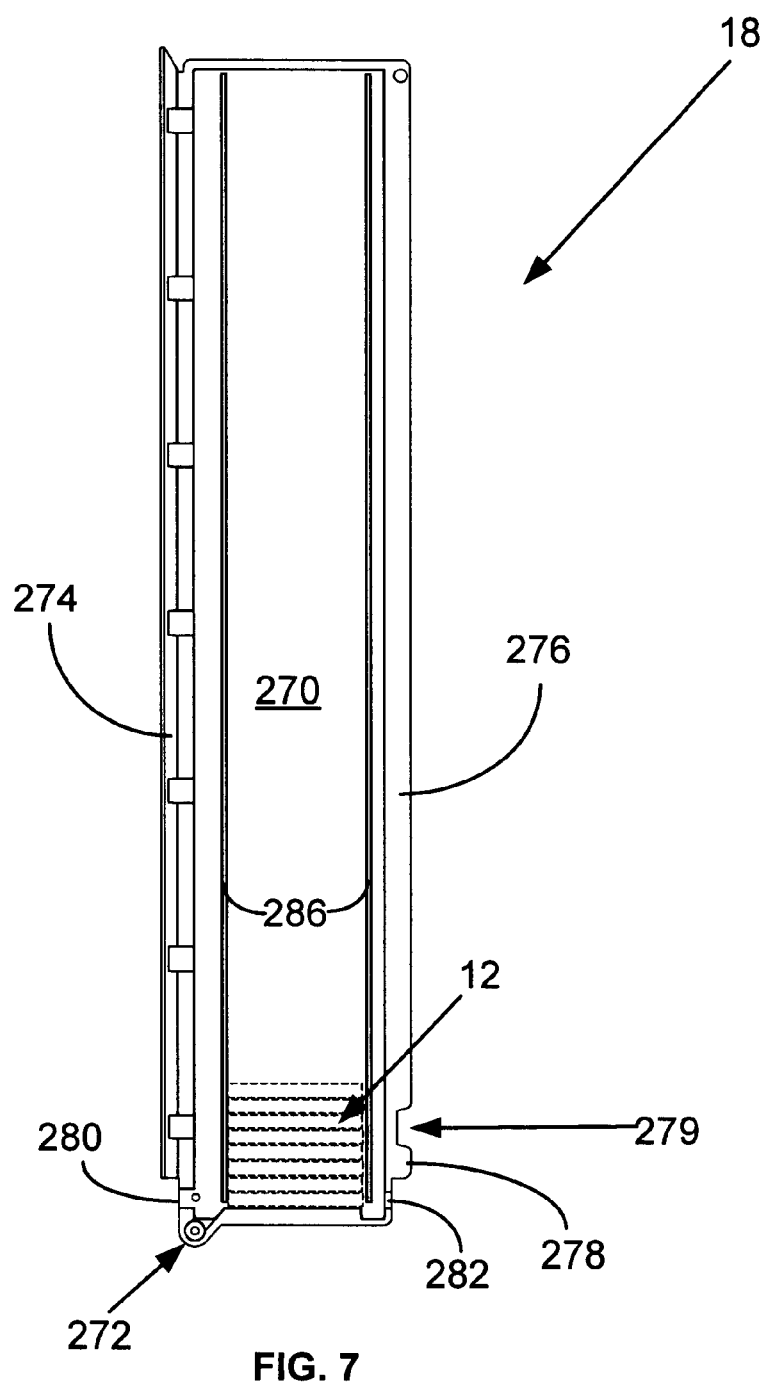
FIG. 7 is a perspective view of an AST test array canister useful within the present invention.
Figure 7A:
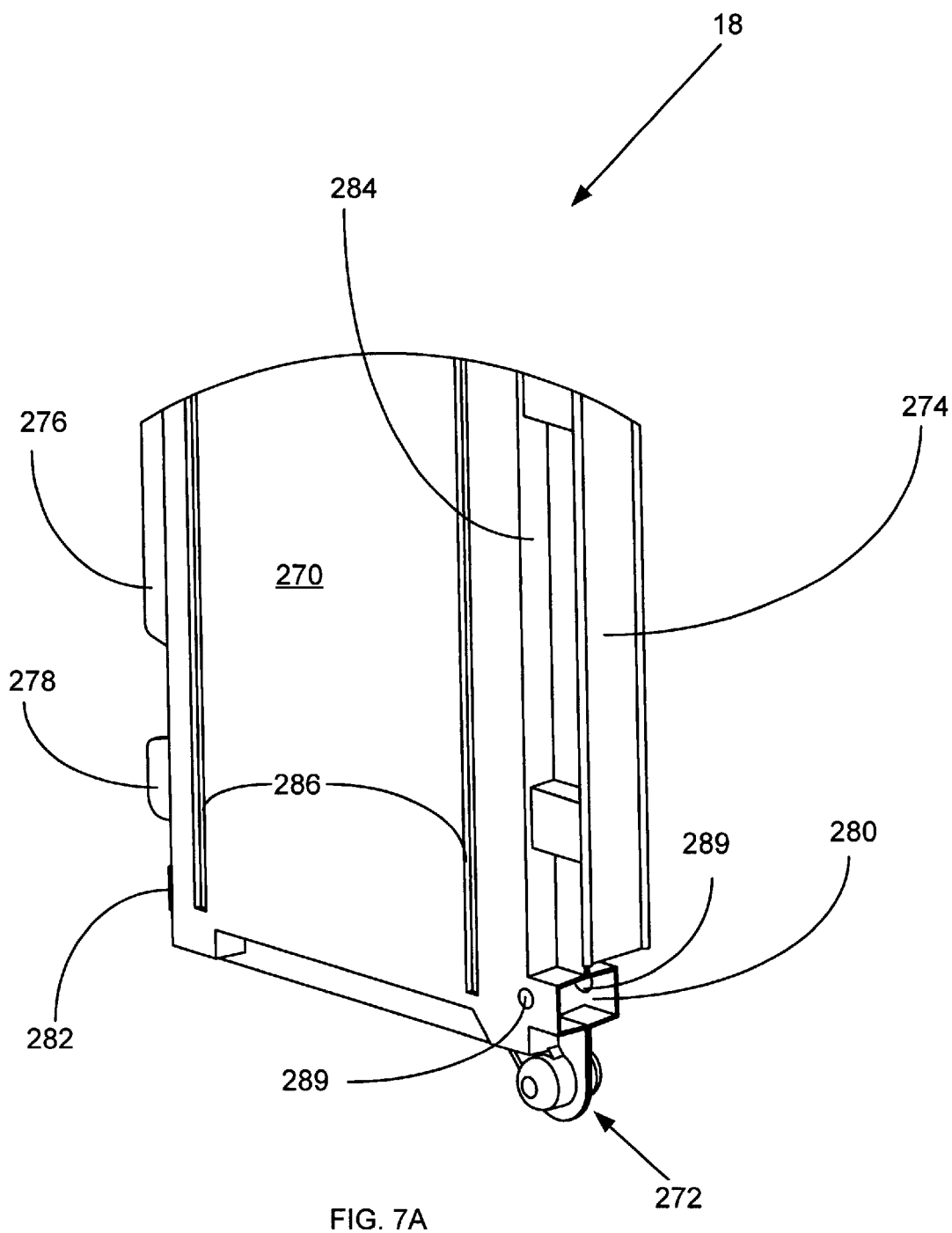
FIG. 7A is an enlarged side elevation view of the AST test array canister of FIG. 7.
Figure 7B:
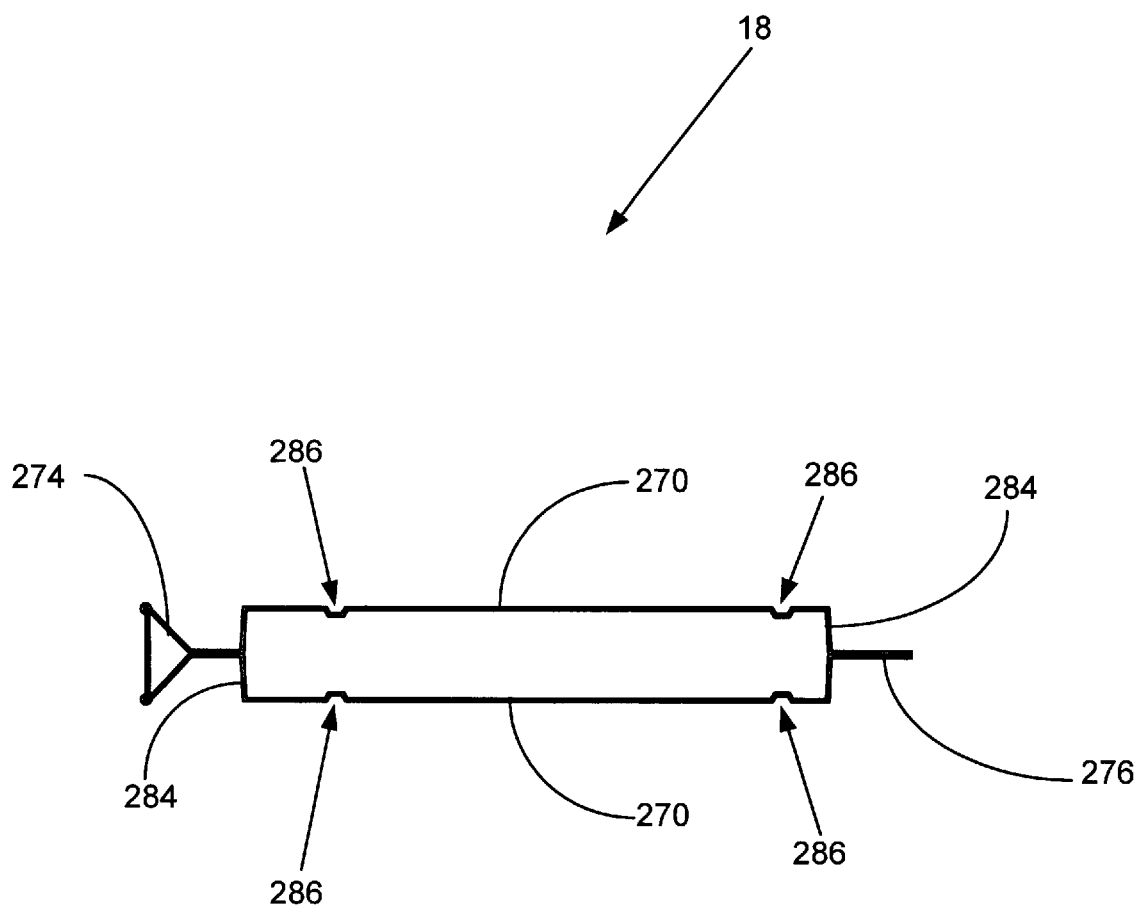
FIG. 7B is a sectional view of the AST test array canister of FIG. 7.

FIG. 7 is a side elevation view of an elongate AST canister 18 having a generally rectangular cross-section with two AST canister flat sides 270 and two AST canister narrow sides 284 (FIG. 7B), the flat side 270 being about 10 times greater in dimension than the narrow side 284. AST canister 18 is sized to house a plurality of AST test arrays 12 stacked one atop another (indicated by dashed lines in FIG. 7.) and maintained secure by pairs of AST canister internal ribs 286 extending along the elongate height of AST canister flat sides 270. Key features of the AST canister 18 include an AST canister cylindrical pivot 272 (best seen in FIG. 7A) shaped to seat into a mating dock within inventory chamber 22 to allow the AST canister 18 to be rotated using an AST canister handle 274 to a vertical position where an AST canister seating flange 276 fits into a vertical groove 21 (FIG. 1) in AST canister post 20. AST canister seating flange 276 extends the full length of an AST canister narrow side 284 except for a small AST canister alignment key 278 and alignment notch 279 provided to confirm proper orientation of AST canister 18 with a corresponding slot for key 278 and stop for notch 279 within the vertical groove 21 in AST canister post 20. AST canister 18 also comprises an AST canister eject port 280 formed in the AST canister narrow side 284 proximate AST canister cylindrical pivot 272 and sized to allow the lowermost AST test array 12 within the plurality of AST test arrays 12 stacked one atop another to be pushed out of AST canister 18. AST test arrays 12 may be pushed out of AST canister 18 using a plunger entering canister 18 through an AST canister plunger port 282 that is aligned with AST canister eject port 280 and is formed in the AST canister narrow side 284 opposing AST canister eject port 280. A pair of inwardly projecting dimples 289 are formed in AST canister flat sides 270 and extend into AST canister eject port 280 to retain AST test arrays 12 within AST canister 18, preventing accidental dislodging of a AST test array 12 from canister 18 and also. to prevent AST test arrays 12 from being improperly inserted back into canister 18.

Figure 8:
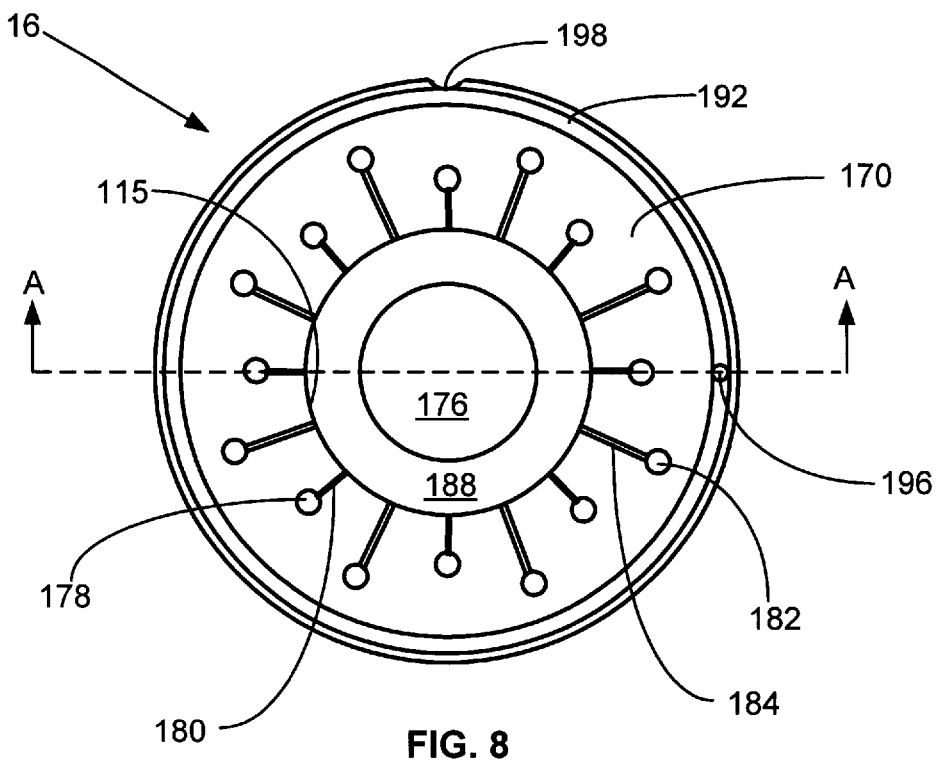
FIG. 8 is a top view of an ID test rotor useful within the present invention.
Figure 9:
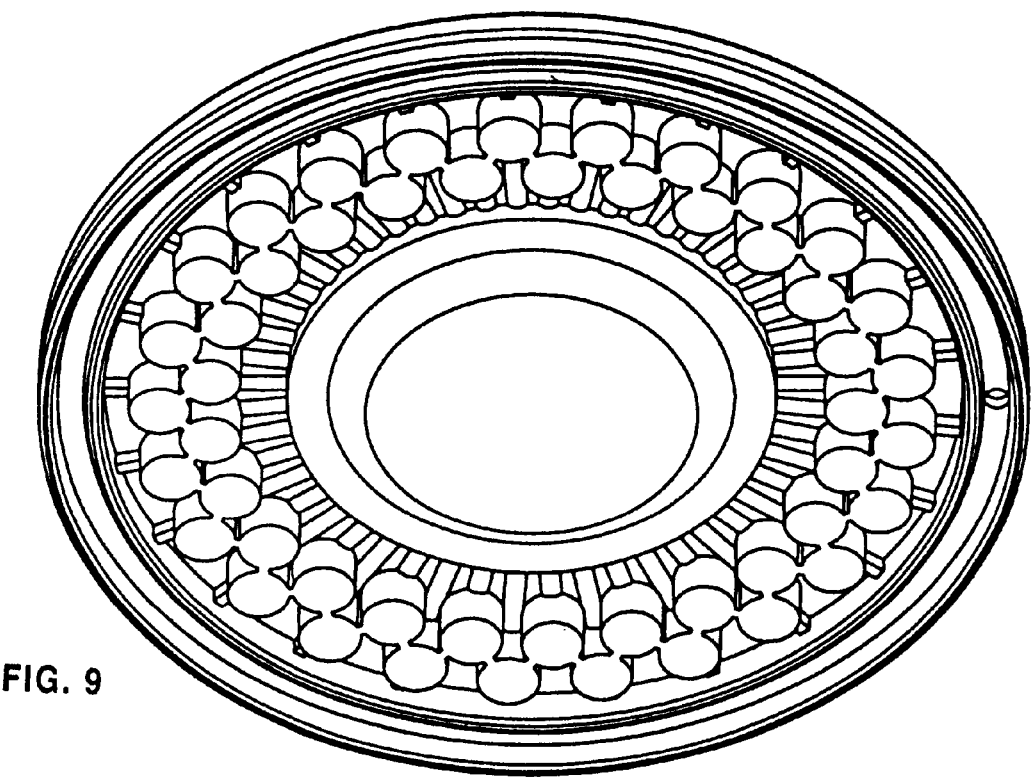
FIG. 9 is a perspective bottom view of the ID test rotor of FIG. 8 useful within the present invention.

FIG. 8 is a top plan view of the ID test rotor 16 useful in the present invention and described in a co-pending U.S. patent application Ser. No. 09/841,408. Rotor 16 comprises a rotor upper surface 170 and a rotor bottom surface 172 seen in FIG. 9. ID test rotor 16 has a rotor central axis 171, a rotor diameter D, and a generally flat radial outer sidewall 174 connecting the upper surface 170 and bottom surface 172 at the diameter D of the rotor 16. A recessed circular central portion 176 is recessed below the upper surface 170 of rotor 16. A first plurality of downwardly projecting microwells 178 are formed in the upper surface and are distributed equidistant from one another in a first circular array located at a first distance from the central axis 171; a second plurality of downwardly projecting microwells 182 are also formed in the upper surface 170 and are distributed equidistant from one another in a second circular array, located at a second distance from the central axis, the second distance being larger than the first distance; a first plurality of downwardly projecting microchannels 180 are formed in the top surface and connect the recessed central portion 176 to the first plurality of microwells 178; a second plurality of downwardly projecting microchannels 184 are formed in the upper surface 170 and connect the recessed central portion 176 to the second plurality of microwells 182. The recessed circular central portion 176 is surrounded by a generally inclined annulus portion 188. The plurality of first microchannels 180 extends radially outwards from a radial wall 190 formed vertically at the outer periphery of an inclined annulus 188 extending outwards from recessed central portion 176 towards the first circular array of equally spaced microwells 178; the plurality of second equally spaced microchannels 184 also extends radially outwards from the radial wall 190 to the second circular array of microwells 182. The length of first microchannels 180 is generally about ½ to ⅔ the radial length of second microchannels 184. The two arrays of equally spaced microwells 178 and 182 are an important feature of rotor 16 since the two arrays allow for a greater number of test microwells that is typically possible with conventional centrifugal rotors having a single array of test wells equidistant from the center of the rotor. The first and second plurality of downwardly projecting microwells 178 and 182 are shaped and sized equally and the first and second plurality of microchannels 180 and 184 have the same cross-section depth and width dimensions.

Figure 8A:
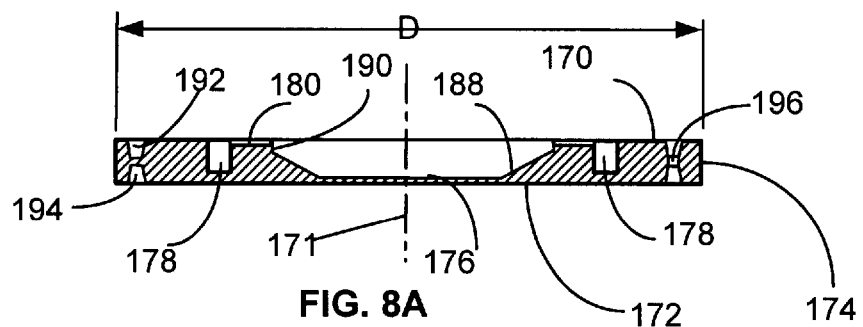
FIGS. 8A and 8B are cross-section views of the ID test rotor of FIG. 8.

FIG. 8A shows a key feature of rotor 16 as a top radial trough 192 formed in the top surface and a bottom radial trough 194 formed in the bottom surface, the top 192 and bottom 194 troughs are vertically aligned with one another but are not intersected and are provided to facilitate handling of the rotor 16 by ID robotic device 50 and by ID rotor filling and centrifuging apparatus 52 described hereinafter. Another feature of rotor 16 is a single through opening 196 formed between the top radial trough 192 and the bottom radial trough 194 thus fully extending from the top surface upper surface 170 to the bottom surface 172 to facilitate radial positioning of rotor 116 within an ID rotor optical analyzer 230 described hereinafter. Optionally, a small notch 198 may be formed in sidewall 174 and made to fully extend from the top surface 170 to the bottom surface 172 to facilitate reagent pre-loading of microwells 120 and 124 during a manufacturing process.

Figure 8B:
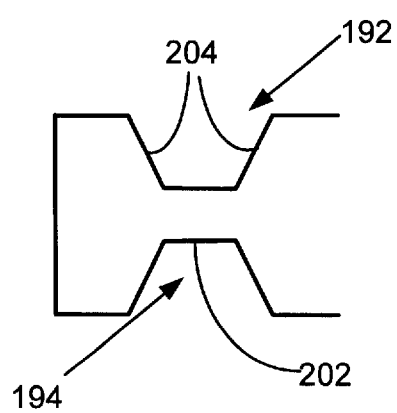
Figure 8C:
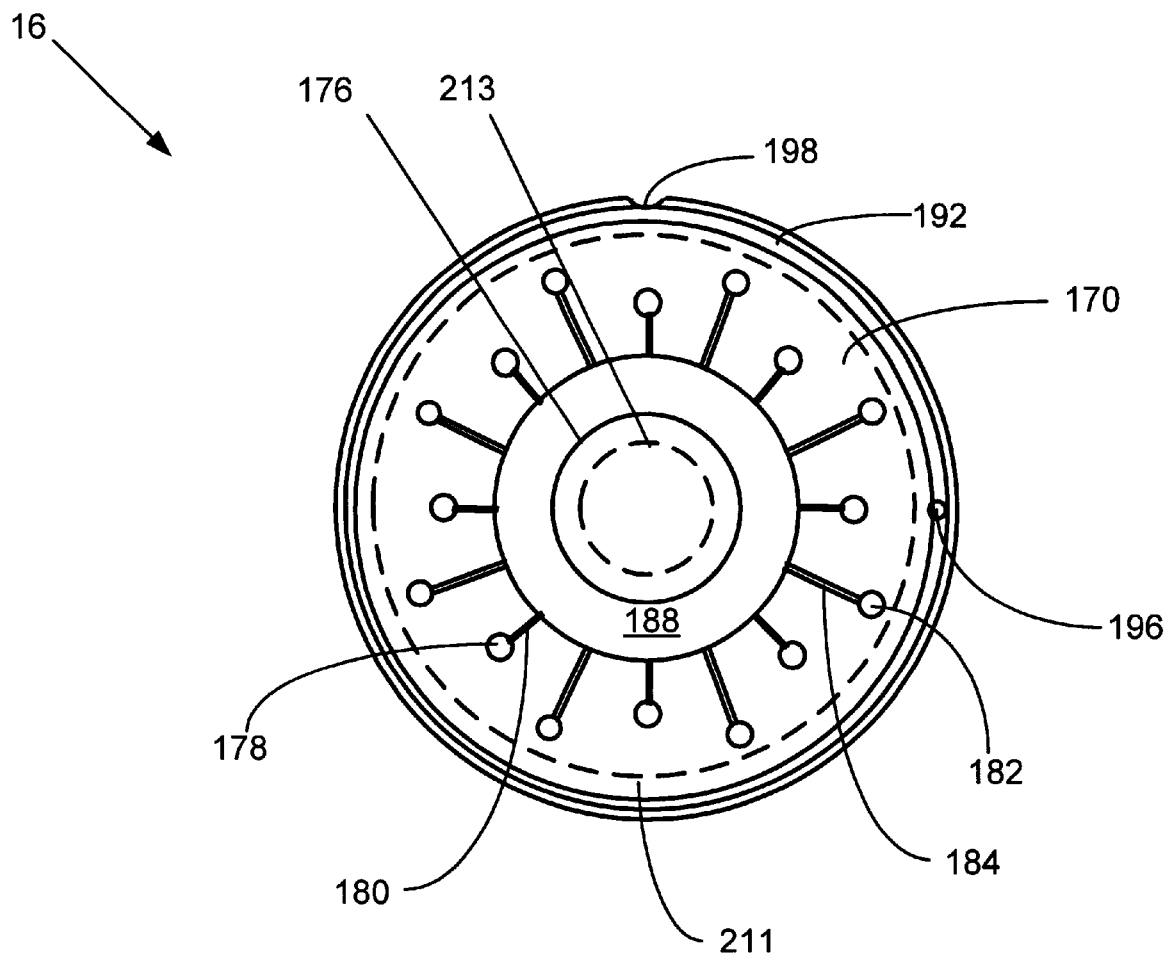
FIG. 8C is a top view of a first alternate ID test rotor useful within the present invention.

FIG. 8C illustrates an alternate embodiment of the ID test rotor 16 of the present invention in which a circular, thin layer 211 of tape stock is shown in dashed lines for clarity and has an opening 213, also shown in dashed lines, formed at its center and adhesively adhered to the top surface 170 of rotor 16. Tape stock layer 201 is positioned so that the opening 213 is aligned over the recessed central portion 176 of the rotor. Opening 213 is provided within the tape stock layer 211 to allow free access by an inoculum dispensing mechanism to an inoculum receiving chamber formed by surface 176, inclined annulus portion 188, radial wall 190 and tape stock layer 211. The opening 213 in tape stock layer 211 generally has a smaller diameter than that of central portion 176. Tape stock layer 211 is typically made of a thin layer of about 2 to 4 mils thickness of a plastic material like polypropylene or polyester or the like and is affixed to the top surface 110 with adhesive.

Figure 8D:
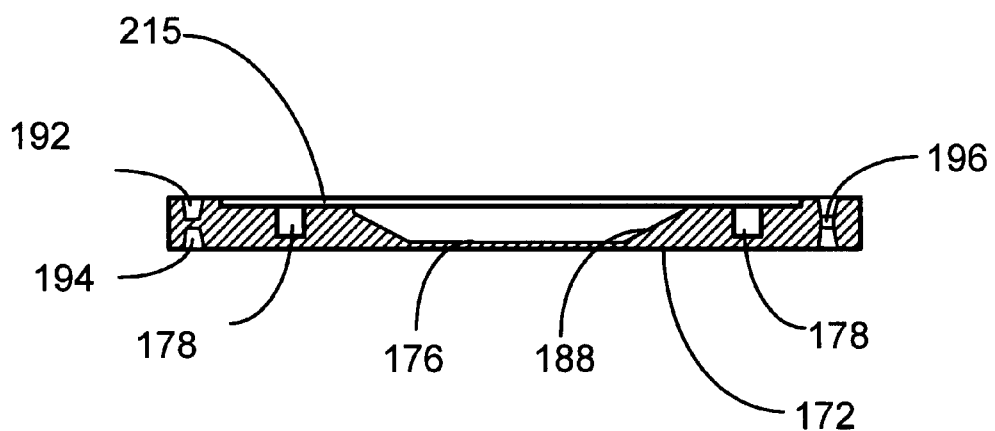
FIG. 8D is a cross-section view of an second alternate ID test rotor useful within the present invention.

FIG. 8D illustrates another alternate embodiment of the ID test rotor 16 of the present invention of FIG. 5 in which a thin flat recess 215, not shown to size, is formed in the top surface 170 with dimensions to accept tape stock layer 211 within recess 215. Preferably, recess 215 has a depth of about 0.005 to 0.015 inches so that the top of tape stock layer 211 may be aligned below the top surface 170 of rotor 16. For purposes of clarity, tape stock layer 211 is not shown placed within recess 215. In such an embodiment, a number of ID rotors 16 may be stacked atop one another with the top surface 170 of one rotor 16 in contact with the bottom surface 172 of an adjacent rotor 16. Recess 215 thereby prevents contact between the tape stock layer 211 and the bottom surface 172 of the adjacent rotor 16. In an exemplary embodiment, the features described in FIG. 8D are included in the rotor of FIG. 5.

Figure 8E:
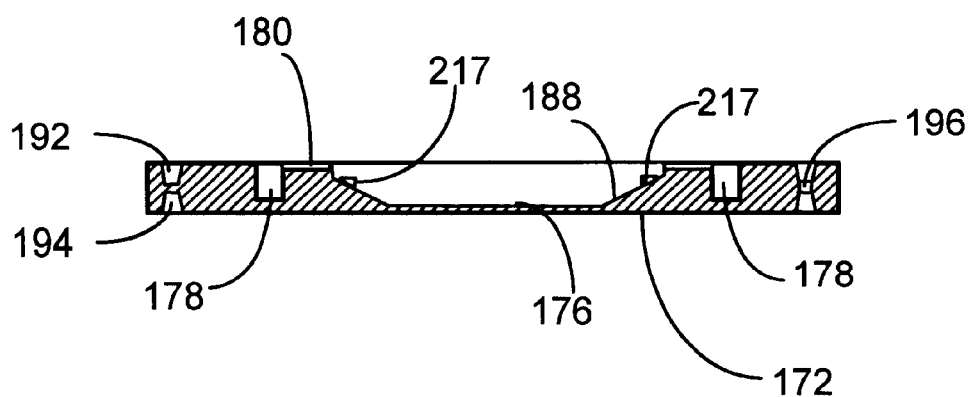
FIG. 8E is a cross-section view of a third alternate ID test rotor useful within the present invention.

FIG. 8E illustrates another alternate embodiment of the ID test rotor 16 of the present invention in which the inclined annulus portion 188 further comprises a radial ridge 217 positioned proximate the first and second plurality of microchannels 180 and 184 and projects upwards from the surface of the annulus portion 188. Ridge 217 acts somewhat like a barrier in retaining a portion of sample fluids that are forced through microchannels 180 and 184 into microwells 178 and 182 in a filling process described hereinafter. In use, the retained sample portion is sacrificially evaporated and thereby acts to eliminate evaporation of sample within microchannels 180 and 182 and microwells 178 and 182 and 124. In an exemplary embodiment, the features described in FIGS. 8D and 8E are included in the rotor of FIG. 5.

In a particularly useful embodiment, rotor 16 comprises a body of polystyrene like Dow Chemical 666D or a similar moldable polymeric material and is about 0.015 inches thick and about 2 inches in diameter; microwells 178 and 182 are similar to one another in size and dimensions and have a diameter at the closed end in the range of about 0.090 to 0.094 inches; the walls of the microwells 178 and 182 are inclined slightly outwards to aid in removal during a molding process so that the diameter at the open end is in the range of about 0.100 to 0.108 inches. The depth of microwells 178 and 182 is in the range of about 0.100 to 0.108 inches and microchannels 180 and 184 are similar in cross-section dimensions and have a width in the range of about 0.014 to 0.016 inches and a depth in the range of about 0.014 to 0.016 inches. In this embodiment, and as illustrated in FIG. 8B, radial troughs 192 and 194 are seen as equally formed in both surfaces 170 and 172 and have flat bottoms 202 and trough sidewalls 204 inclined at about 30-degrees thereto; the flat bottoms 202 are about 0.060 inches wide between the trough sidewalls 204 and the trough sidewalls 204 are about 0.060 inches high.

Figure 10:
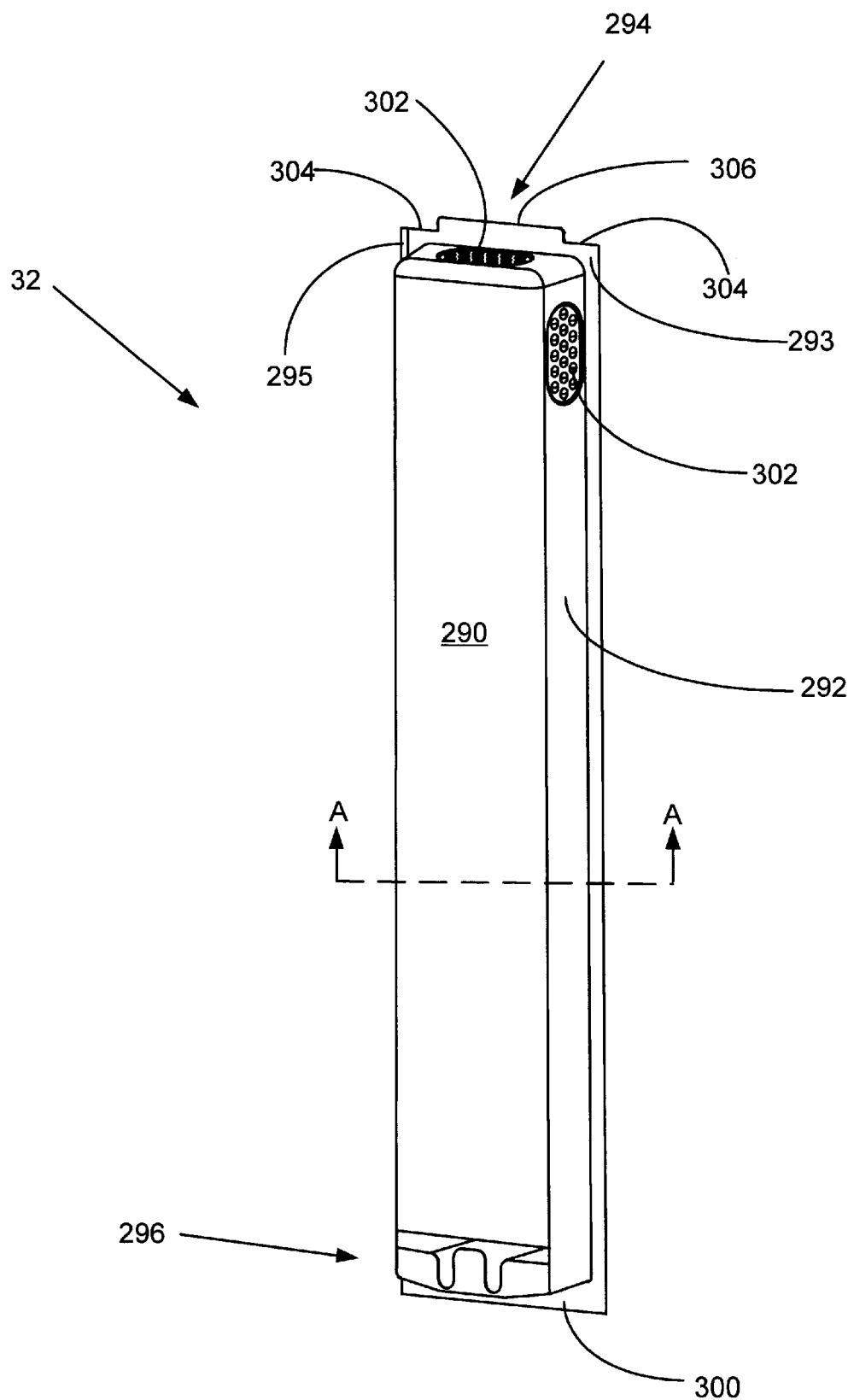
FIG. 10 is a perspective view of an ID canister useful within the present invention.
Figure 10A:
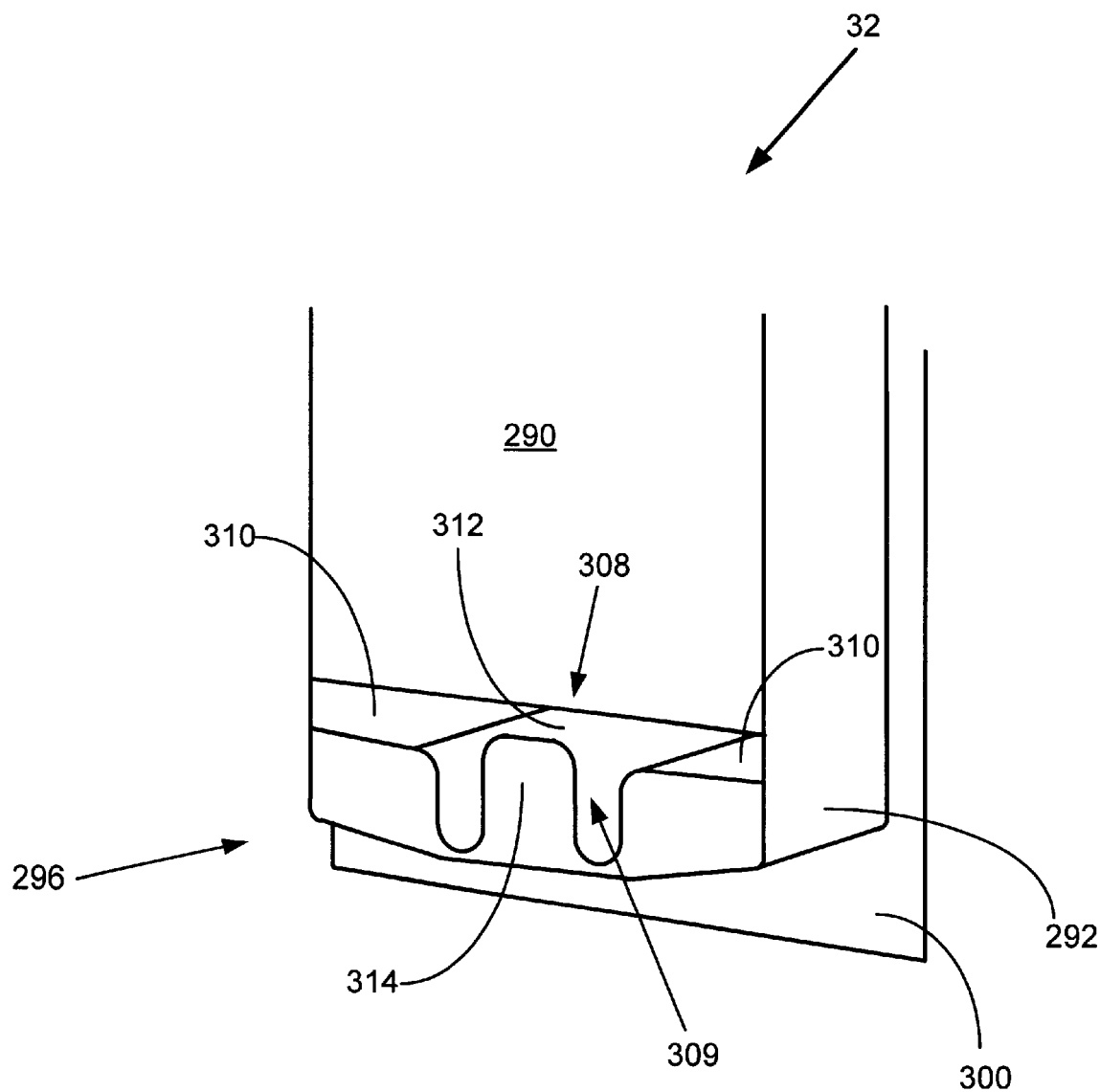
FIG. 10A is an enlarged perspective front view of the ID canister of FIG. 10.
Figure 10B:
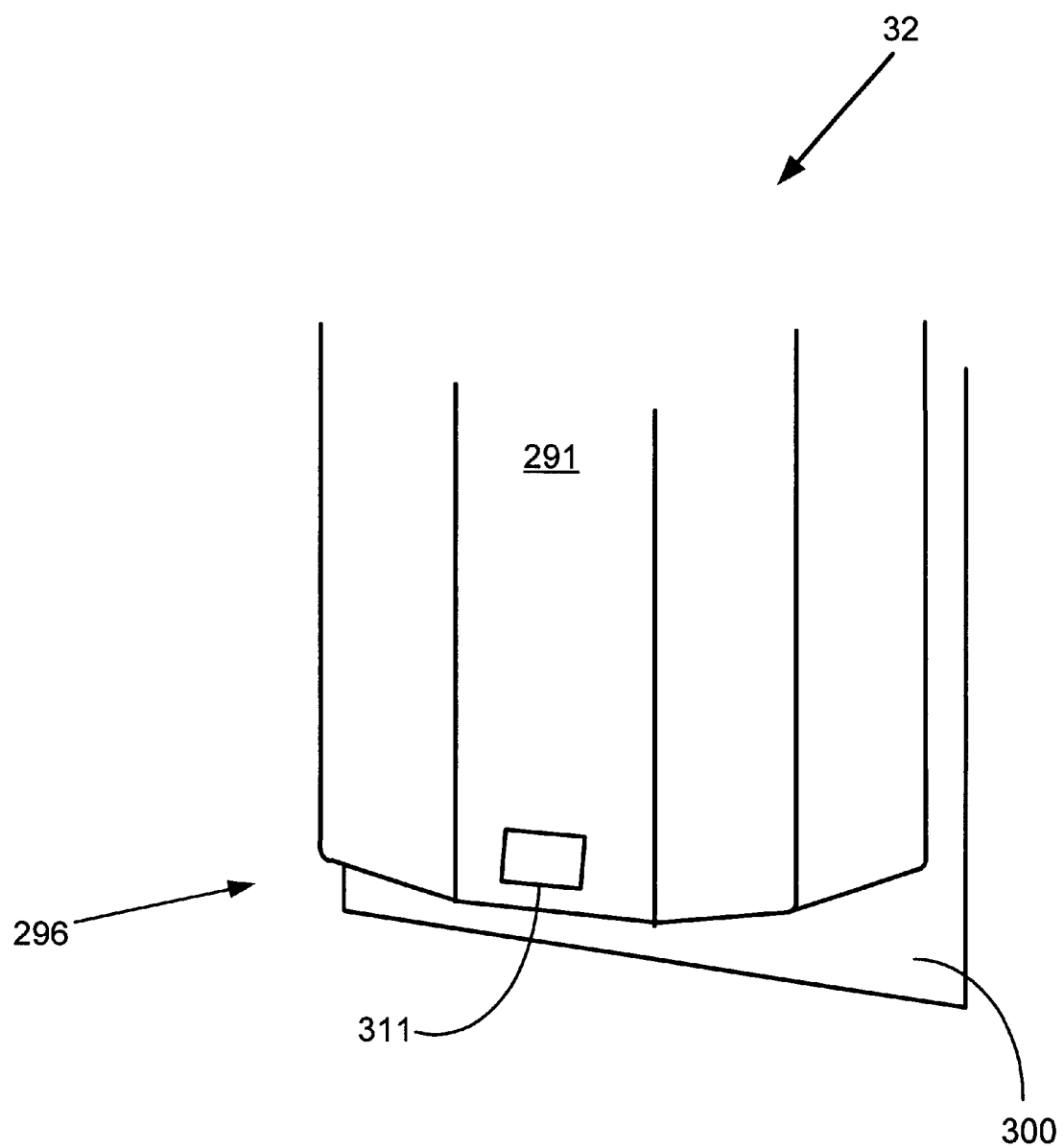
FIG. 10B is an enlarged perspective back view of the ID canister of FIG. 10.

FIG. 10 is a perspective view of a closed elongate ID rotor canister 32 having a generally rectangular cross-section formed by an ID canister front wall 290, a five-section ID canister back wall 291 (FIG. 10B) and two ID canister side walls 292, the ID canister front wall 290, irregular ID canister back wall 291 and ID canister side walls 292 are of dimensions so that a generally hexagonally shaped interior is formed to house a plurality of ID test rotors 16 stacked one atop another within the rotor canister 32. A top end portion 294 and a bottom end portion 296 close the end portions of rotor canister 32. A pair of bumped surface finger-pads 302 are formed in side walls 292 to facilitate handling by a operator. Key features of the ID rotor canister 32 include an ID canister mounting flange 300 shaped to seat into a mounting groove 301 (FIG. 1) within B/ID chamber 28 so that the rotor canister 32 may be secured within mounting groove 301 in a vertical position whereat two spring-loaded latching cams within B/ID chamber 28 engage a pair of rotor canister latch steps 304 formed as shown in a rotor canister latching flange 306 extending slightly above top end portion 294. The portion of latching flange 306 between steps 304 is confined between spring-loaded latching cams to provide proper vertical orientation. FIG. 10A is an enlarged view of the bottom end front side portion 296 of rotor canister 32 showing details of an ID rotor eject port 308 formed in ID canister front wall 290 proximate mounting flange 300 and sized to allow the lowermost ID test rotor 16 within the plurality of ID test rotors 16 stacked one atop another to be pushed out of rotor canister 32 by a plunger (not shown) and grasped by robotic device 50. FIG. 10B is an enlarged view of the bottom end back side portion 296 of rotor canister 32 showing a push-rod port 311 formed opposite ID rotor eject port 308 so that ID rotors 16 may pushed out of rotor canister 32 by a push-rod (not shown) and grasped by robotic device 50.

Figure 10C:
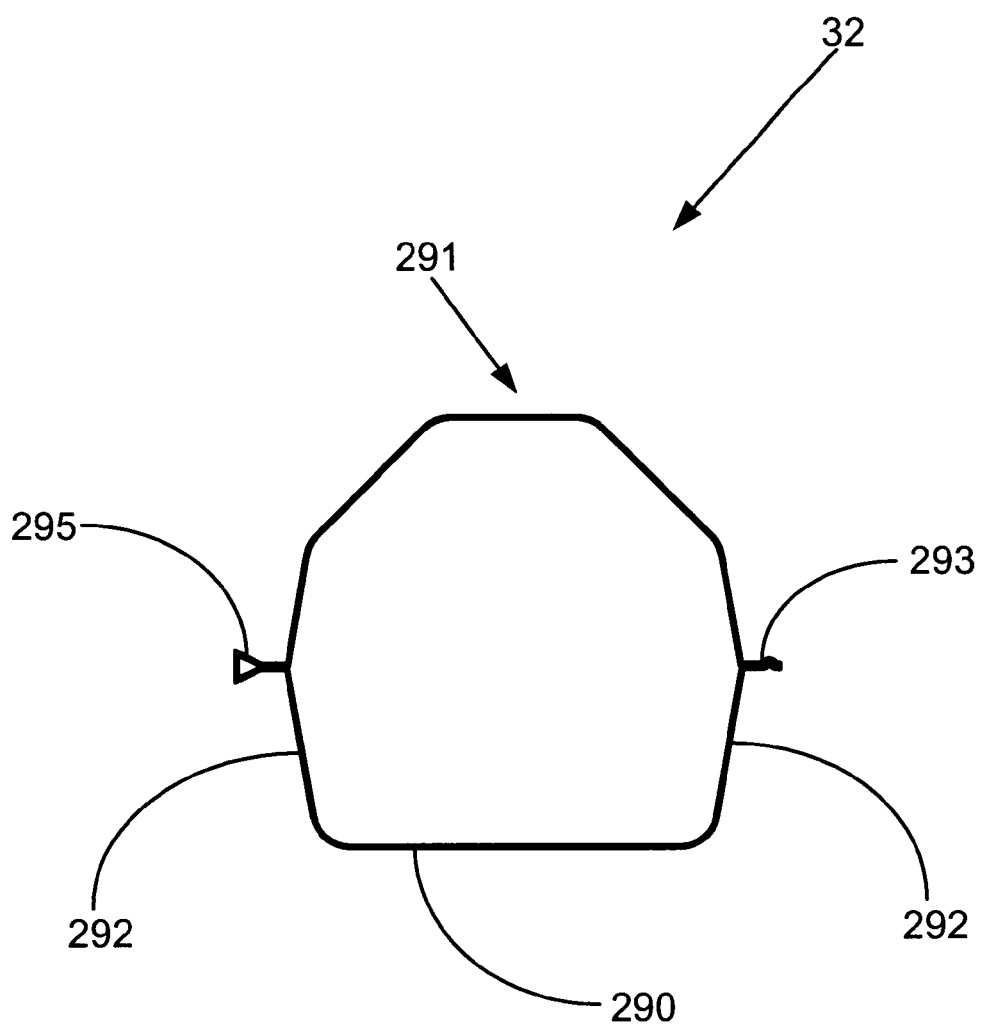
FIG. 10C is a cross-sectional view of the ID canister of FIG. 10.

ID test rotors 16 may be grasped by a pair of clamping teeth 226 of ID robotic device 50 (FIG. 16) described later. ID rotor eject port 308 has the shape of a rectangular opening 312 formed between a pair of rotor canister shoulders 310 projecting inwards from walls 292 and forming an opened rotor canister slit 313 at the top of protrusions 310. An open space 309 remains between shoulders 310. An upwardly projecting flexible tab 314 extends into rectangular opening 312 and serves to retain rotors 16 within canister 32, preventing accidental dislodging of a rotor 16 from canister 32 and also to prevent rotors 16 from being improperly inserted back into canister 32. Typically, canister 32 is formed as an indented sheet of plastic and is folded in half and sealed at flange 293 extending the full length of rotor canister 32 between ID canister front wall 290 and five-section ID canister back wall (FIG. 10C). An opposed elongate rotor canister fold 295 is created in a sealing operation and also extends the full length of rotor canister 32 between ID canister front wall 290 and five-section ID canister back wall. FIG. 10C is a sectional view of rotor canister 24 and best illustrates the flange 293, fold 295, five-section ID canister back wall 291, two ID canister side walls 292, and the ID canister front wall 290.

Figure 11A:
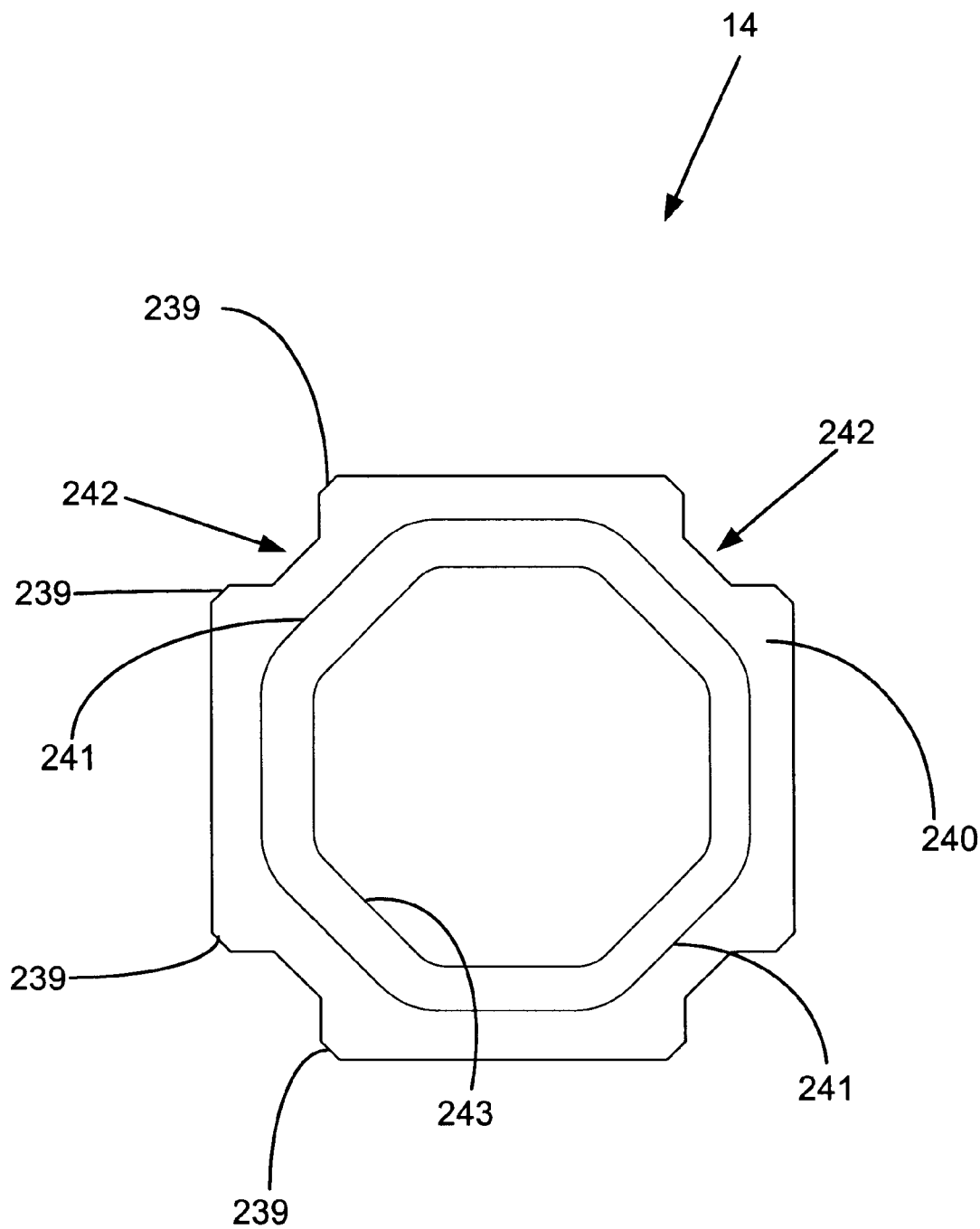
FIGS. 11A–11D are various views of a broth container useful within the present invention.
Figure 11B:
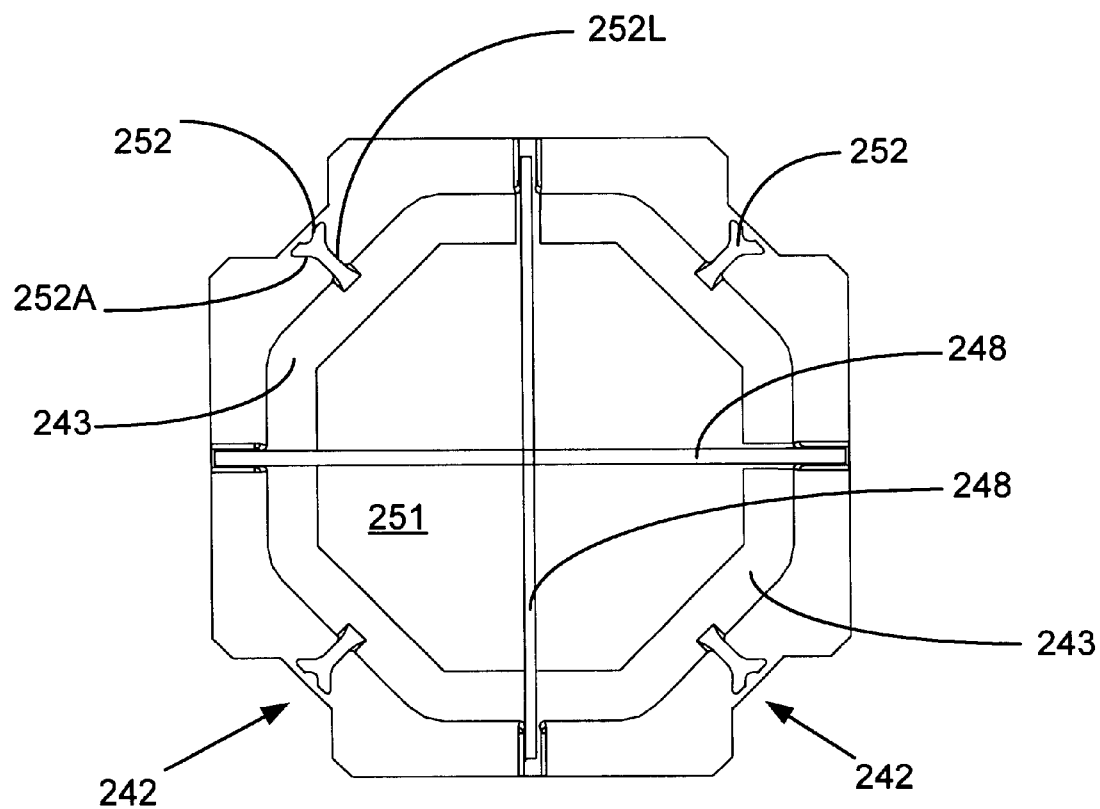

FIGS. 11A–11D and 12 A–12B show broth container 14 as adapted to be removed from broth canisters 24 on the B/ID carousel 26 by broth container handling apparatus 108, FIG. 21, and presented thereby to pipetting apparatus 46 within sample pipetting and transport system 60. The broth container 14 has a generally octagonal body cross section (FIG. 11D) and is formed as a open container with features that provide for secure confinement within broth canisters 24 and for reliable handling by broth container handling apparatus 108. Broth container 14 has a open top broth container surface 240 (FIGS. 11A and 12B) that is generally rectangular in shape except for four pairs of ears 239 created by indent notches 242 formed at opposing corners of top surface 240. Ears 239 are sized and shaped so that a number of broth containers 14 may be confined in broth canisters 24 in a common and stable orientation. The lower end of inner sidewalls 243 of broth container 14 are seen in FIGS. 11A and 11B.

Figure 11C:
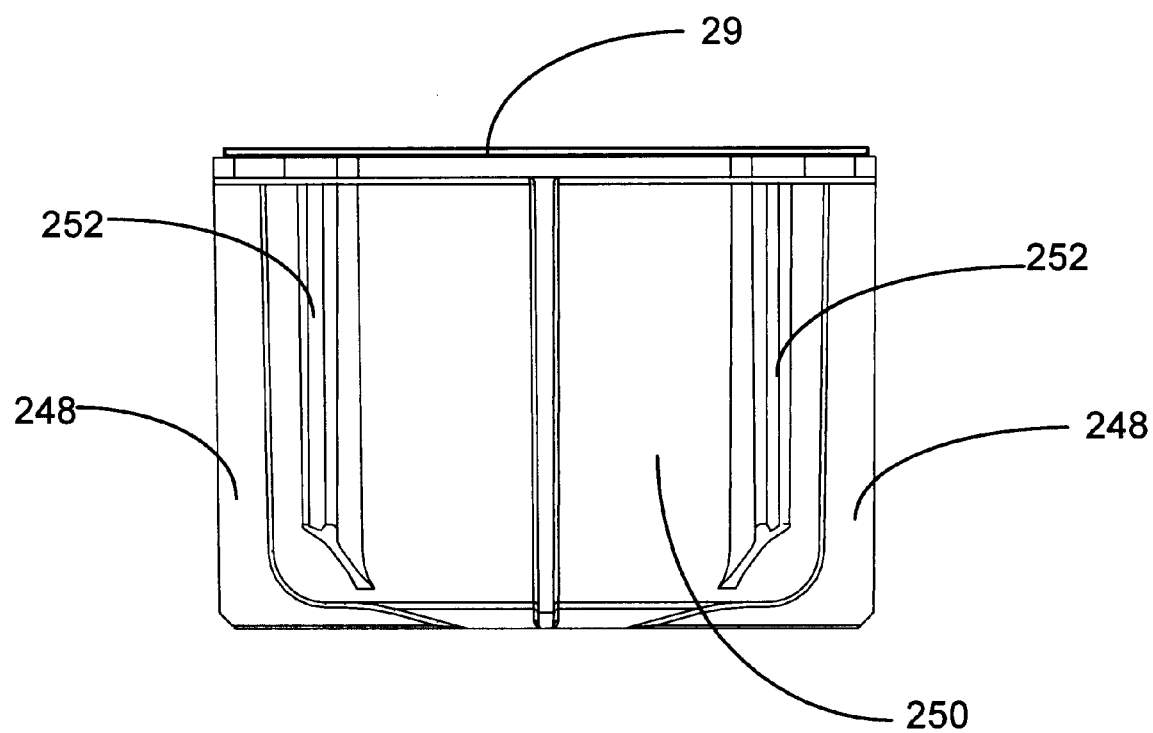
Figure 11D:
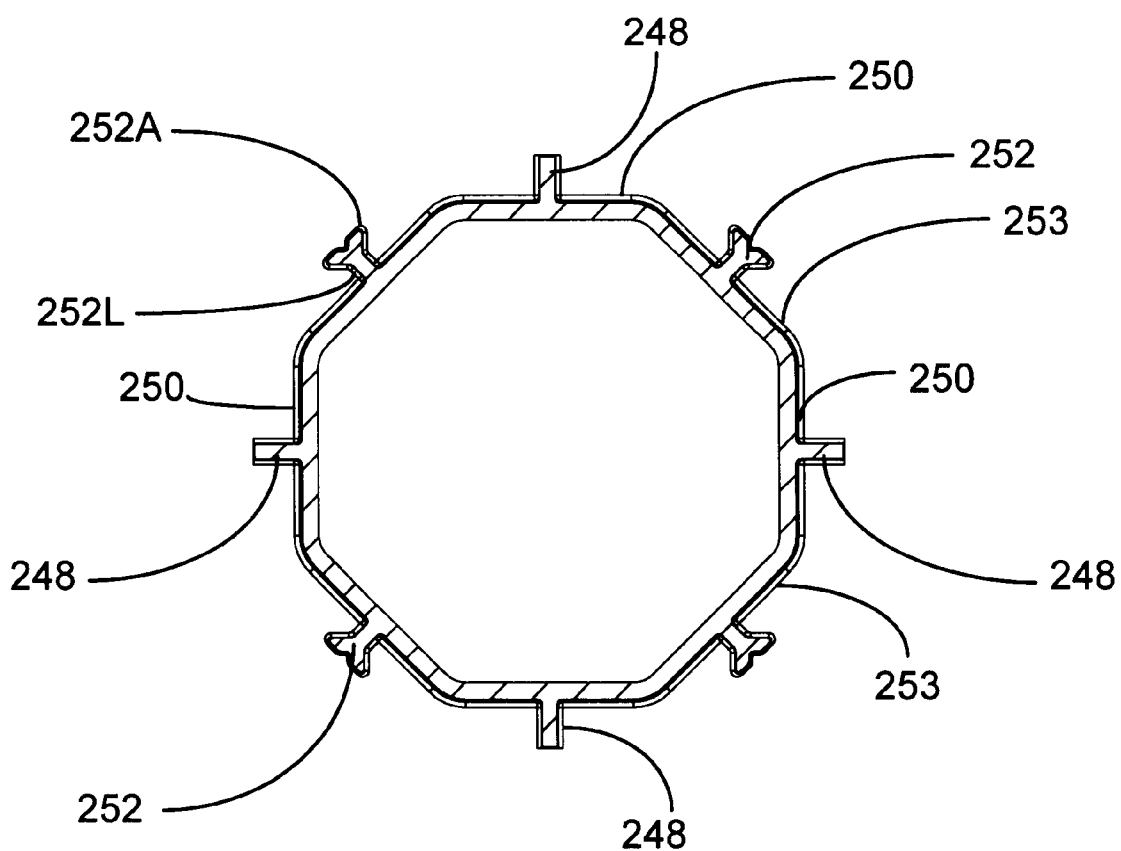

A key feature of broth container 14, as best seen in FIGS. 11B, 11C, and 11D, is two pairs of opposing protruding ribs 248 formed on each of four broth sidewalls 250 and fully extending from top surface 240 to a outer bottom broth container surface 251 of broth container 14. Ribs 248 protrude about ⅛th inch outwards from broth container body sidewalls 250 and provide structural strength to each broth container 14 so that a number of broth containers 14 may be stacked atop one another in broth canisters 24 without collapsing a foil membrane 29 that is adhered over top surface 240 after broth containers 14 are filled with broth solutions. A sealing ridge 241 is provided to aid in adhering foil membrane 29 over the top surface 240 of broth container 14. Because ribs 248 fully extend from top surface 240 to bottom surface 251, when broth containers 14 are stacked atop one another within broth canisters 24 in the common and stable orientation assured by ears 239, both pairs of ribs 248 of next adjacent broth containers 14 are vertically aligned over another pair of ribs 248 and rest on top surface 240 thereby providing structural protection to all broth containers 14 confined within broth canisters 24.

Another key feature of broth container 14, best seen in FIGS. 12A and 11D, is four Y-shaped clamping ridges 252 formed with the leg 252L of the Y-shaped clamping ridges 252 on four of broth container body sidewalls 253 below notches 242 in top surface 240. Arms 252A of the Y-shaped clamping ridges 252 provide an important broth container clamping surface described hereinafter. Clamping ridges 252 partially extend about 50% to 80% of the length of sidewalls 253 towards the bottom surface 251 of broth container 14 and protrude about ⅛th inch outwards from sidewalls 253. FIG. 11D shows two arm-portions 252A and leg-portion 252L of broth clamping ridges 252 so as to provide a vertically oriented recessed surface sized to mate with broth clamping members 109 of broth container handling apparatus 108. FIGS. 21, 21A and 21B illustrate how the clamping members 109 grip two clamping ridges 252 in a pincher action. The two clamping members 109 are moveable relative to one another in a horizontal plane so that the lowermost broth container 14 in broth canister 24 may be securely gripped by broth container handling apparatus 108, removed from the broth canister 24 and presented to pipetting apparatus 46.

Figure 13:
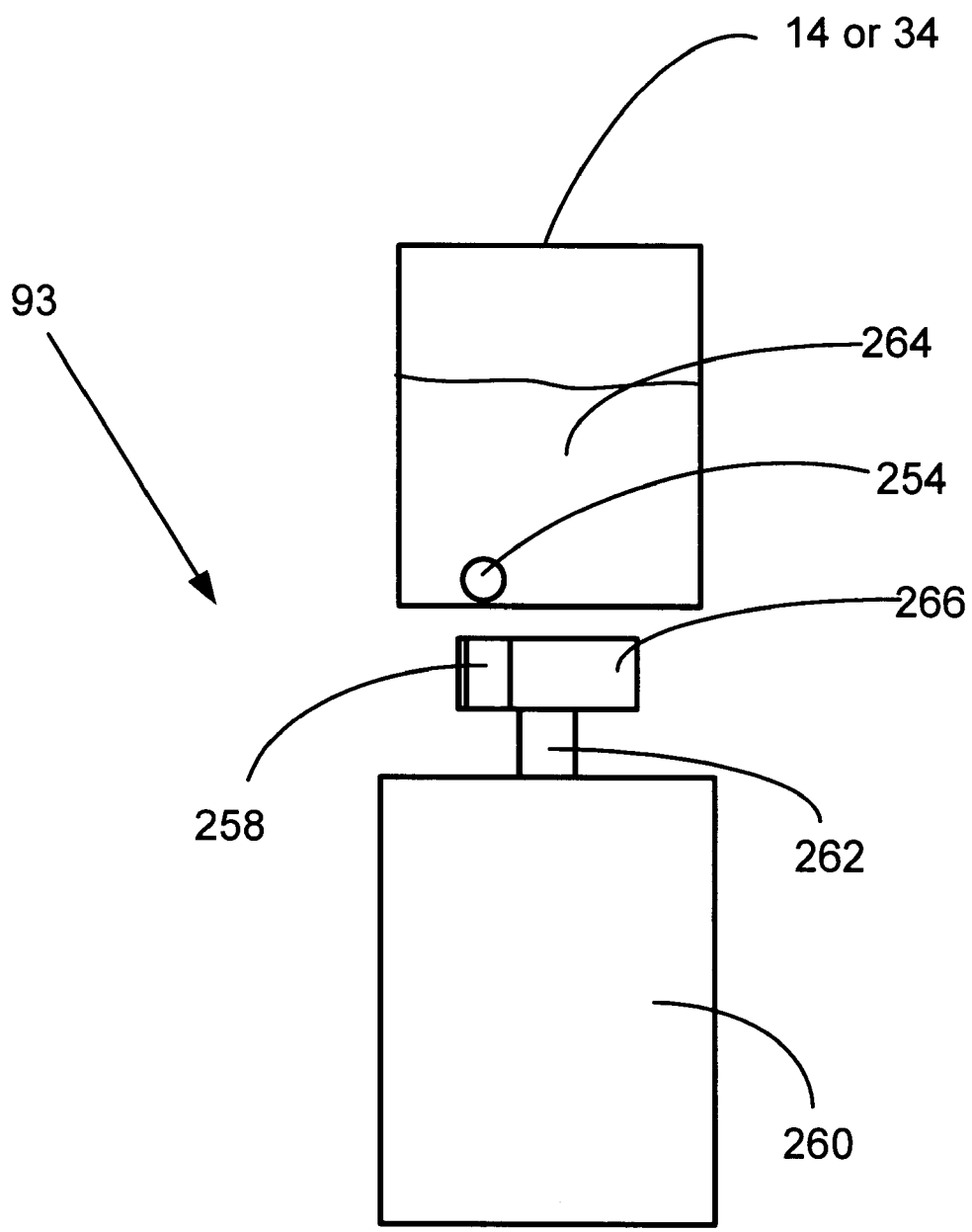
FIG. 13 is a schematic elevation view of a vortex mixer useful within the present invention.

FIG. 13 shows another key feature of broth container 14, or equivalently sample tube 34, as being a freely disposed, ferromagnetic or semi-ferromagnetic mixing member 254 that may be caused to revolve in a generally circular pattern within a broth container 14 or within a sample tube 34 by a vortex mixer 93 described in co-pending U.S. patent application Ser. No. 09/703,139. The mixing member 254 may be caused to rapidly move by revolving an off-center magnetic field source 258 having sufficient magnetic strength at high speed in a generally circular pattern in close proximity to broth container 14 or sample tube 34. When the magnetic field source 258 is revolved as shown beneath broth container 14, the mixing member 254 is caused to move so as to minimize the distance separating the mixing member 254 from the magnetic field source 258. Revolution of the magnetic field source 258 causes the mixing member 254 to revolve within broth/sample solution 264 thereby generating a vortex-like mixing motion of broth/sample solution 264. In the embodiment described, a disk 266 encases magnetic field source 258 as shown. In the exemplary embodiment shown in FIG. 13, the magnetic field source 258 comprises a permanent or semi-permanent magnet 258 and magnetic mixing member 254 is caused to revolve by rotating the permanent or semi-permanent magnet 258 at close proximity to the broth container 14 using a mixing motor 260 with a mixing motor shaft 262 having the disk 266 attached thereto. The term ferromagnetic is intended to mean a substance having a sufficiently high magnetic permeability to be positionally affected by an orbiting or rotating magnetic field.

Figure 14A:
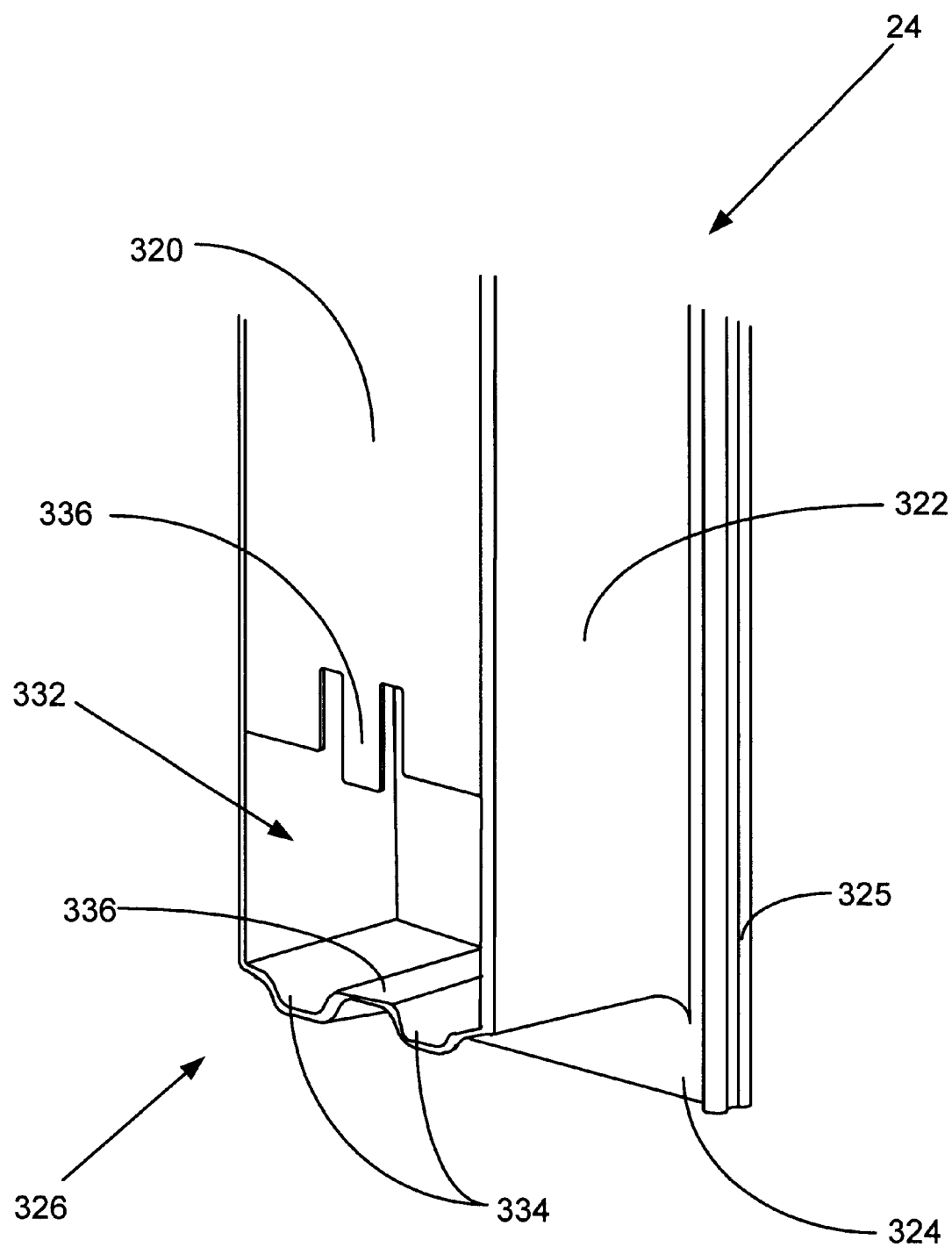
FIG. 14A is an enlarged perspective view of the broth canister of FIG. 14.
Figure 14B:
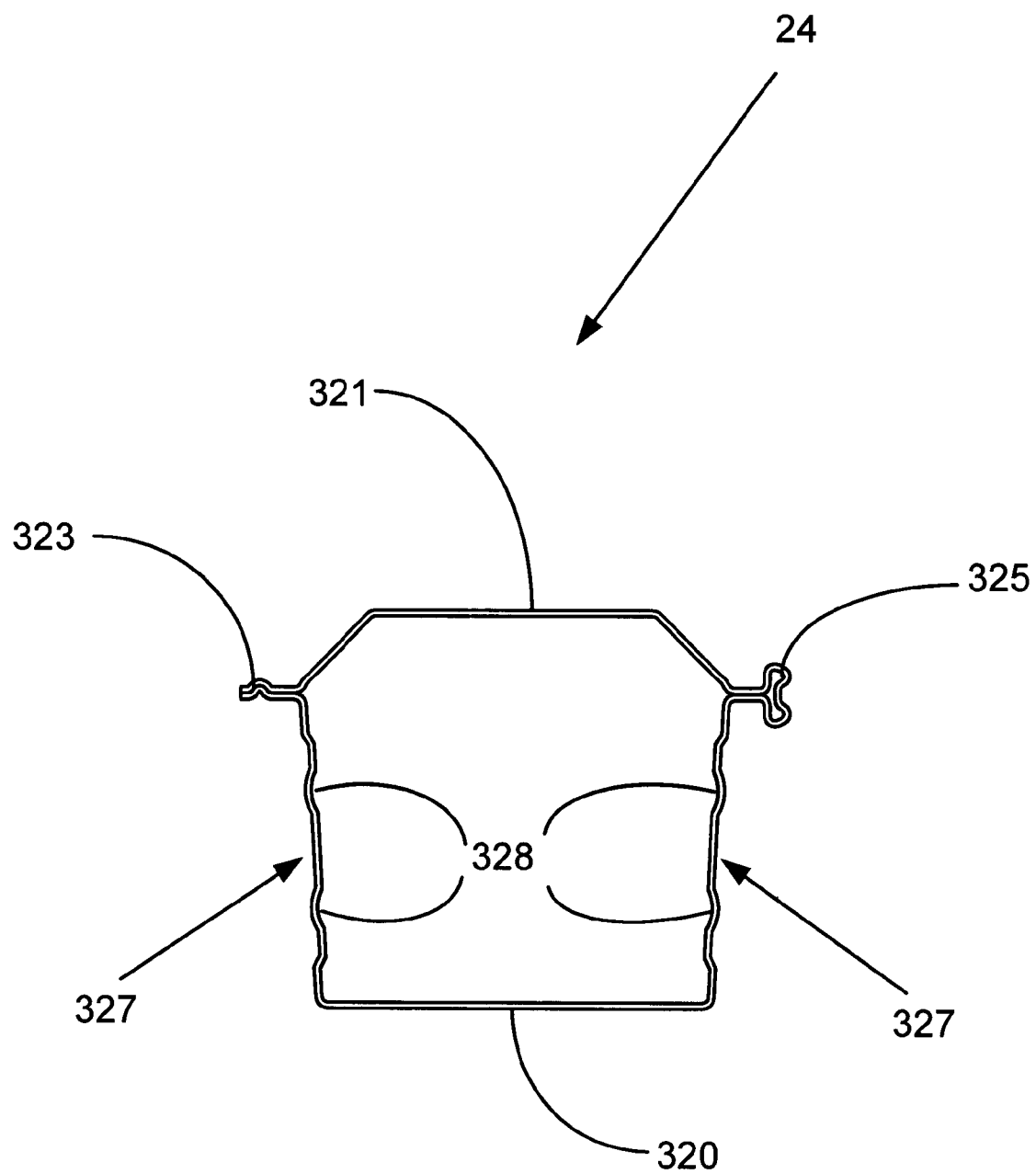
FIG. 14B is a sectional view of the broth canister of FIG. 14.

FIG. 14 is a perspective view of a closed elongate broth canister 24 having a generally rectangular cross-section (FIG. 14D) formed by a broth canister front wall 320, ID canister back wall 321 and two ID canister side walls 322, the front wall 320, back wall 321 and side walls 322 of essentially similar dimensions so that a squarely shaped interior is formed to house a plurality of broth containers 14 stacked one atop another. A top end portion 324 and a bottom end portion 326 close the ends of broth canister 24. Typically, broth canister 24 is formed as an indented sheet of plastic and is folded in half creating a external rib 325 extending the full length of broth canister 24 between broth canister back wall 321 and a side wall 322 (FIG. 14B). An opposed elongate broth canister seal flange 323 is created in a sealing operation and also extends the full length of broth canister 24 between broth canister back wall 321 and a side wall 322. A number of surface bumps 328 are formed in opposing pairs of finger pads 327 formed in top end portion 324 to facilitate handling of a broth canister 24 by an operator. FIG. 14B is a sectional view of broth canister 24 and best illustrates the broth canister seal flange 323, broth canister external rib 325 and internal ribs 328.

Key features of the broth canister 24 include a broth canister mounting flange 324 shaped to seat into a mounting groove 331 (FIG. 1) within B/ID chamber 28 so that a broth canister 24 may be placed using a number of finger pads 327 in a vertical position whereat two spring-loaded latching cams within B/ID chamber 28 snap over latch steps 329 formed at opposing ends of a latching flange 330 extending upwardly above top end portion 324. The portion of latching flange 330 between steps 328 is confined between spring-loaded latching cams to provide proper vertical orientation. FIG. 14A is an enlarged view of the bottom end portion 326 of broth canister 24 showing details of a broth eject port 332 formed in broth canister front wall 320 proximate mounting flange 324 and sized to allow the lowermost broth container 14 within the plurality of broth containers 14 stacked one atop another to be pulled out of broth canister 24. Broth containers 14 may be pulled out of broth canister 32 through broth eject port 332 by broth clamping members 109 located at the end of moveable broth arms 238 of broth robotic device 108 (FIG. 21). Broth eject port 332 has the shape of a rectangular opening formed between a pair of depressions 334 having a flat portion 336 between the depressions 334. The flat portion 336 functions as a horizontal broth container sliding surface to support broth containers 14 as they are pulled out of broth canister 24 through broth eject port 332. A tongue flap projection 338 formed in front wall 320 extends downwardly and partially into the eject port 332 to prevent broth containers 14 from being dislodged accidentally from canister 24 and also to prevent broth containers 14 from being improperly inserted back into canister 24.

FIGS. 15A–15M illustrate the operation of sample pipetting and transport system 60 of FIG. 3 in filling the AST test arrays Of FIG. 5 in the previously mentioned AST carrier 74 "build and fill" process. FIGS. 15A–15L are simplified so as to clearly illustrate important improvements in high speed filling of AST test arrays 12 and AST test microwells 124 with liquid sample aspirated from sample tubes 34 by pipetting apparatus 46, and are an important advantage of the present invention, being derived from the single pipetting apparatus 46 being operational in two opposed directions along the single linear path defined by the loci L of positions 46a–46e as defined above such that AST test arrays 12 may be filled with sample-inoculum at a plurality of positions along loci L.

Figure 15B:
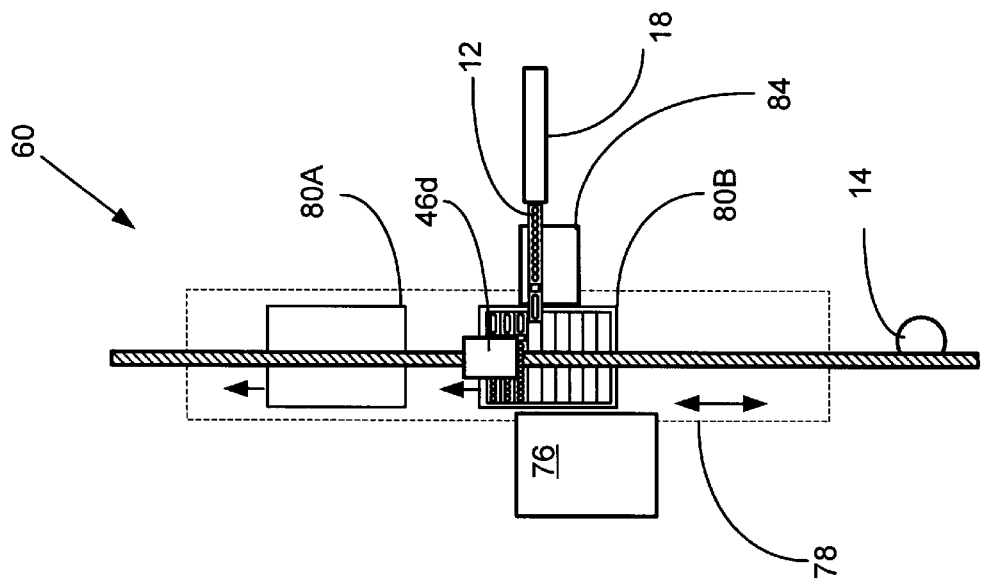
FIGS. 15A–H, J–M illustrate the functions of the sample pipetting and transport system of FIG. 3 in filling the AST test arrays of FIG. 5.
Figure 15A:
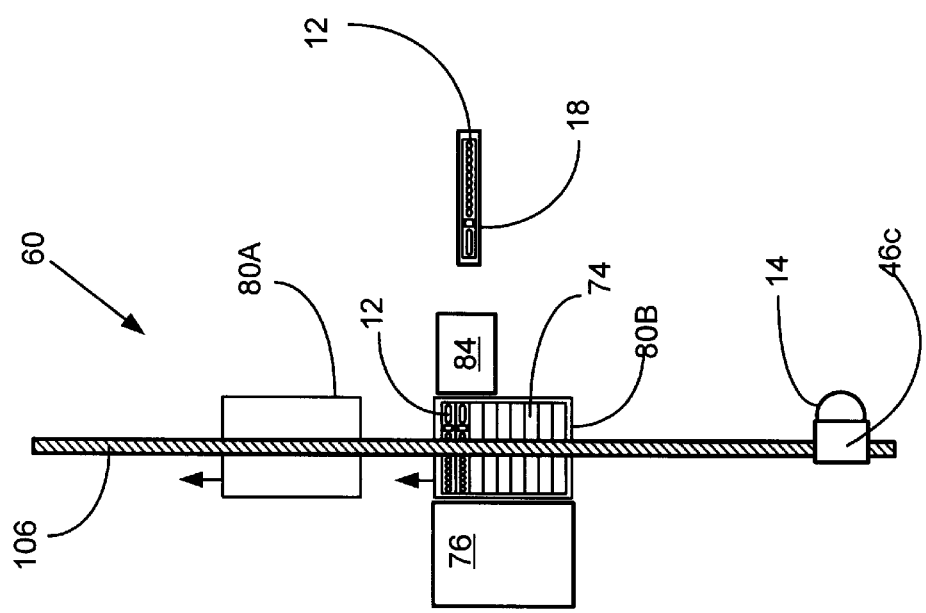
Figure 15D:
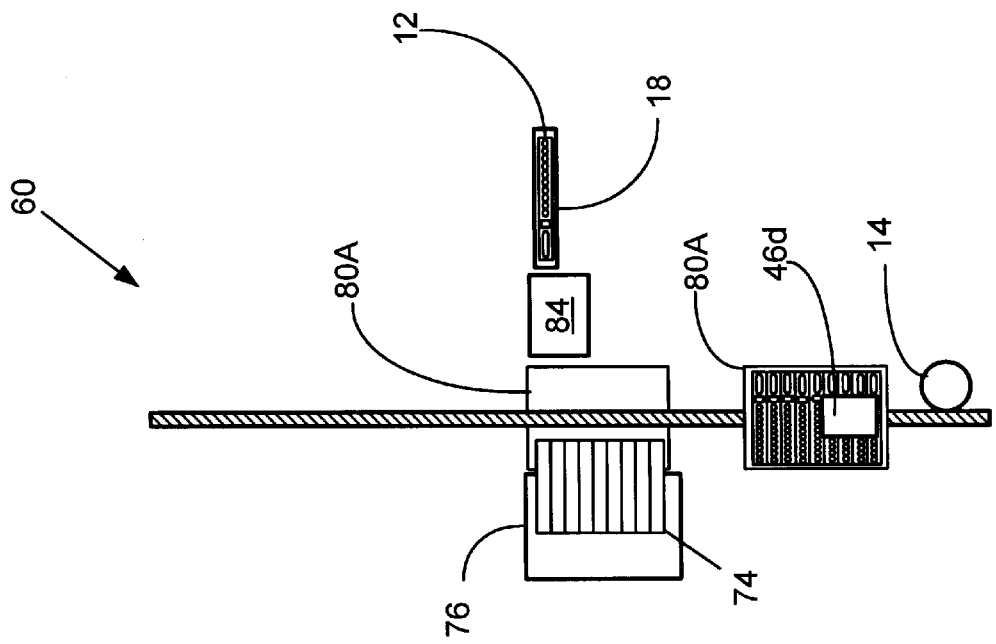

Beginning with FIG. 15A, an AST carrier 74 partially loaded with AST test arrays 12 and supported on AST array carrier bed 80B is seen positioned between AST carrier transporter 76 and AST array dispenser 84. In these FIGS., two identical AST array carrier beds are identified as 80A and 80B for purposes of discussion. AST array carrier bed 80A is seen as being empty in FIG. 15A. As discussed earlier, AST array dispenser 84 is adapted to remove AST test arrays 12 from an AST canister 18 in the form of a singulated stream and to successively place the AST arrays 12 within a number of empty AST array slots 86 formed within an AST carrier 74 as the AST carrier 74 is advanced along a first direction on carried by AST array carrier bed 80B (arrow pointing "upwards" in FIG. 15A for purposes of illustration) as controlled by CPU 15. As indicated by the "upwards" direction of movement arrows, hereinafter called the "upwards direction" the empty AST carrier bed 80A is seen "ahead" of AST carrier 74 on the AST array carrier bed 80B that is partially loaded with AST test arrays 12. The purpose of FIGS. 15A–15M is to describe how high speed filling of AST test arrays 12 is accomplished as a result of the pipetting apparatus 46 operating in two opposed directions along the loci L defined by positions 46a–46e taken with AST test arrays 12 being filled with sample-inoculum at a plurality of positions also along loci L. For purposes of clarity, AST array carrier transport 78 is shown only once in dashed lines in FIG. 15B and its two directions of travel are as indicated by a double-ended arrow even though the AST array carrier transport 78 is in each of FIGS. 15A–15M.

FIG. 15B illustrates a subsequent stage of loading AST carrier 74 with AST arrays 12, a stage in particular whereat a fourth AST array 12 is being loaded onto AST array carrier 74; pipetting apparatus 46, having aspirated an amount of inoculum-broth solution from a broth container 14, is at position 46d and deposits a known amount of inoculum-broth solution into reservoir 134 of the first AST test array 12 loaded onto AST array carrier 74. As described before, pipetting apparatus 46 is controlled by CPU 15 between a third position, 46c, for aspirating a known amount of inoculum-broth solution from broth container 14 after the sample and broth are properly mixed together and a fourth position, 46d, for depositing a known amount of sample and broth into an AST test array 12. As will be described in conjunction with these FIGS. 15A–15M, pipetting apparatus 46 "chases" AST array carrier 74 upwards or downwards as required so as to deposit inoculum-broth into all AST test arrays 12 carried by AST array carrier 74, eliminating the requirement that AST arrays 12 be filled at a stationary position(s). Because pipetting apparatus 46 "chases" AST array carrier 74 to deposit inoculum-broth into the AST test arrays 12 carried thereby, an unnecessary need for extensive movement of pipetting apparatus 46 is eliminated, thereby reducing the total time required for AST arrays 12 to be filled and increasing throughput of analyzer 10. It should be understood that pipetting apparatus 46 can begin to deposit inoculum-broth solution into the reservoir 134 of an AST test array 12 as soon as the first AST test array 12 is loaded onto AST array carrier 74.

Figure 15C:
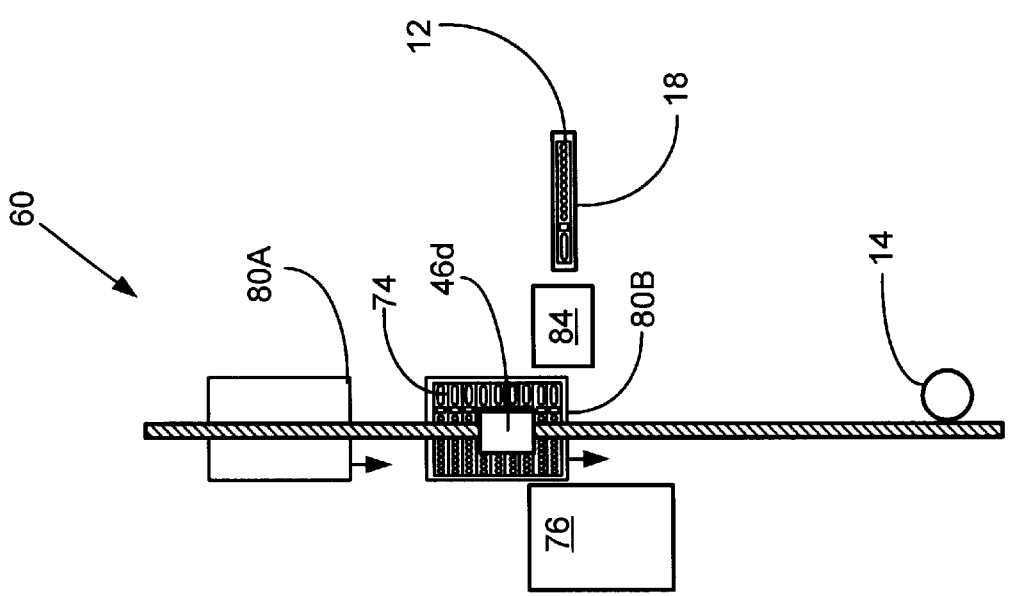

This process continues until the requested number of AST arrays 12 are loaded into AST array slots 86 formed within AST array carrier 74 at which stage the direction of motion of AST array carrier transport 78 reverses to a direction opposite the "upwards" direction, as indicated by the "downwards" direction of movement arrows, hereinafter called the "downwards direction", in FIG. 15C. AST array carrier transport 78 continues in the downwards direction of movement until the empty AST array carrier bed 80A is aligned with AST carrier transporter 76 at which stage, FIG. 15D, AST array carrier transport 78 is stopped and an empty AST carrier 74 is moved by AST carrier transporter 76 onto AST array carrier bed 80A. At this stage, the direction of motion of AST array carrier transport 78 reverses once again to the "upwards direction" (FIG. 15E). The empty AST array carrier 74 is obtained by AST carrier transporter 76 from within a number of similar an empty AST carriers 74 made available within AST incubation and analysis chamber 70. During this time, pipetting apparatus 46 continues to "chase" AST array carrier 74 and deposit at the "moving" position 46d a known amount of inoculum-broth into the AST test arrays 12 on the AST array carrier 74 until all AST arrays 12 are filled.

Figure 15F:
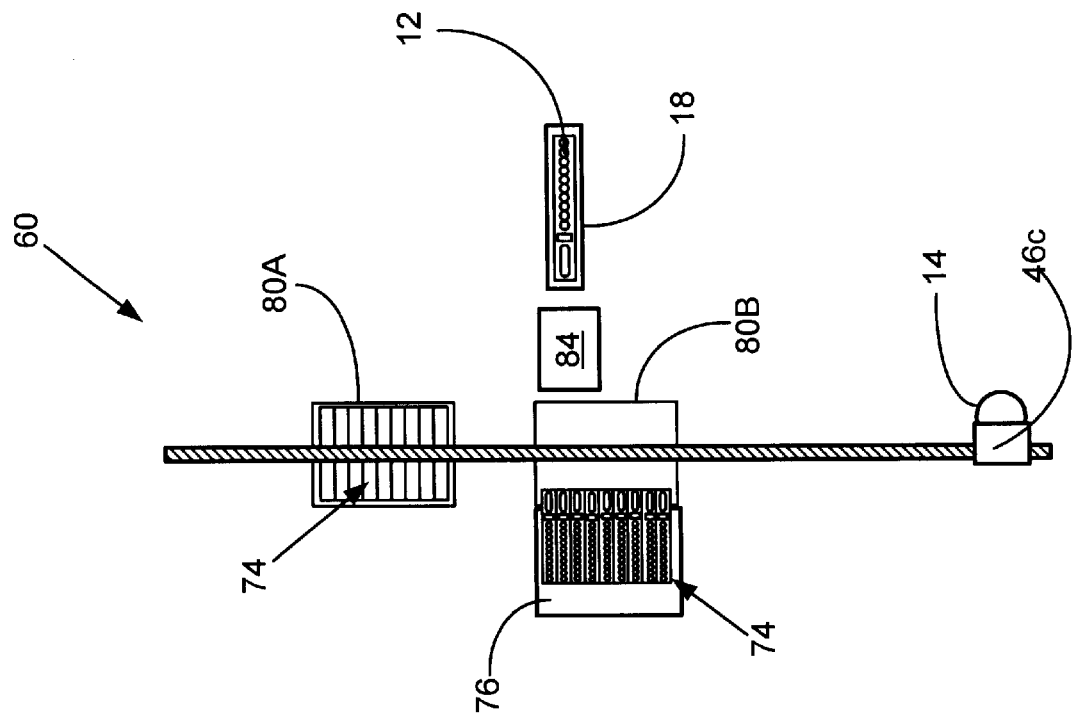
Figure 15E:
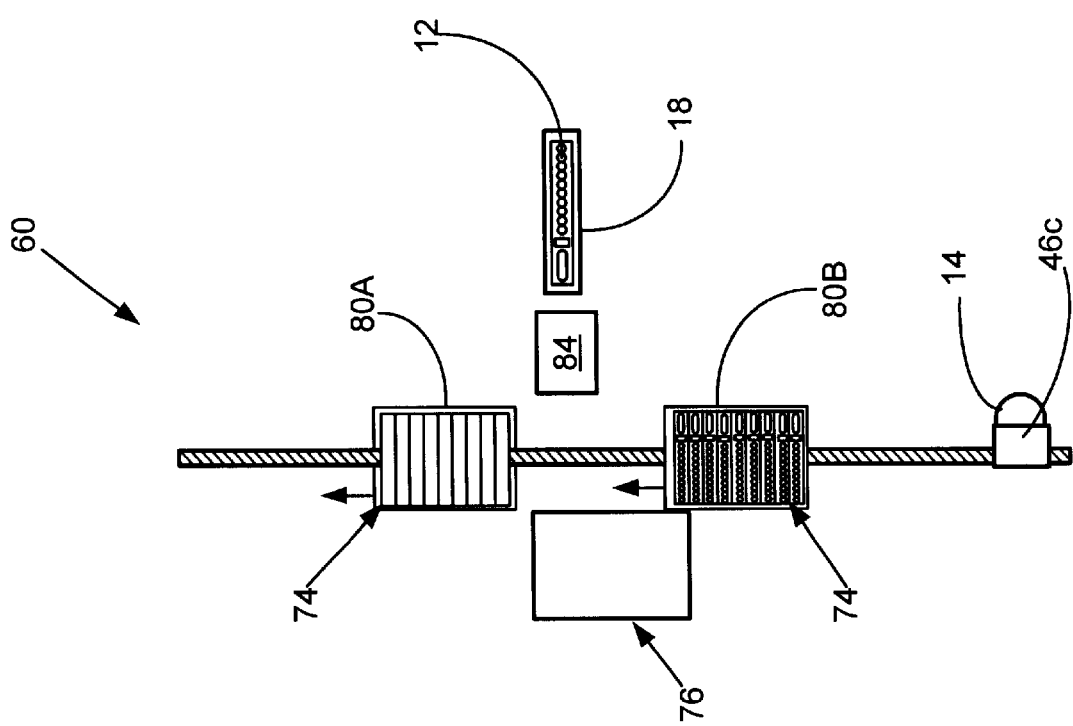
Figure 15H:
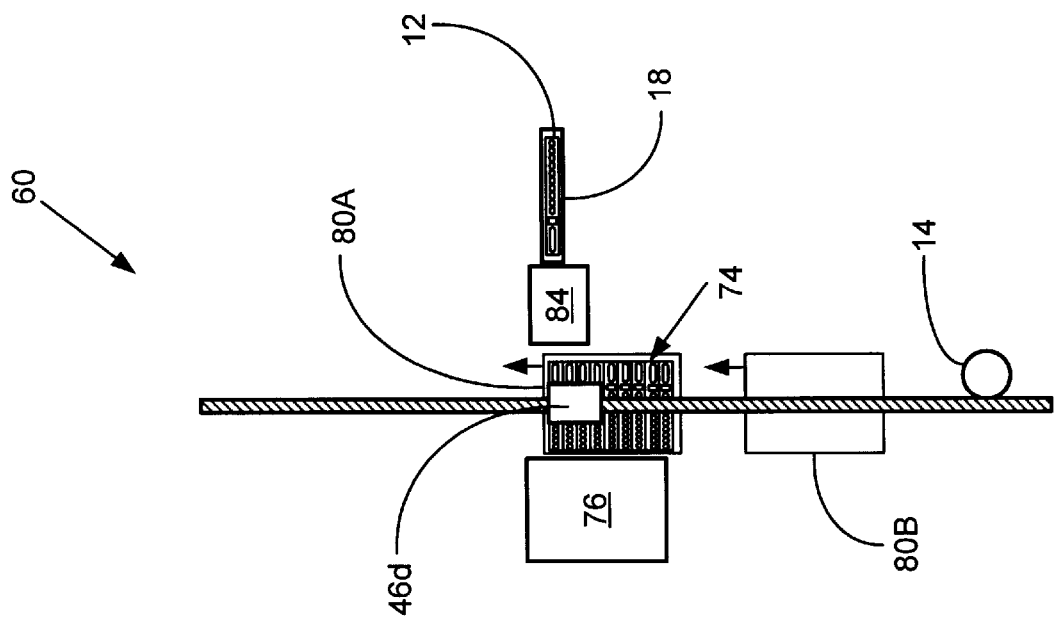
Figure 15G:
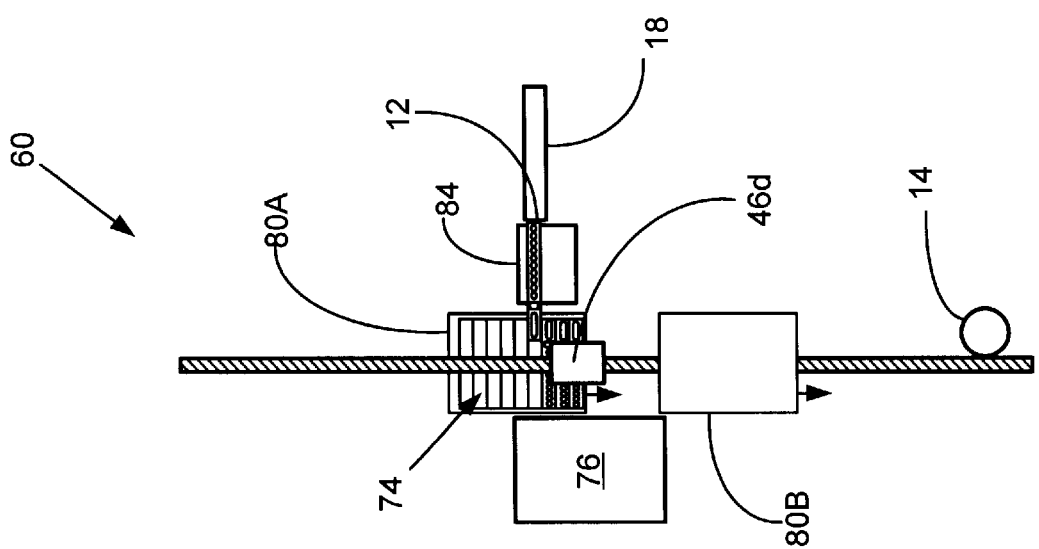

This movement in the "upwards direction" continues until the AST array carrier 74 having all filled AST arrays 12 is in alignment with AST carrier transporter 76 at which stage, FIG. 15F, AST array carrier transport 78 is stopped and AST carrier transporter 76 removes an AST array carrier 74 from AST array carrier bed 80B and lowers the AST array carrier 74 through AST transport opening 81 in operating plate 11 to a lowermost position whereat the AST carrier transporter 76 deposits the AST array carrier 74 into the AST vacuum filling station 82 positioned on the lower base plate 13. After depositing AST array carrier 74 in the AST vacuum filling station 82, AST carrier transporter 76 moves vertically along AST transport rod 83 to an AST incubation rack 72 and removes an unloaded AST carrier 76 from AST incubation and analysis chamber 70 through opened side portion 73 formed in the exterior wall of the AST incubation chamber 60. When AST carrier transporter 76 removes AST array carrier 74 from AST array carrier bed 80B, the direction of motion of AST array carrier transport 78 reverses once again to the "downwards direction" (FIG. 15G) so that the previously unloaded AST array carrier 74 may be loaded with AST arrays 12 by AST array dispenser 84 as shown. As before, as soon as a single AST test array 12 has been loaded onto AST array carrier 74, pipetting apparatus 46 "chases" AST array carrier 74 to deposit inoculum-broth into the AST test arrays 12 carried thereby. This process continues until the stage depicted in FIG. 15H is reached, when all AST array slots 86 within AST array carrier 74 are filled at which stage the direction of motion of AST array carrier 74 reverses to the "upwards direction". (For clarity, there is no FIG. 15I.)

Figure 15K:
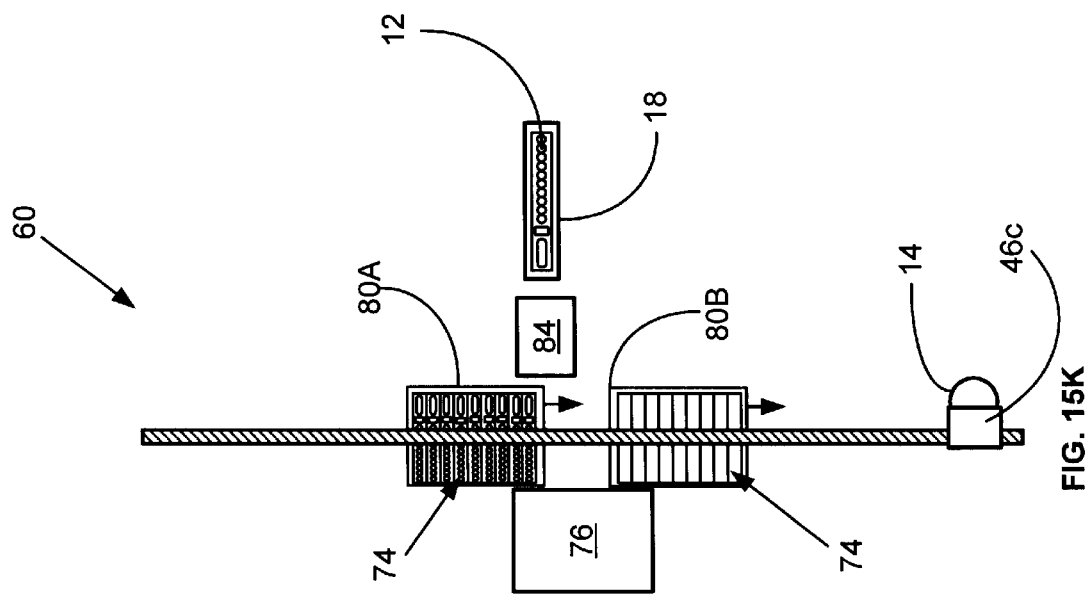
Figure 15J:
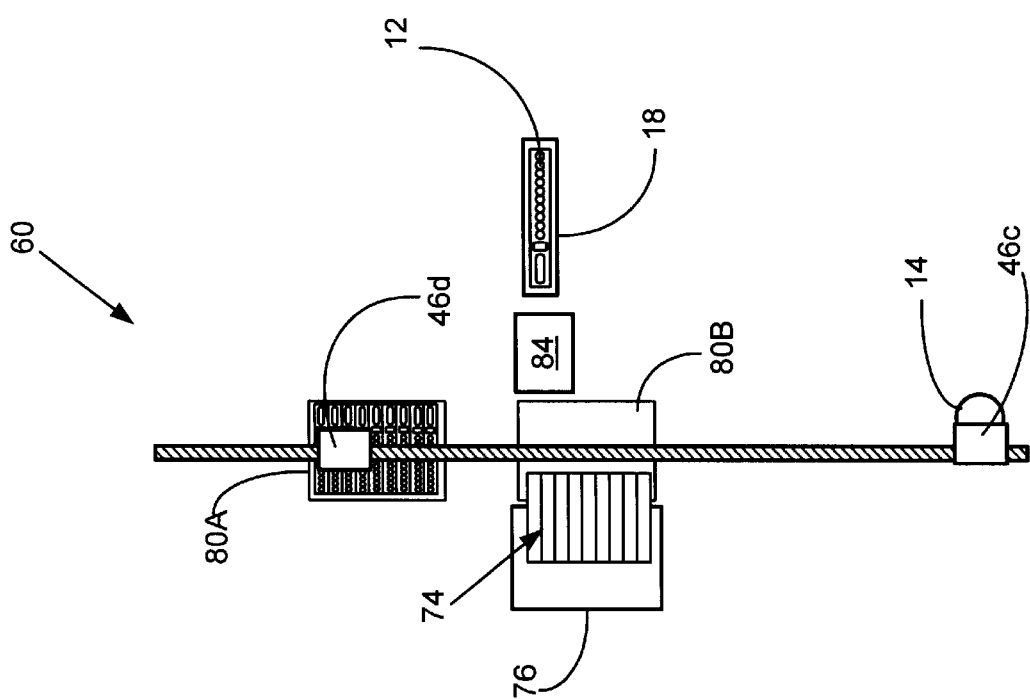
Figure 15M:
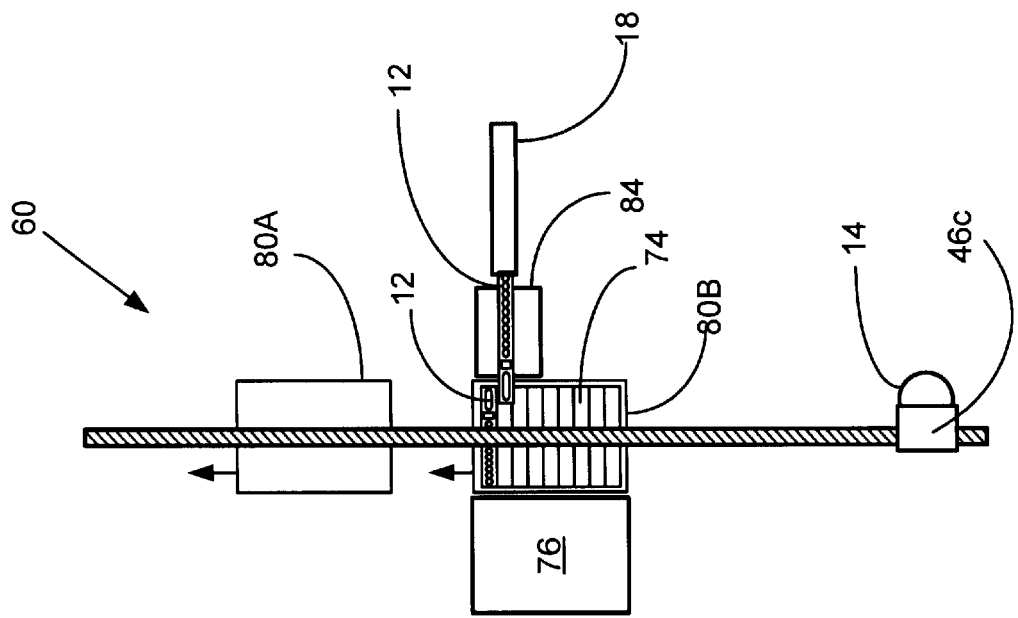

Filling of AST arrays 12 on AST array carrier 74 by pipetting apparatus 46 continues until the empty AST array carrier bed 80B is in alignment with AST carrier transporter 76 at which stage, FIG. 15J, AST array carrier transport 78 is stopped and an unloaded AST array carrier 74 is placed on empty AST array carrier bed 80B by AST carrier transporter 76, and the direction of motion of AST array carrier transport 78 reverses once again to the "downwards direction" (FIG. 15K). During this stage, as soon as a single AST test array 12 has been loaded onto AST array carrier 74, pipetting apparatus 46 "chases" AST array carrier 74 to deposit inoculum-broth into the AST test arrays 12 carried thereby. FIG. 15K illustrates an important portion of the movements during which pipetting apparatus 46 is at fixed position 46c to aspirate inoculum-broth solution from broth container 14 as it also "chases" AST array carrier 74.

Figure 15L:
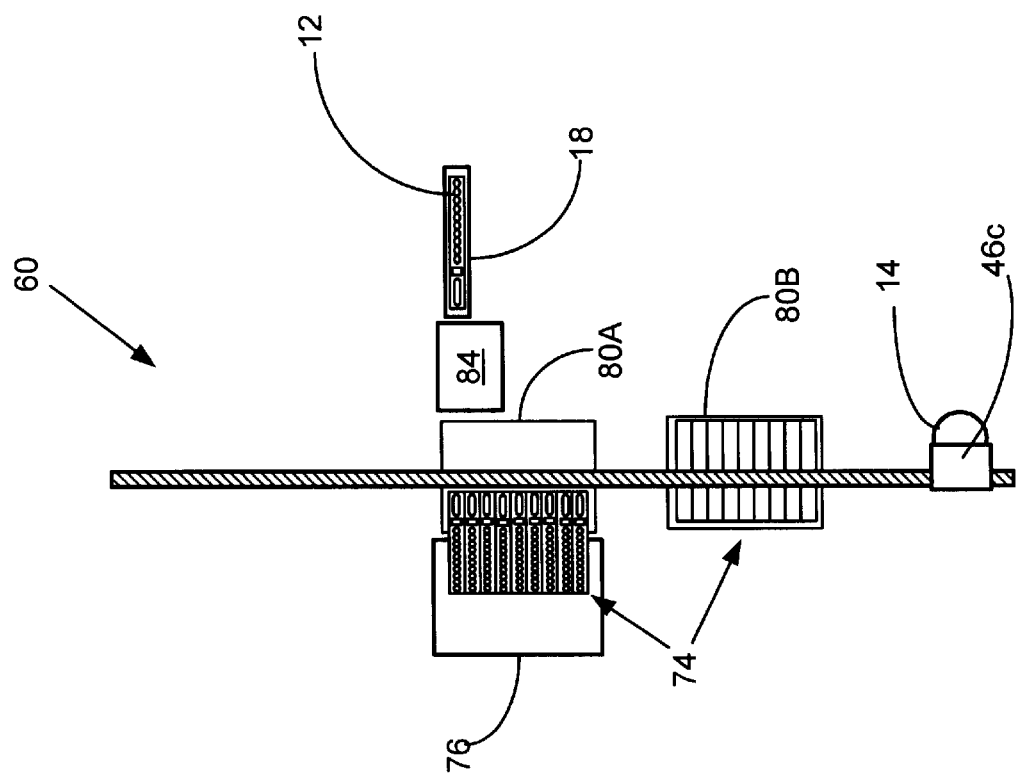

Movement in the "downwards direction" continues (FIG. 15K) until the AST array carrier 74 having all filled AST arrays 12 is in alignment with AST carrier transporter 76 at which stage, FIG. 15L, AST array carrier transport 78 is stopped, the AST array carrier 74 is removed by AST carrier transporter 76; the direction of motion of AST array carrier transport 78 reverses once again to the "upwards direction" so that the unloaded AST array carrier 74 on 80B may next be loaded with AST arrays 12 by AST array dispenser 84.

As before the AST array carrier 74 loading process begins and as soon as an unfilled AST array 12 is positioned upon AST array carrier 74, pipetting apparatus 46 begins depositing a known amount of inoculum-broth into an AST test array 12. This situation exactly replicated the AST array loading and filling stage of FIG. 15A enabling the AST array filling process to continue without stopping by automatically proceeding to the AST array 12 filling stages depicted by FIGS. 15A–M.

It should be understood that the feature of analyzer 10 in which a single pipetting apparatus 46 operational in two opposed directions along a single linear path defined by the loci of positions 46a–46d as defined above provides a degree of compactness in layout in addition to minimizing the amount of time required in the AST array filling process.

Figure 19:
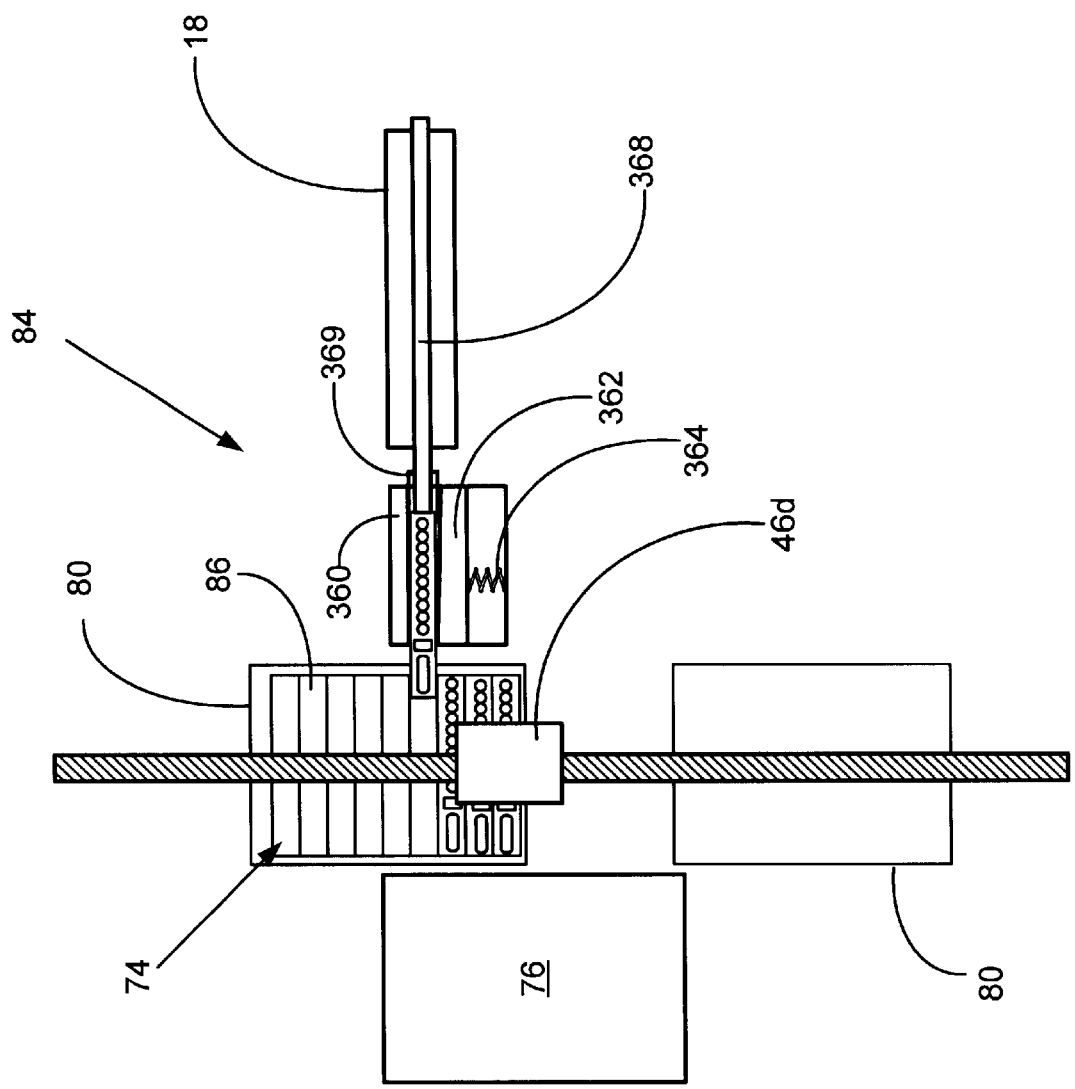
FIG. 19 is a top plan view of an AST array dispenser useful within the present invention.

FIG. 19 illustrates AST array dispenser 84 adapted to remove or eject AST test arrays 12 from an AST canister 18 in the form of a singulated stream of AST test arrays 12 and to successively place each of the AST arrays 12 within an empty AST array slot 86 formed within an AST array carrier 74. AST array dispenser 84 comprises a pushrod 368 controlled by CPU 15 to displace an AST array 12 from an AST canister 18 and into contact with an array alignment wall 360 and between the alignment wall 360 and an array guide 362 to precisely position the lowermost AST test array 12 within an empty parallel slot 86 in an AST array carrier 74. Array guide 362 is biased towards array alignment wall 360 by array guide spring 364 to maintain alignment of an AST array 12 being moved from an AST canister 18 into an empty AST array slot 86 during the process of loading AST arrays 12 onto a AST array carrier 74. An AST array lifter 369 is also located below and between the alignment wall 360 and the array guide 362 to lift an AST array 12 above the base 75 of carrier 74 (FIG. 17) as the AST array 12 is placed within an empty AST array slot 86 in order to protect the layer of adhesive film along the bottom surface 120 of AST array 12 previously mentioned.

FIG. 20 illustrates one of several alternate embodiments of a AST carrier transport 78 adapted to transport an empty AST carrier bed 80 or an AST carrier bed 80 having an AST array carrier 74 totally filled with AST arrays 12 or partially loaded with AST arrays 12 during the loading process of FIG. 15. In one embodiment, AST carrier transport 78 comprises at least one AST carrier transport take up roller 380 which drives a belt 382 in two directions along a linear path over upper operating plate 11 as illustrated in FIG. 15. Both AST carrier beds 80 are fastened to the AST carrier transport belt 382 using pins 386. AST carrier transport belt 382 is moved along a linear path beneath sample pipetting and delivery system 60 during which movement AST carriers 74 may be loaded with AST arrays 12, and AST arrays 12 may be filled with a known amount of inoculum-broth by pipetting apparatus 46 at position 46d. Alternate embodiments of AST carrier transport 78 include use of a lead screw-driven follower to support AST carrier beds 80.

The ID robotic device 50 (FIG. 16) typically comprises a computer controlled motor-driven apparatus adapted for movement in x-y-z, and radial directions so as to move ID rotors 16 within analyzer 10 as previously described. Device 50 may take on many alternate designs but typically includes rack and pinion gears 222 and/or a rotating gear mechanism 56 to control the clamping of and movement of ID rotors 16. An important feature of device 50 is at least one pair of clamping teeth 226 located at the end of moveable arms 58 and maintained by a tension spring 57 to provide a spring-activated normally-closed incisor force. Clamping teeth 226 are sized to fit into troughs 192 and 194 and thereby secure ID rotor 16 for movement as required within analyzer 10. In the event of a power failure, any ID rotor 16 held within clamping teeth 226 is retained securely because of normally-closed, spring-activation clamping action of device 50. Flexible and secure transportation of an ID rotor 16 between the automated stations of analyzer 10 is made possible by the presence of troughs 192 and 194 as the ID rotor 16 may be thereby constrained by any number of differently designed robotic devices 50.

ID robotic device 50 is further adapted to remove ID test rotors 16 from the filling and centrifuging apparatus 52 (when centrifuging apparatus 52 is positioned within the ID incubation chamber 48) to either a rotor holding frame 228 or to ID rotor optical analyzer 230 both of which are located within the ID incubation and analysis chamber 48 (FIG. 1). ID robotic device 50 is additionally adapted to move ID test rotors 16 from a rotor holding frame 228 to a rotor disposal station 49 within the ID incubation chamber 48. In an exemplary embodiment, as many as four rotor holding frames 228 may be attached to the interior walls of the ID incubation chamber 48 and as many as twenty ID test rotors 16 may be mounted within each rotor holding frame 228. Typically, rotor holding frames 228 are horizontally oriented C-clamp shaped pieces of spring metal in which the ears of the holding frames 228 are adjusted to provide an interference fit between the holding frames 228 and an ID rotor 16.

The broth container handling apparatus 108 (FIG. 21) typically comprises a computer controlled rack and gear system 234 to control the clamping of and movement of broth containers 14. An important feature of broth container handling apparatus 108 is at least one pair of clamping teeth 109 located at the end of moveable arms 238 and maintained by a tension spring 236 to provide a spring-activated normally-closed incisor force. Clamping teeth 109 are sized to fit over the arm portion 252A of the Y-shaped clamping ridges 252 as seen in FIG. 21B and thereby secure broth containers 14 for movement as required within analyzer 10.

FIG. 21A shows the automatic opening action of teeth 109 as arms 238 are advanced towards a broth container 14 and moved outwards as the teeth 109 ride over the arm portion 252A of the Y-shaped clamping ridges 252. In the event of a power failure, any broth container 14 held within clamping teeth 109 is retained securely because of normally-closed clamping action of device 108. A pair of tapered cams 370 are shown on arms 238 so that when an used broth container is to be disposed in a trashing chute (not shown), arms 238 may be spread by a pair of mating rollers (not shown) and broth container 14 released into the chute. A slotted keeper 111 is seen as retaining a protruding rib 248 on broth sidewalls 250 so that a broth container 14 is held between arms 238 during the disposal process and not allowed to cling to either of the teeth 109. Flexible and secure transportation of a broth containers 14 between the automated stations of analyzer 10 is made possible by the presence of the Y-shaped clamping ridges 252 in conjunction with teeth 109 as the broth containers 14 may be transported by any number of differently designed robotic devices 108.

The ID rotor optical analyzer 230 may have several embodiments but typically comprises a fluorometric reader similar to that used in the MicroScan "WalkAway® microbiology analyzer sold by Dade Behring Inc., Deerfield, Ill. U.S. Pat. Nos. 4,676,951, 4,643,879, 4,681,741 and 5,645,800 describe certain features of the WalkAway® analyzer. The ID rotor optical analyzer 230 typically includes a pair of stationary reading heads that reside above the two annular arrays of test microwells 178 and 182 in ID rotor 16 when rotor 16 is placed within ID rotor optical analyzer 230. Each reading head encloses a fluorometer having a source that directs interrogating radiation to an excitation filter through a light path. A pair of lenses or dichromatic beam splitters direct the outcoming radiation onto sample contained either in microwells 178 or 182 within ID rotor 16. The microwell is preloaded with a material that, in the presence of a target microorganism within sample fluids displaced into the microwells as described hereinafter, reacts to the light energy by fluorescing. The resulting fluorescence is directed by lenses or mirrors to an emission filter for the expected wavelength. Solid state detectors capture the fluoresced light signal from each of wells 178 or 182 as the ID rotor is rotated below the reading heads and translate the light signal into an output that is proportional to the amount of fluorescence detected. Measured signals are transmitted to the on-board CPU computer 15 so that the pattern of signals emanating from the microwells 178 and 182 may be compared with signal patterns of known microorganisms. The identity ID of any microorganisms within the sample may thereby be determined.

ID rotor filling and centrifuging apparatus 52 (FIG. 22) comprises a moveable arm 206 mounted to a rotatable support 208 rotated by a CPU 15 computer-controlled motor 210 so that arm 206 may be rotated in a plane between ID incubation and testing chamber 48 and rotor filling and centrifuging position 46e located along loci L serviced by sample pipetting and transport system 60. An important feature of the filling and centrifuging apparatus 52 is a centrifuging module 212 adapted to both provide rotational motion to an ID rotor 16 mounted within a ID rotor clamping mechanism 214 and to present an ID rotor 16 to pipetting apparatus 46 at the fifth position, previously identified as 46e, in order that a known amount of sample may be deposited into an ID test rotor 16. Centrifuging module 212 typically comprises a centrifuging motor 216 capable of rotating ID rotor 16 via a centrifuging belt drive 218 at an initial relatively low speed in the range of about 200 to 400 RPM and also at a relatively high speed in the range of about 3,500 to 4,500 RPM. ID rotor clamping mechanism 214 is adapted to grasp ID rotor 16 at its periphery when the ID rotor 16 is pushed horizontally onto centrifuging module 212 or to secure ID rotor 16 with latches if the rotor 16 is moved vertically into centrifuging module 212. As described later, liquid sample is initially loaded into rotor 16 in a low RPM operation and then moved to microwells 178 and 182 in a higher RPM operation. Centrifuging module 212 is also operable so that after an ID rotor 16 is loaded with sample, arm 206 may be rotated from rotor filling and centrifuging position 46e back into ID rotor optical analyzer 230 within ID incubation and testing chamber 48 and rotated slowly during the optical analysis process. Motor 216 that enables the rotational functions of centrifuging module 212 are known in the art as variable speed motors and are commercially available from a number of sources.

During operation of analyzer 10, patient samples to be tested have bar-coded identifying indicia from which the ID and AST tests that are desired to be accomplished may be identified. Analyzer 10 is programmed using well-known computer-based programming tools to automatically perform the appropriate sample and reagent handling protocols. Computer CPU 15 is programmed to automatically determine a particular ID canister 32 having the appropriate ID test rotors 16 required to complete the requested ID protocol (s), to rotate B/ID carousel 26 to present the appropriate ID canister 32 to the robotic device 50. Robotic device 50 removes an ID test rotor 16 from the selected ID canister 32 by gripping the troughs 192 and 194 using clamping teeth 226, moves the selected ID test rotor 16 into ID incubation chamber 48 and then loads the rotor 16 onto the filling and centrifuging apparatus 52. At the same time, sample pipetting and delivery system 60 is controlled by CPU 15 to make available at position 46e the required amount of sample for the ID protocol to be performed. Filling and centrifuging apparatus 52 next moves ID test rotor 16 into position 46e where sample for the ID protocol is deposited into rotor 16 through opening 213 in tape 211.

While the rotor 16 is loaded with sample, centrifuging module 212 portion of filling and centrifuging apparatus 52 is activated to rotate ID rotor 16 at an initial relatively low speed in the range of about 200 to 400 RPM for a period of time in the range 1–3 seconds during which sample is moved away from the centermost portion of surface 176 and upwards along surface 188. The centrifuging module 212 is next activated to rotate ID rotor 16 for a period of time in the range 5–15 seconds at a speed in the range of about 3,500 to 4,500 RPM during which sample is moved through microchannels 180 and 184 into microwells 178 and 182 respectively. Subsequent to this loading and filling operation, rotation of ID rotor 16 is stopped, ridge 217 acts as a barrier to retain excess sample portion which is sacrificially evaporated over time thereby eliminating evaporation of sample within microchannels 180 and 184 and microwells 178 and 182.

Filled IR rotors 16 are next moved back into ID incubation and test chamber 48 by filling and centrifuging apparatus 52 where rotors 16 may be initially read by ID rotor optical analyzer 230. Robotic device 50 then places IR rotors 16 into incubation frames 228 for various periods of time, depending on the particular ID test protocol being performed by analyzer 10 under control of CPU 15. As is known, during incubation, fluorescence signals emanating from loaded microwells 178 and 182 are measured at predetermined time intervals using robotic device 50 to move ID rotors 16 to and from racks 228 as required and to and from ID rotor optical analyzer 230. After the completion of an ID test protocol, ID rotors 16 are deposited in trash receptacle 49.

In a similar manner, the analyzer is also programmed to automatically select the numbers of different AST test arrays 12 and broth containers 14 required to complete the requested AST tests. AST canister post 20 is automatically rotated to present the AST canisters 18 containing the required AST test arrays 12 to AST array dispenser 84 and to load the AST test arrays 12 onto AST carriers 74 for transportation to various filling, incubation and testing stations.

Filled AST arrays 12, using the process described in FIGS. 15A–M, are transported by AST carrier transporter 76 to the array filling station 82 where inoculum-broth solution is dispersed to all test microwells 124 in the individual arrays 12 using vacuum-filling means. To fill the microwells 124 with an inoculum-broth solution to be tested, pipetting system 46 dispenses a predetermined quantity of inoculum-broth solution into reservoir 134 within each AST test array 12 carried on AST carriers 74 as described in conjunction with FIG. 15. When all of the reservoirs 134 have been loaded with inoculum-broth solution, AST carrier transporter 76 moves the AST array carrier 74 to AST array vacuum filling station 82 where a clam-shell like vacuum chamber is lowered over the AST array carrier 74 and a vacuum is applied to all AST test arrays 12 carried thereon. Vacuum filling station 82 used to fill test wells in AST test arrays 12 employs techniques that are generally known in the art and typically includes means to generate and release a vacuum within an AST test array 12 and consists generally of a vacuum pump, appropriate vacuum control valves, air filters and pressure transducers that are controlled by CPU 15 to apply and release vacuum in a manner to not cause an excessive amount of bubble formation when the sealable air port 138 is sealed and the AST test array 12 released to atmospheric pressure. When vacuum is applied around the test arrays 12, air is removed from all AST microwells 124 through the sealable vacuum port 138 which is in fluid communication with individual AST microwells 124 by means of microchannels 142 and 143. Subsequent to this evacuation process, a source of heat, for example a previously heated bar having hot-feet portions or an electrical-resistant wire supported within the vacuum chamber may be brought in contact with vacuum port 138 and heated by electrical current for a predetermined time to seal or close port 138 against air flow when vacuum is released; once port 138 is sealed, the vacuum is released within vacuum chamber. Alternately, a resilient stopper may be pressed against an air port separate from the evaporation well as previously described. Atmospheric pressure over the inoculum-broth solution in reservoir 134 causes inoculum-broth solution to flow through opening 140 into microchannels 130, 142 and 143 thereby filling the sacrificial evaporation well 132 and into all microwells 124 in each of the AST test arrays 12 carried by AST array carrier 74. As the microwells 124 are filled with inoculum-broth solution, all remaining air trapped within the chamber 158 will flow into the small recessed top edge portion 160 which acts as a bubble trap within microwell 124.

The AST test arrays 12 are removed from vacuum filling station 82 and transported to the analysis and incubation chamber 70 by AST carrier transporter 76. AST testing may be accomplished within analysis and incubation chamber 70 by AST array reader 90 using a beam of interrogating radiation from above or below each AST array 12 through the polished central arc portion 157 of the top surface 150 of each microwell 124 and measuring the degree of absorption or change in color or generation of a fluorescent signal using a colorimetric or fluorometric photodetector located below or above each microwell 124.

Broth is supplied to the analyzer 10 in prefilled broth containers 16 typically containing four different types of broth. CPU 15 is programmed to automatically identify the type of broth container 16 needed to perform the requested AST tests and to rotate B/ID carousel 26 to present the requisite broth container 14 to the broth container handling apparatus 108 and thereby to pipetting apparatus 46. As described previously, pipetting apparatus 46 is adapted to remove a known amount of inoculum from a sample tube 34 and deposit inoculum into broth container 14 at position 46c where inoculum and broth are mixed using vortex mixer 93, and then aspirated from the broth container 14 as an inoculum-broth solution and deposited into the aforementioned inoculum-broth reservoir 134 of individual test arrays 12.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. An elongate canister comprising a generally rectangular cross-section formed by two canister flat sides and two canister narrow sides, the flat sides being greater in dimension than the narrow sides, the sides extending between the top and bottom of the canister and having dimensions so that a generally rectangularly shaped interior is formed to house a plurality of antibiotic susceptibility test arrays stacked one atop another within the canister, the canister further comprising a number of internal ribs extending along the elongate height of the flat sides adapted to secure the test arrays within the canister.

2. The canister of claim 1 further comprising a top end portion and a bottom end portion closing the top and bottom of the canister.

3. The canister of claim 2 further comprising a canister seating flange extending the full length of a canister narrow side except for a small alignment key and alignment notch adapted to be insertable within a corresponding slot for the alignment key and stop for the alignment notch within an environmentally controlled chamber so as to provide proper mounting orientation of the canister.

4. The canister of claim 3 further comprising a cylindrical pivot extending slightly below the alignment notch and shaped to seat into a mating dock within the chamber to allow the canister to be rotated to a vertical position where the seating flange is insertable into a vertical groove within the environmentally controlled chamber.

5. The canister of claim 4 further comprising an eject port formed in a narrow side proximate the cylindrical pivot and sized to allow the lowermost antibiotic susceptibility test array within the plurality of antibiotic susceptibility test arrays stacked one atop another to be pushed out of the canister.

6. The canister of claim 5 further comprising a plunger port aligned with the eject port and is formed in the narrow side opposing eject port.

7. The canister of claim 5 further comprising a pair of inwardly projecting dimples formed in the flat sides and extending into the eject port a distance to retain antibiotic susceptibility test arrays within the canister, to impede accidental dislodging of a test array from the canister and to impede arrays from being improperly inserted back into canister.

8. The canister of claim 1 comprising an indented sheet of plastic folded in half and sealed at a flange extending the full length of the canister between a flat side and a narrow side.

9. The canister of claim 8 further comprising a sealed fold extending the full length of the canister between the flat side and the opposite narrow side.

* * * * *